(12) United States Patent
Tardi et al.

(10) Patent No.: US 10,058,507 B2
(45) Date of Patent: *Aug. 28, 2018

(54) COMPOSITIONS FOR DELIVERY OF DRUG COMBINATIONS

(71) Applicant: CELATOR PHARMACEUTICALS, INC., Ewing, NJ (US)

(72) Inventors: Paul Tardi, Surrey (CA); Troy Harasym, North Vancouver (CA); Murray Webb, North Vancouver (CA); Clifford Shew, Vancouver (CA); Andrew Janoff, Yardley, PA (US); Lawrence Mayer, North Vancouver (CA); Marcel Bally, Bowen Island (CA)

(73) Assignee: CELATOR PHARMACEUTICALS, INC., Ewing, NJ (US)

( * ) Notice: Subject to any disclaimer, the term of this patent is extended or adjusted under 35 U.S.C. 154(b) by 347 days.

This patent is subject to a terminal disclaimer.

(21) Appl. No.: 14/990,167

(22) Filed: Jan. 7, 2016

(65) Prior Publication Data

US 2016/0113871 A1 Apr. 28, 2016

Related U.S. Application Data

(63) Continuation of application No. 10/553,373, filed as application No. PCT/US2004/011812 on Apr. 16, (Continued)

(51) Int. Cl.
*A61K 9/127* (2006.01)
*A61K 31/00* (2006.01)
(Continued)

(52) U.S. Cl.
CPC ............ *A61K 9/127* (2013.01); *A61K 9/1271* (2013.01); *A61K 9/1272* (2013.01); *A61K 31/00* (2013.01);
(Continued)

(58) Field of Classification Search
CPC ........ A61K 9/127; A61K 9/0019; A61K 9/16; A61K 8/0291
See application file for complete search history.

(56) References Cited

U.S. PATENT DOCUMENTS

| 4,996,237 A | 2/1991 | Pettit et al. |
| 5,000,958 A | 3/1991 | Fountain et al. |

(Continued)

FOREIGN PATENT DOCUMENTS

| GB | 1125409 | 8/1968 |
| JP | 07277956 | 10/1995 |

(Continued)

OTHER PUBLICATIONS

Barriere et al., Pharmacotherapy (1992) 12:397-402.
(Continued)

*Primary Examiner* — Gollamudi Kishore
(74) *Attorney, Agent, or Firm* — Morrison & Foerster LLP

(57) ABSTRACT

Compositions which comprise delivery vehicles having stably associated therewith non-antagonistic combinations of two or more agents, such as antineoplastic agents, are useful in achieving non-antagonistic effects when combinations of drugs are administered.

20 Claims, 34 Drawing Sheets

Related U.S. Application Data 2004, which is a continuation of application No. 10/417,631, filed on Apr. 16, 2003, now Pat. No. 7,850,990, which is a continuation-in-part of application No. 10/264,538, filed on Oct. 3, 2002, now abandoned.

(60) Provisional application No. 60/326,671, filed on Oct. 3, 2001, provisional application No. 60/341,529, filed on Dec. 17, 2001, provisional application No. 60/356,759, filed on Feb. 15, 2002, provisional application No. 60/401,984, filed on Aug. 7, 2002, provisional application No. 60/408,733, filed on Sep. 6, 2002.

(51) Int. Cl.
| | | |
|---|---|---|
| A61K 31/337 | (2006.01) | |
| A61K 31/4745 | (2006.01) | |
| A61K 31/704 | (2006.01) | |
| A61K 31/7048 | (2006.01) | |
| A61K 31/7072 | (2006.01) | |
| A61K 31/7076 | (2006.01) | |
| A61K 33/24 | (2006.01) | |
| A61K 45/06 | (2006.01) | |
| A61K 31/133 | (2006.01) | |
| A61K 31/17 | (2006.01) | |
| A61K 31/475 | (2006.01) | |
| A61K 31/513 | (2006.01) | |
| A61K 31/519 | (2006.01) | |
| A61K 31/555 | (2006.01) | |
| A61K 31/575 | (2006.01) | |
| A61K 31/685 | (2006.01) | |
| A61K 31/7068 | (2006.01) | |
| A61K 39/00 | (2006.01) | |

(52) U.S. Cl.
CPC ............ *A61K 31/133* (2013.01); *A61K 31/17* (2013.01); *A61K 31/337* (2013.01); *A61K 31/475* (2013.01); *A61K 31/4745* (2013.01); *A61K 31/513* (2013.01); *A61K 31/519* (2013.01); *A61K 31/555* (2013.01); *A61K 31/575* (2013.01); *A61K 31/685* (2013.01); *A61K 31/704* (2013.01); *A61K 31/7048* (2013.01); *A61K 31/7068* (2013.01); *A61K 31/7072* (2013.01); *A61K 31/7076* (2013.01); *A61K 33/24* (2013.01); *A61K 39/00* (2013.01); *A61K 45/06* (2013.01)

(56) References Cited

U.S. PATENT DOCUMENTS

| | | | |
|---|---|---|---|
| 5,055,291 | A | 10/1991 | Lam et al. |
| 5,059,421 | A | 10/1991 | Loughrey et al. |
| 5,116,823 | A | 5/1992 | Calabresi et al. |
| 5,547,940 | A | 8/1996 | Nice et al. |
| 5,736,155 | A | 4/1998 | Bally et al. |
| 5,795,589 | A | 8/1998 | Mayer et al. |
| 6,083,530 | A | 7/2000 | Mayer et al. |
| 6,214,821 | B1 | 4/2001 | Daoud |
| 6,469,058 | B1 | 10/2002 | Grove |
| 6,562,834 | B2 | 5/2003 | Bissery |
| 2002/0035090 | A1 | 3/2002 | Zeldis et al. |
| 2002/0090392 | A1 | 7/2002 | Campbell et al. |
| 2002/0103141 | A1* | 8/2002 | McKearn .............. A61K 31/00 514/43 |
| 2003/0083316 | A1 | 5/2003 | Giles et al. |
| 2003/0087839 | A1 | 5/2003 | Geroni et al. |
| 2003/0147945 | A1 | 8/2003 | Tardi et al. |
| 2004/0022817 | A1 | 2/2004 | Tardi et al. |
| 2004/0265368 | A1 | 12/2004 | Mayer et al. |
| 2006/0165771 | A1 | 7/2006 | Tardi et al. |
| 2006/0240090 | A1 | 10/2006 | Mayer et al. |
| 2007/0148255 | A1 | 6/2007 | Tardi et al. |

FOREIGN PATENT DOCUMENTS

| | | |
|---|---|---|
| WO | WO-00/051641 | 9/2000 |
| WO | WO-00/56362 | 9/2000 |
| WO | WO-00/61141 | 10/2000 |
| WO | WO-00/74634 | 12/2000 |
| WO | WO-01/08663 | 2/2001 |
| WO | WO-01/10416 | 2/2001 |
| WO | WO-01/015733 | 3/2001 |
| WO | WO-01/17508 | 3/2001 |
| WO | WO-01/26627 | 4/2001 |
| WO | WO-01/34130 | 5/2001 |
| WO | WO-01/58910 | 8/2001 |
| WO | WO-01/70268 | 9/2001 |
| WO | WO-03/028696 | 4/2003 |
| WO | WO-04/093795 | 11/2004 |

OTHER PUBLICATIONS

Before the Board of Patent Appeals and Interferences, Examiner's Answer for U.S. Appl. No. 11/304,328, mailed on Mar. 9, 2009, 14 pages.
Bergman et al., Clinical Cancer Research (1996) 2:521-530.
Bonner and Kozelsky, Cancer Chemother. Pharmacol. (1990) 39:109-112.
Chen et al., Chin. Med. Engl. (1999) 112:352-355.
Cunningham, Eur. J. Cancer (1996) 32A(Suppl. 3):S1-S8.
Daoud et al., Cancer Chemother. Pharmacol. (1991) 28:370-376.
Engblom et al., Br. J. Cancer (1999) 79:286-292.
Enzinger and Ilson, Oncology (2000) 14(12, Suppl.14):26-30.
Fischel, Brit. J. Cancer (2001) 84(4):579-585.
Frei et al., Clin. Cancer Res. (1998) 4:2027-2037.
Guichard et al., Biochemical Pharmacology (1998) 55:667-676.
Hofs et al., Anticancer Drugs (1994) 5:35-42.
International Search Report for PCT/US04/11812, dated Feb. 9, 2005, 2 pages.
Kano et al., Leukemia Research (1993) 17(2):113-119.
Kanzawa et al., Int. J. Cancer (1997) 71(3):311-319.
Kobayashi et al., Nippon Chiryo Gakkai Shi (1990) 25:2684-2692.
Kuebler et al., J. Interferon Res. (1990) 10:281-291.
Langer et al., Drugs (1999) 58(Suppl.3):71-75.
Mans et al., Eur. J. Cancer (1999) 35(13):1851-1861.
Massin et al., Med. Pediatr. Oncol. (2002) 39:93-98.
Notice of Reasons for Rejection for Japanese Patent Application No. 2003-532029, dated Nov. 27, 2008, 2 pages.
Notice of Reasons for Rejection and Translation for Japanese Patent Application No. 201034701, dated Nov. 11, 2010, 8 pages.
Saxon et al., J. Liposome Res. (1999) 9:507-522.
Schiffelers et al., J. Pharmacol. Exp. Therapeutic (2001) 298:369-375.
Schimpff, Support Care Cancer (1993) 1:5-18.
Shah and Schwartz, Clin. Cancer Res. (2001) 7:2168-2181.
Shih and Teicher, Current Pharmaceutical Design (2001) 7:1259-1276.
Shlaes et al., Clin. Infect. Dis. 17:S527-S536.
Song et al., Polym. Int. (1999) 48:627-629.
Stevenson et al., Oncology (2000) 14(10, Suppl. 9):91-92.
Supplementary Partial European Search Report for EP 04759934.5, dated Aug. 28, 2007, 7 pages.
Swaffar et al., Anti-Cancer Drugs (1995) 6:586-593.
Thigpen, Seminars in Oncology (2002) 29(1, Suppl. 1):11-16.
Todd et al., J. Clin. Oncol. (1984) 2:986-993.
Translation of Decision of Rejection for JP 2003-532029, dated Oct. 19, 2009.
Vaage et al., Int. J. Cancer (1993) 54:959-964.
Vogler, Oncology (1993) 50(Suppl.2):42-46.
Final Office Action from U.S. Appl. No. 10/264,538, dated Dec. 27, 2006.

(56) References Cited

OTHER PUBLICATIONS

Amendment Under 37 CFR 1.116 from U.S. Appl. No. 10/264,538, filed on Jul. 30, 2007.
U.S. Appl. No. 10/406,913, filed Apr. 2, 2003.
Non-Final Office Action from U.S. Appl. No. 10/417,631, dated Apr. 23, 2007.
Amendment Under 37 CFR 1.111 from U.S. Appl. No. 10/417,631, filed on Jul. 30, 2007.
Non-Final Office Action from U.S. Appl. No. 10/817,735, dated Jul. 6, 2007.
Non-Final Office Action for U.S. Appl. No. 10/417,631, dated Jun. 9, 2009, 8 pages.

* cited by examiner

COMPOSITIONS FOR DELIVERY OF DRUG COMBINATIONS

CROSS-REFERENCE TO RELATED APPLICATIONS

This application is a continuation of U.S. Ser. No. 10/553,373 having an international filing date of 16 Apr. 2004, which is the national phase of PCT application PCT/US2004/011812 filed 16 Apr. 2004, which is a continuation of U.S. application Ser. No. 10/417,631 filed 16 Apr. 2003 (now U.S. Pat. No. 7,850,990), which is a continuation-in-part of U.S. Ser. No. 10/264,538 filed 3 Oct. 2002 (abandoned), which claims benefit under 35 U.S.C. § 119(e) of provisional applications U.S. Ser. No. 60/326,671 filed 3 Oct. 2001; Ser. No. 60/341,529 filed 17 Dec. 2001; Ser. No. 60/356,759 filed 15 Feb. 2002; Canadian informal application Serial No. CA 2,383,259 filed 23 Apr. 2002; provisional applications U.S. Ser. No. 60/401,984 filed 7 Aug. 2002 and U.S. Ser. No. 60/408,733 filed 6 Sep. 2002. The contents of these applications are incorporated herein by reference.

TECHNICAL FIELD

The invention relates to compositions and methods for improved delivery of synergistic or additive combinations of therapeutic agents. More particularly, the invention concerns delivery systems which ensure the maintenance of synergistic or additive ratios when the agents are delivered to an intended target by providing formulations comprising delivery vehicles.

BACKGROUND ART

The progression of many life-threatening diseases such as cancer, AIDS, infectious diseases, immune disorders and cardiovascular disorders is influenced by multiple molecular mechanisms. Due to this complexity, achieving cures with a single agent has been met with limited success. Thus, combinations of agents have often been used to combat disease, particularly in the treatment of cancers. It appears that there is a strong correlation between the number of agents administered and cure rates for cancers such as acute lymphocytic leukemia. (Frei, et al., *Clin. Cancer Res.* (1998) 4:2027-2037). Clinical trials utilizing combinations of doxorubicin, cyclophosphamide, vincristine, methotrexate with leucovorin rescue and cytarabine (ACOMLA) or cyclophosphamide, doxorubicin, vincristine, prednisone and bleomycin (CHOP-b) have been successfully used to treat histiocytic lymphoma (Todd, et al., *J. Clin. Oncol.* (1984) 2:986-993).

The effects of combinations of drugs are enhanced when the ratio in which they are supplied provides a synergistic effect. Synergistic combinations of agents have also been shown to reduce toxicity due to lower dose requirements, to increase cancer cure rates (Barriere, et al., *Pharmacotherapy* (1992) 12:397-402; Schimpff, *Support Care Cancer* (1993) 1:5-18), and to reduce the spread of multi-resistant strains of microorganisms (Shlaes, et al., *Clin. Infect. Dis.* (1993) 17:S527-S536). By choosing agents with different mechanisms of action, multiple sites in biochemical pathways can be attacked thus resulting in synergy (Shah and Schwartz, *Clin. Cancer Res.* (2001) 7:2168-2181). Combinations such as L-canavanine and 5-fluorouracil (5-FU) have been reported to exhibit greater antineoplastic activity in rat colon tumor models than the combined effects of either drug alone (Swaffar, et al., *Anti-Cancer Drugs* (1995) 6:586-593). Cisplatin and etoposide display synergy in combating the growth of a human small-cell lung cancer cell line, SBC-3 (Kanzawa, et al., *Int. J. Cancer* (1997) 71(3):311-319).

Additional reports of synergistic effects are found for:

Vinblastine and recombinant interferon-β (Kuebler, et al., *J. Interferon Res.* (1990) 10:281-291);

Cisplatin and carboplatin (Kobayashi, et al., *Nippon Chiryo Gakkai Shi* (1990) 25:2684-2692);

Ethyl deshydroxy-sparsomycin and cisplatin or cytosine arabinoside (AraC) or methotrexate or 5-FU or vincristine (Hofs, et al., *Anticancer Drugs* (1994) 5:35-42);

All trans retinoic acid and butyric acid or tributyrin (Chen, et al., *Chin. Med. Engl.* (1999) 112:352-355); and Cisplatin and paclitaxel (Engblom, et al., *Br. J. Cancer* (1999) 79:286-292).

In the foregoing studies, the importance of the ratio of the components for synergy was recognized. For example, 5-fluorouracil and L-canavanine were found to be synergistic at a mole ratio of 1:1, but antagonistic at a ratio of 5:1; cisplatin and carboplatin showed a synergistic effect at an area under the curve (AUC) ratio of 13:1 but an antagonistic effect at 19:5.

Other drug combinations have been shown to display synergistic interactions although the dependency of the interaction on the combination ratio was not described. This list is quite extensive and is composed mainly of reports of in vitro cultures, although occasionally in vivo studies are included.

In addition to the multiplicity of reports, a number of combinations have been shown to be efficacious in the clinic. These are described in the table below.

| REFERENCE | DRUG 1 | DRUG 2 | DRUG 3 |
| --- | --- | --- | --- |
| Langer, et al. (1999) Drugs 58 Suppl. 3: 71-75 | Cisplatin or Vindesine | +UFT (Tegafur/uracil) | |
| FDA[a] (Colon or Rectal Cancer) | Leucovorin | +5-FU | |
| FDA (Colon or Rectal Cancer) | Irinotecan | +Leucovorin | +5-FU |
| FDA (Breast Cancer) | Herceptin | +Paclitaxel | |
| FDA (Breast Cancer) | Xeloda (other names: Capecitabine) | +Docetaxel | |
| FDA (Ovarian and Lung Cancer) | Paclitaxel | +Cisplatin | |
| FDA (Lung Cancer) | Etoposide | +Other FDA-approved Chemotherapeutic agents | |
| FDA (Lung Cancer) | Gemcitabine | +Cisplatin | |
| FDA (Prostate) | Novantrone (mitoxantrone hydrochloride) | +Corticosteroids | |

-continued

| REFERENCE | DRUG 1 | DRUG 2 | DRUG 3 |
|---|---|---|---|
| FDA (Acute Nonlymphocytic Leukemia) | Novantrone | +Other FDA-approved drugs | |
| FDA (Acute Nonlymphocytic Leukemia/Acute Lymphocytic Leukemia) | Daunorubicin (DNR, Cerubidine) | +Other FDA-approved drugs | |
| FDA (Chronic Myelogenous Leukemia) | Busulfex (Busulfan; 1,4-butanediol, dimethanesulfonate; BU, Myleran) | +Cyclophosphamide (Cytoxan) | |

*a*FDA: United States Food and Drug Administration

In addition, certain other combinations can be postulated from various reports in the literature to have the potential for exhibiting non-antagonistic combination effects or clinical efficacy or accepted as the standard of care by region study groups. These are:

| DISEASE | DRUG 1 | DRUG 2 | DRUG 3 |
|---|---|---|---|
| (Colon Cancer) | Oxaloplatin | +5-FU (or FUDR) | +Leucovorin |
| (Metastatic Breast Cancer) | Taxol | +Doxorubicin | |
| | Adriamycin (doxorubicin) | +Cytoxan (cyclophosphamide) | |
| | Methotrexate | +5-FU (or FUDR) | +Cytoxan |
| | Vinblastine | +Doxorubicin | |
| (Non-small Cell Lung Cancer) | Carboplatin | +Taxol | |
| | Cisplatin | +Docetaxel (Taxotere ®) | |
| | Vinorelbine | +Cisplatin | |
| | Irinotecan | +Cisplatin | |
| (Small Cell Lung Cancer) | Carboplatin | +Taxol | |
| | Cisplatin | +Etoposide | |
| (Prostate Cancer) | Estramustine | +Taxol | |
| | Estramustine | +Mitoxantrone | |
| | Estramustine | +Taxotere | |
| (Hodgkin's Lymphoma) | Bleomycin (as part of ABDV: Adriamycin, Bleomycin, DTIC, Vinblastine) | +Vinblastine | |
| (Non-Hodgkin's Lymphoma) | Carboplatin (as part of ICE: Ifosfamide, Carboplatin, Etoposide) | +Etoposide | |
| (Melanoma) | IL-2 | +Cisplatin | |
| (Acute Myeloid Leukemia) | Daunorubicin | +Cytosine Arabinoside | |
| | Vincristine | +Doxorubicin | |
| (Bladder Cancer) | Carboplatin | +Taxol | |
| | Carboplatin | +Gemcitabine | |
| | Gemcitabine | +Taxol | |
| | Vinblastine (as part of MVAC: Methotrexate, Vinblastine, Adriamycin, Cisplatin) | +Doxorubicin | |
| (Head and Neck Cancer) | 5-FU (or FUDR) | +Cisplatin | +Leucovorin |
| (Pancreatic Cancer) | Gemcitabine | +5-FU (or FUDR) | |
| Additional Combinations: | Carboplatin | +5-FU (or FUDR) | |
| | Carboplatin | +Irinotecan | |
| | Irinotecan | +5-FU (or FUDR) | |
| | Vinorelbine | +Carboplatin | |
| | Methotrexate | +5-FU (or FUDR) | |
| | Idarubicin | +AraC | |
| | Adriamycin | +Vinorelbine | |
| | Safingol | +Fenretinide | |

Despite the aforementioned advantages associated with the use of synergistic drug combinations, there are various drawbacks that limit their therapeutic use. For instance, synergy often depends on various factors such as the duration of drug exposure and the sequence of administration (Bonner and Kozelsky, Cancer Chemother. Pharmacol. (1990) 39:109-112). Studies using ethyl deshydroxy-sparsomycin in combination with cisplatin show that synergy is influenced by the combination ratios, the duration of treatment and the sequence of treatment (Hofs, et al., supra).

It is thus known that in order for synergy to be exhibited by a combination of agents, these agents must be present in amounts which represent defined ratios. Indeed, the same combination of drugs may be antagonistic at some ratios, synergistic at others, and additive at still others. It is desirable to avoid antagonistic effects, so that the drugs are at least additive. The present invention recognizes that the result obtained at an individual ratio is also dependent on concentration. Some ratios are antagonistic at one concentration and non-antagonistic at another. The invention ensures ratios of components in the synergistic or additive range by delivering these agents in formulations that maintain the desired or administered ratio when the target location in the subject are reached and by selecting the ratios to be predominantly non-antagonistic at a desired range of concentrations, since the concentration at the target may be different from that administered.

PCT publication WO 00/51641 describes administering a combination of antiviral agents which is said to be synergistic. In vitro tests were used to determine synergistic ratios. However, there is no teaching of any mode of administration which would maintain this ratio in vivo. Indeed, the publication states that the components may be administered sequentially or simultaneously.

PCT publication WO 01/15733 describes putatively synergistic compositions for treating autoimmune disease. Again, the method of formulation does not ensure maintenance of this ratio after delivery.

Daoud, et al., *Cancer Chemother. Pharmacol.* (1991) 28:370-376, describe synergistic cytotoxic actions of cisplatin and liposomal valinomycin on human ovarian carcinoma cells. This paper describes an in vitro assay in which cisplatin which is free and valinomycin which is encapsulated in liposomes are used to treat cultures of CaOV-3, a human ovarian tumor-derived cell line. The authors determined the concentration ranges over which synergism and antagonism was exhibited. Liposome encapsulation was employed to solubilize the valinomycin. As the experiments are performed in vitro, in vivo delivery is irrelevant.

U.S. Pat. No. 6,214,821 issued 10 Apr. 2001 to Daoud, describes pharmaceutical compositions containing topoisomerase I inhibitors and a staurosporine. The claims appear to be based on the discovery that staurosporines have the ability to abrogate topoisomerase I inhibitor-induced S-phase arrest and to enhance its cytotoxicity to human breast cancer cells lacking normal p53 function. No particular pharmaceutical formulation is suggested.

U.S. Pat. No. 5,000,958 to Fountain, et al., describes mixtures of antimicrobial agents encapsulated in liposomes which are said to exert an enhanced therapeutic effect in vivo. Suitable ratios of antimicrobial agents are determined by a combination effect test which empirically tests for synergy in vitro. There is no discussion of assuring a synergistic ratio over a range of concentrations.

Schiffelers, et al., *J. Pharmacol. Exp. Therapeutic* (2001) 298:369-375, describes the in vivo synergistic interaction of liposome co-encapsulated gentamicin and ceftazidime. The desired ratios were determined using a similar combination effect test to that of Fountain (supra), but there is no discussion of determination of a ratio wherein synergism is maintained over a range of concentrations.

The present invention recognizes, first, that it is possible to maintain a determined synergistic or additive ratio of therapeutic agents by controlling the pharmacokinetics of the formulation in which they are administered, and second, that the non-antagonistic ratio must be exhibited over a range of concentrations, since the concentration of components in a drug cocktail which reaches the target tissue may not be the same as that which is administered. The problem of maintaining synergy or additivity is solved by the recognition that when therapeutic agents are encapsulated in (i.e., stably associated with) delivery vehicles, such as liposomes, the delivery vehicles determine the pharmacokinetics and thus agents which are encapsulated will behave in a similar manner, and by selecting ratios which are predominantly synergistic/additive over a range of concentrations.

DISCLOSURE OF THE INVENTION

The invention relates to methods for administering non-antagonistic ratios of therapeutic agents, preferably antitumor drugs, using delivery vehicle compositions that encapsulate two or more agents, wherein the agents are present in the vehicles at ratios synergistic or additive (i.e. non-antagonistic) over a range of concentrations. Prior to encapsulation, the ratios of therapeutic agents in the combination are selected so that the combination exhibits synergy or additivity over a desired concentration range. Encapsulation in delivery vehicles allows two or more agents to be delivered to the disease site in a coordinated fashion, thereby assuring that the agents will be present at the disease site at a non-antagonistic ratio. This result will be achieved whether the agents are co-encapsulated in delivery vehicles, or are separately encapsulated in delivery vehicles administered such that non-antagonistic ratios are maintained at the disease site. The pharmacokinetics (PK) of the composition are controlled by the delivery vehicles themselves such that coordinated delivery is achieved (provided that the PK of the delivery systems are comparable).

Thus, in one aspect, the invention provides a delivery vehicle composition for parenteral administration comprising two or more agents encapsulated in the vehicle composition at a ratio that is synergistic or additive over a desired concentration range. The delivery vehicle composition is prepared by a process comprising encapsulating the agents in the delivery vehicle composition at these ratios. The non-antagonistic ratio of the agents is determined by assessing the biological activity or effects of the agents on relevant cell culture or cell-free systems over a range of concentrations and, in one embodiment, applying an algorithm to determine a "combination index," (CI). As further described below, using recognized algorithms, a combination index can be calculated at each concentration level. Ratios are selected where the CI represents synergy or additivity over a range of concentrations. Preferably the CI is synergistic over a wide concentration range. Preferred agents are antitumor agents. Any method which results in determination of a ratio of agents which maintains a non-antagonistic effect over a desired range of concentrations may be used.

More particularly, the invention relates to a composition which comprises delivery vehicles, said delivery vehicles having encapsulated therein at least a first therapeutic agent and a second therapeutic agent in a mole ratio of the first agent to the second agent which exhibits a non-antagonistic biologic effect to relevant cells in culture or cell-free system over at least 5% of such concentration range where greater than 1% of the cells are affected (Fraction affected ($f_a$)>0.01) or to a composition which comprises delivery vehicles, said delivery vehicles having encapsulated therein at least a first therapeutic agent and a second therapeutic agent in a mole ratio of the first agent to the second agent which exhibits a non-antagonistic cytotoxic effect or cytostatic effect to relevant cells wherein said agents are antineoplastic agents. By "relevant" cells, applicants refer to at least one cell culture or cell line which is appropriate for testing the desired biological effect. For example, if the agent is an antineoplastic agent, a "relevant" cell would be a cell line identified by the Developmental Therapeutics Program (DTP) of the National Cancer Institute (NCI)/National Institutes of Health (NIH) as useful in their anticancer drug discovery program. Currently the DTP screen utilizes 60 different human tumor cell lines. The desired activity on at least one of such cell lines would need to be demonstrated.

In another aspect, the invention is directed to a method to deliver a synergistic or additive ratio of two or more therapeutic agents to a desired target by administering the compositions of the invention. The administration of such compositions need not be in the form of a single composition, but may also include simultaneous or near simultaneous administration of separate compositions comprising therapeutic agents in delivery vehicles such that the pharmacokinetics of the delivery vehicles is coordinated—i.e., designed in such a way that the ratio of therapeutic agents administered is maintained when target tissues or organs are reached. Thus, separate compositions, each comprising delivery vehicles stably associated with one or more therapeutic agents may be delivered to the subject in a ratio of the therapeutic agents which has been determined to be non-antagonistic as described herein.

In another aspect, the invention is directed to a method to prepare a therapeutic composition comprising delivery vehicles, said delivery vehicles containing a ratio of at least two therapeutic agents which is non-antagonistic over a range of concentrations which method comprises providing a panel of at least two therapeutic agents wherein the panel comprises at least one, but preferably a multiplicity of ratios of said agents, testing the ability of the members of the panel to exert a biological effect on a relevant cell culture or cell-free system over a range of concentrations, selecting a member of the panel wherein the ratio provides a synergistic or additive effect on said cell culture or cell-free system over a suitable range of concentrations; and encapsulating (i.e., stably associating) the ratio of agents represented by the successful member of the panel into drug delivery vehicles. The ratio resulting from the determination described above, in addition to being used as a guide for preparing a single formulation, may also be used to determine the relative amounts to be administered to a subject of separate compositions, each comprising delivery vehicles stably associated with at least one therapeutic agent. Thus, the ratios of therapeutic agents herein determined to be additive or synergistic may be supplied to the subject in a single composition or in the correct proportion of separately prepared compositions.

In another aspect, the invention is directed to kits said kits comprising, in separate containers, a first composition comprising a first therapeutic agent stably associated with delivery vehicles and a second composition comprising delivery vehicles stably associated with the second therapeutic agent. The two containers may be calibrated so that the correct proportion of the two compositions is administered; alternatively, or in addition the kit may simply include instructions with regard to the correct ratio.

As further described below, in a preferred embodiment, in designing an appropriate combination in accordance with the method described above, the non-antagonistic ratios are selected as those that have a combination index (CI) of ≤1.1 over a range of at least 5% of those doses or concentrations that affect greater than 1% or more of the cells ($f_a>0.01$), preferably between 20 and 80% of the cells ($f_a=0.2$ to 0.8), as defined by relevant cell culture or cell-free assay systems.

Figure 1:
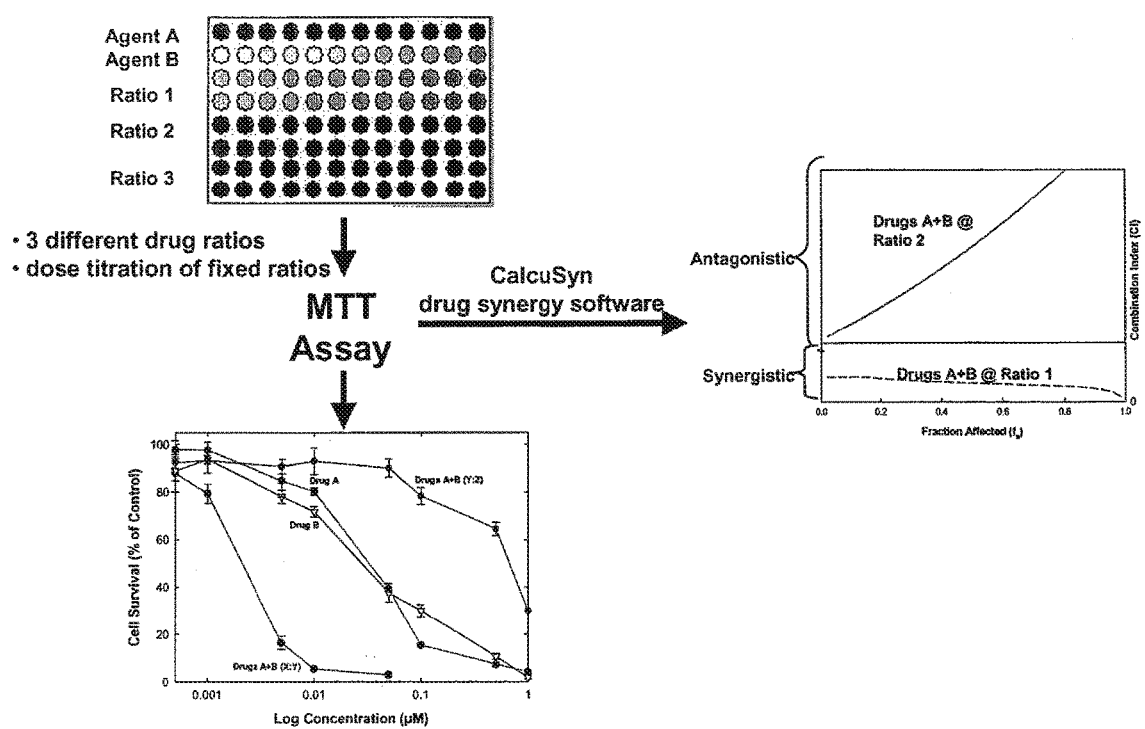
FIG. 1 is a diagram outlining the method of the invention for determining an appropriate ratio of therapeutic agents to include in formulations.

injection of a cocktail of CPT-11/FUDR (open inverted triangles) and the liposomal formulation of CPT-11/FUDR (solid inverted triangles).

MODES OF CARRYING OUT THE INVENTION[1]

The method of the invention involves determining a ratio of therapeutic drugs which is non-antagonistic over a desired concentration range in vitro and supplying this non-antagonistic ratio in a manner that will ensure that the ratio is maintained at the site of desired activity. The synergistic or additive ratio is determined by applying standard analytical tools to the results obtained when at least one ratio of two or more therapeutic agents is tested in vitro over a range of concentrations against relevant cell cultures or cell-free systems. By way of illustration, individual agents and various combinations thereof are tested for their biological effect on cell culture or a cell-free system, for example causing cell death or inhibiting cell growth, at various concentration levels. The concentration levels of the preset ratios are plotted against the percentage cell survival to obtain a correlation which can be manipulated by known and established mathematical techniques to calculate a "combination index" (CI). The mathematics are such that a CI of 1 (i.e., 0.9-1.1) describes an additive effect of the drugs; a CI>1 (i.e., >1.1) represents an antagonist effect; and a CI of <1 (i.e., <0.9) represents a synergistic effect.

[1] Abbreviations
The following abbreviations are used:
PE: phosphatidylethanolamine; PS: phosphatidylserine; DPPS: dipalmitoylphosphatidylserine; DSPS: distearoylphosphatidylserine DLPS: dilauroylphosphatidylserine; DOPS: dioleoylphosphatidylserine; POPS: palmitoyloleoylphosphatidylserine; PC: phosphatidylcholine; SM: sphingomyelin; PG: phosphatidylglycerol; PI: phosphatidylinositol; PA: phosphatidic acid; DSPC: distearoylphosphatidylcholine; DMPC: dimyristoylphosphatidylcholine; DSPG: distearoylphosphatidylglycerol; DSPE: distearoylphosphatidylethanolamine; Chol: cholesterol; CH or CHE: cholesteryl hexadecyl ether;
PEG: polyethylene glycol; DSPE-PEG: distearoylphosphatidylethanolamine-N-[polyethylene glycol]; when PEG is followed by a number, the number is the molecular weight of PEG in Daltons; DSPE-PEG2000: distearoylphosphatidylethanolamine-N-[polyethylene glycol 2000];
SUV: small unilamellar vesicle; LUV: large unilamellar vesicle; MLV: multilamellar vesicle;
MTT: 3-(4,5-dimethylthiazol-2-yl)-2,5-diphenyl-2H tetrazolium bromide; DMSO: dimethylsulfoxide; OD: optical density; OGP: N-octyl beta-D-glucopyranoside; EDTA: ethylenediaminetetraacetic acid; HEPES: N-[2-hydroxylethyl]-piperazine-N-[2-ethanesulfonic acid]; HBS: HEPES buffered saline (20 mM HEPES, 150 mM NaCl, pH 7.4); SHE: 300 mM sucrose, 20 mM HEPES, 30 mM EDTA; ED50, ED75 and ED90: effective dose required to affect 50, 75 and 90% of the cells in culture; LD50: dose required to cause 50% lethality of the cells in culture; CI: combination index; CI max or CI maximum: CI value taken for a single L value (between 0.2 and 0.8) where the greatest difference in CI values for the drugs at different ratios is observed; $f_a$: fraction affected; TEA: triethanolamine;
FDA: United States Food and Drug Administration; NCI: National Cancer Institute.

One general approach is shown in FIG. 1. As shown, agents A and B are tested individually and together at two different ratios for their ability to cause cell death or cell stasis as assessed by the MTT assay described below. Initially, correlations between the concentration of drugs A, B, and the two different combination ratios (Y:Z and X:Y) are plotted against cytotoxicity, calculated as a percentage based on the survival of untreated control cells. As expected, there is a dose-dependent effect on cell survival both for the individual drugs and for the combinations. Once this correlation has been established, the cell survival or fraction affected ($f_a$) can be used as a surrogate for concentration in calculating the CI.

The results of the CI calculation are also shown in FIG. 1; this index is calculated as a function of the fraction of cells affected according to the procedure of Chou and Talalay, *Advance Enz. Regul.* (1985) 22:27-55. In this hypothetical situation, the first ratio (X:Y) of drugs A plus B is non-antagonistic at all concentrations while the combination in the second ratio (Y:Z) is antagonistic. Thus, it is possible to provide a ratio of drugs A plus B (ratio 1) which will be non-antagonistic regardless of concentration over a wide range. It is this ratio that is desirable to include in the compositions of the invention.

Figure 2A:
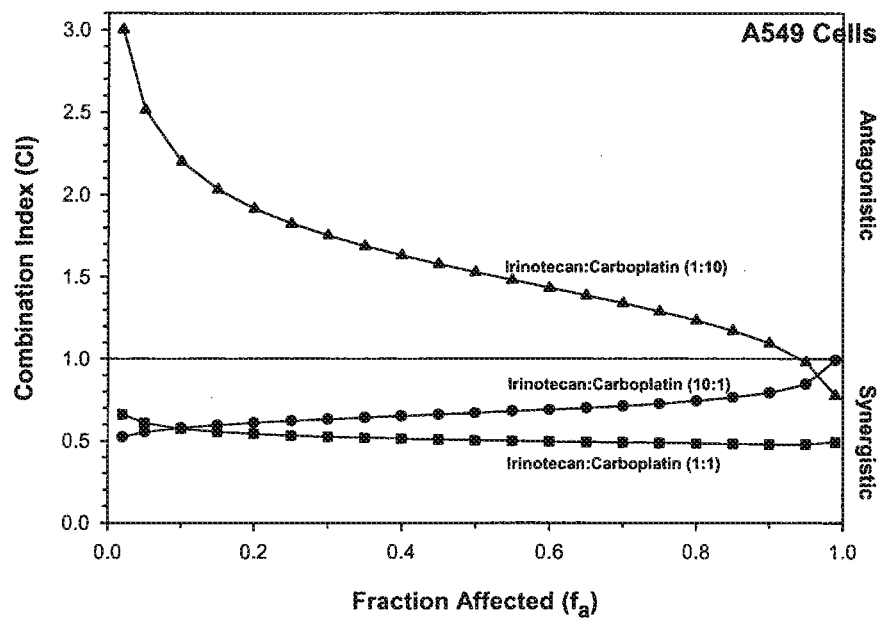
FIGS. 2 (A-E) illustrates 5 methods for presenting combination and synergy data.
Figure 2B:
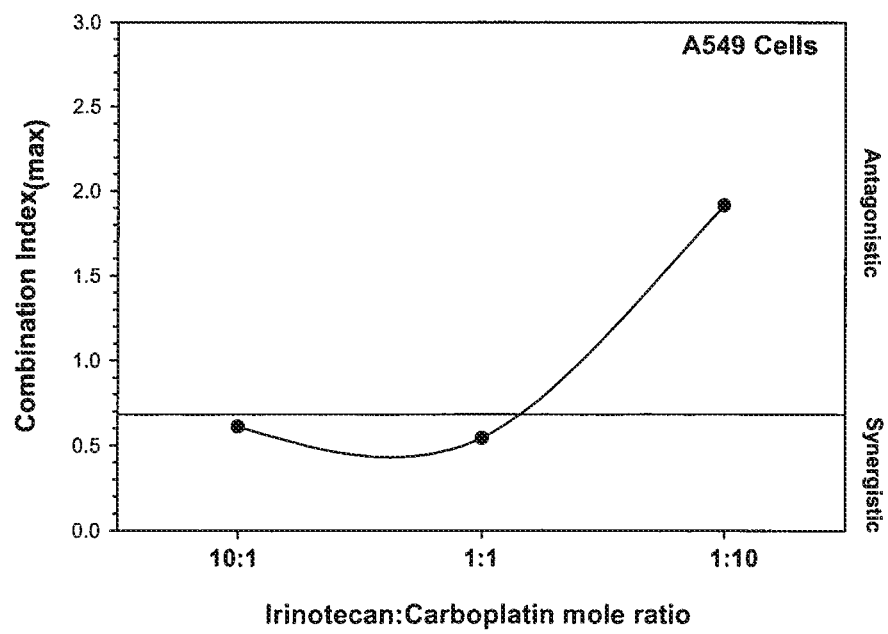

The present inventors have also devised an alternative illustration of the effect of ratio and concentration on synergy by calculating a "CI maximum" for various ratios of combinations of agents. The "CI maximum" is defined as the CI value taken for a single $f_a$ value (between 0.2 and 0.8) where the greatest difference in CI values for the drugs at different ratios was observed. This is illustrated in FIGS. 2A and 2B; as shown, when the irinotecan/carboplatin ratio is 1:10, its CI differs most from that of the remaining ratios where the fraction affected value is 0.2. The CI value for this ratio at $f_a$ 0.2 is, as shown, approximately 2.0.

While the determination in vitro of non-antagonistic ratios has been illustrated for a combination of only two drugs, application of the same techniques to combinations of three or more drugs provides a CI value over the concentration range in a similar manner The ratio obtained in this way is maintained in the pharmaceutical composition by encapsulating the agents in the predetermined ratio in liposomes or other particulate forms which assures that the non-antagonistic ratio will be maintained. The compositions, thus, contain delivery vehicles which are particulate in nature and contain the desired ratio of therapeutic agents.

While it is preferred to co-encapsulate the agents so that both are contained in the same delivery vehicle, this is not necessary. Since particulate carriers can share similar pharmacokinetics, the active substances experience coordinated delivery from the formulation even if encapsulated separately.

By "encapsulation", it is meant stable association with the delivery vehicle. Thus, it is not necessary for the vehicle to surround the agent or agents as long as the agent or agents is/are stably associated with the vehicles when administered in vivo. Thus, "stably associated with" and "encapsulated in" or "encapsulated with" or "co-encapsulated in or with" are intended to be synonymous terms. They are used interchangeably in this specification. The stable association may be effected by a variety of means, including covalent bonding to the delivery vehicle, preferably with a cleavable linkage, noncovalent bonding, and trapping the agent in the interior of the delivery vehicle and the like. The association must be sufficiently stable so that the agents remain associated with the delivery vehicle at a non-antagonistic ratio until it is delivered to the target site in the treated subject.

Delivery vehicles may include lipid carriers, liposomes, lipid micelles, lipoprotein micelles, lipid-stabilized emulsions, cyclodextrins, polymer nanoparticles, polymer microparticles, block copolymer micelles, polymer-lipid hybrid systems, derivatized single chain polymers, and the like. Liposomes can be prepared as described in *Liposomes: Rational Design* (A. S. Janoff ed., Marcel Dekker, Inc., N.Y.), or by additional techniques known to those knowledgeable in the art. Liposomes for use in this invention may be prepared to be of "low-cholesterol." Such liposomes are "cholesterol free," or contain "substantially no cholesterol," or "essentially no cholesterol." The term "cholesterol free" as used herein with reference to a liposome means that a liposome is prepared in the absence of cholesterol. The term "substantially no cholesterol" allows for the presence of an amount of cholesterol that is insufficient to significantly alter the phase transition characteristics of the liposome (typically less than 20 mol % cholesterol). The incorporation of less than 20 mol % cholesterol in liposomes can allow for retention of drugs not optimally retained when liposomes are prepared with greater than 20 mol % cholesterol. Additionally, liposomes prepared with less than 20 mol % cholesterol display narrow phase transition temperatures, a property that may be exploited for the preparation of liposomes that release encapsulated agents due to the application of heat (thermosensitive liposomes). Liposomes of the invention may also contain therapeutic lipids, which include ether lipids, phosphatidic acid, phosphonates, ceramide and ceramide analogues, sphingosine and sphingosine analogues and serine-containing lipids. Liposomes may also be prepared with surface stabilizing hydrophilic polymer-lipid conjugates such as polyethylene glycol-DSPE, to enhance circulation longevity. The incorporation of negatively charged lipids such as phosphatidylglycerol (PG) and phosphatidylinositol (PI) may also be added to liposome formulations to increase the circulation longevity of the carrier. These lipids may be employed to replace hydrophilic polymer-lipid conjugates as surface stabilizing agents. Embodiments of this invention may make use of cholesterol-free liposomes containing PG or PI to prevent aggregation thereby increasing the blood residence time of the carrier.

Micelles are self-assembling particles composed of amphipathic lipids or polymeric components that are utilized for the delivery of sparingly soluble agents present in the hydrophobic core. Various means for the preparation of micellar delivery vehicles are available and may be carried out with ease by one skilled in the art. For instance, lipid micelles may be prepared as described in Perkins, et al., *Int. J. Pharm.* (2000) 200(1):27-39 (incorporated herein by reference). Lipoprotein micelles can be prepared from natural or artificial lipoproteins including low and high-density lipoproteins and chylomicrons. Lipid-stabilized emulsions are micelles prepared such that they comprise an oil filled core stabilized by an emulsifying component such as a monolayer or bilayer of lipids. The core may comprise fatty acid esters such as triacylglycerol (corn oil). The monolayer or bilayer may comprise a hydrophilic polymer lipid conjugate such as DSPE-PEG. These delivery vehicles may be prepared by homogenization of the oil in the presence of the polymer lipid conjugate. Agents that are incorporated into lipid-stabilized emulsions are generally poorly water-soluble. Synthetic polymer analogues that display properties similar to lipoproteins such as micelles of stearic acid esters or poly(ethylene oxide) block-poly(hydroxyethyl-L-aspartamide) and poly(ethylene oxide)-block-poly(hydroxyhexyl-L-aspartamide) may also be used in the practice of this invention (Lavasanifar, et al., *J. Biomed. Mater. Res.* (2000) 52:831-835).

Cyclodextrins comprise cavity-forming, water-soluble, oligosaccharides that can accommodate water-insoluble drugs in their cavities. Agents can be encapsulated into cyclodextrins using procedures known to those skilled in the art. For example, see Atwood, et al., Eds., "Inclusion Compounds," Vols. 2 & 3, Academic Press, NY (1984); Bender, et al., "Cyclodextrin Chemistry," Springer-Verlag, Berlin (1978); Szeitli, et al., "Cyclodextrins and Their Inclusion Complexes," Akademiai Kiado, Budapest, Hungary (1982) and WO 00/40962.

Nanoparticles and microparticles may comprise a concentrated core of drug that is surrounded by a polymeric shell (nanocapsules) or as a solid or a liquid dispersed throughout a polymer matrix (nanospheres). General methods of preparing nanoparticles and microparticles are described by Soppimath, et al. (*J. Control Release* (2001) 70(1-2):1-20) the reference of which is incorporated herein. Other polymeric delivery vehicles that may be used include block copolymer micelles that comprise a drug containing a hydrophobic core surrounded by a hydrophilic shell; they are generally utilized as carriers for hydrophobic drugs and can be prepared as found in Allen, et al., *Colloids and Surfaces B: Biointerfaces* (1999) November 16(1-4):3-27. Polymer-lipid hybrid systems consist of a polymer nanoparticle surrounded by a lipid monolayer. The polymer particle serves as a cargo space for the incorporation of hydrophobic drugs while the lipid monolayer provides a stabilizing interference between the hydrophobic core and the external aqueous environment. Polymers such as polycaprolactone and poly(d,l-lactide) may be used while the lipid monolayer is typically composed of a mixture of lipid. Suitable methods of preparation are similar to those referenced above for polymer nanoparticles. Derivatized single chain polymers are polymers adapted for covalent linkage of a biologically active agent to form a polymer-drug conjugate. Numerous polymers have been proposed for synthesis of polymer-drug conjugates including polyaminoacids, polysaccharides such as dextrin or dextran, and synthetic polymers such as N-(2-hydroxypropyl)methacrylamide (HPMA) copolymer. Suitable methods of preparation are detailed in Veronese and Morpurgo, *IL Farmaco* (1999) 54(8):497-516 and are incorporated by reference herein.

Delivery vehicles are thus provided such that consistent delivery of the administered ratio of the therapeutic components is accomplished. Thus, the ratio may be maintained by simple co-encapsulation of the agents in the vehicles that comprise the composition or the agents can be encapsulated in separate vehicles if the vehicles control the pharmacokinetics of the composition to maintain non-antagonistic drug ratios in the same manner Preferably, the compositions of the invention are used to deliver compositions of antitumor agents that are not antagonistic. The following detailed description sets forth the manner in which the ratios of therapeutic agents are determined and methods for encapsulating the desired ratios into the delivery systems of the invention.

Briefly, in one scenario, first, individual agents are screened separately in a variety of in vitro or in vivo assays to determine their individual activities. Then, pairs of agents are combined and assayed in the same screening method. In this initial screen, the ratios of the agents are the mole ratios of the concentrations having 50% activity ($IC_{50}$ value) identified previously. Alternatively, other fixed ratios (typically mole ratios of 1:10, 1:1 and 10:1) are chosen based on considerations for formulation purposes. The mean values, calculated based on agent effects on cell survival, and drug doses are entered into the CalcuSyn computer program and the output data is evaluated to define a Combination Index (CI) value as a function of the fraction of cells affected ($f_a$).

The CalcuSyn method has been successfully applied to test various agents such as antitumor drugs, immunosuppressants for organ transplant, combined purging of leukemic cells for autologous bone marrow transplantation, insecticides, biological response modifiers, multiple drug resistance inhibitors, anti-microbial agents, anti-HIV agents, anti-herpetic and other anti-viral agents.

Figure 11A:
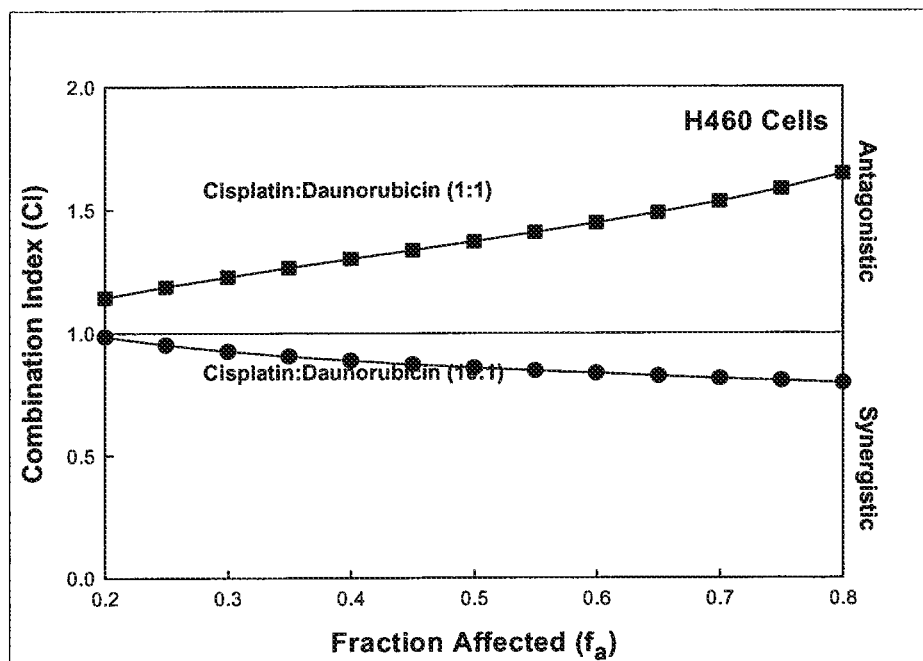
FIG. 11A is a graph of the CI for cisplatin:daunorubicin at mole ratios of 1:1 (filled squares) and 10:1 (filled circles) as a function of the fraction of H460 cells affected ($f_a$).

Combinations of agents displaying interaction behavior similar to that of cisplatin:daunorubicin at a mole ratio of 1:1 in FIG. 11A, i.e., are antagonistic, and are not pursued. Combinations of compounds having non-antagonistic interactions over substantial ranges (preferably at least about 20%) of $f_a$ values greater than fa>0.01 (i.e., irinotecan:carboplatin at mole ratios of 1:1 and 10:1; FIG. 2A) are re-evaluated in this in vitro screening assay at a variety of different drug/drug ratios to define the optimum ratio(s) to enhance both the strength of the non-antagonistic interaction (i.e., lower CI values) and increase the $f_a$ range over which synergy is observed.

Optimized non-antagonistic drug combinations thus identified define a composition for formulation in a delivery vehicle as a dual-agent composition and/or can be used as a single pharmaceutical unit to determine synergistic or additive interactions with a third agent.

In Vitro Determination of Non-Antagonistic Ratios

In order to prepare the compositions of the invention, the desired ratio of agents contained in the delivery vehicles must first be determined. Desirably, the ratio will be that wherein synergy or additivity is exhibited by the combination over a range of concentrations. Such ratios can be determined in vitro in cell cultures or cell-free systems using various mathematical models.

Determination of ratios of agents that display synergistic or additive combination effects over concentration ranges may be carried out using various algorithms, based on the types of experimental data described below. These methods include isobologram methods (Loewe, et al., *Arzneim-Forsch* (1953) 3:285-290; Steel, et al., *Int. J. Radiol. Oncol. Biol. Phys.* (1979) 5:27-55), the fractional product method (Webb, *Enzyme and Metabolic Inhibitors* (1963) Vol. 1, pp. 1-5. New York: Academic Press), the Monte Carlo simulation method, CombiTool, ComboStat and the Chou-Talalay median-effect method based on an equation described in Chou, *J. Theor. Biol.* (1976) 39:253-76; and Chou, *Mol. Pharmacol.* (1974) 10:235-247). Alternatives include surviving fraction (Zoli, et al., *Int. J. Cancer* (1999) 80:413-416), percentage response to granulocyte/macrophage-colony forming unit compared with controls (Pannacciulli, et al., *Anticancer Res.* (1999) 19:409-412) and others (Berenbaum, *Pharmacol. Rev.* (1989) 41:93-141; Greco, et al., *Pharmacol Rev.* (1995) 47:331-385).

The Chou-Talalay median-effect method is preferred. The analysis utilizes an equation wherein the dose that causes a particular effect, $f_a$, is given by:

$$D=D_m[f_a/(1-f_a)]^{1/m}$$

in which D is the dose of the drug used, $f_a$ is the fraction of cells affected by that dose, $D_m$ is the dose for median effect signifying the potency and m is a coefficient representing the shape of the dose-effect curve (m is 1 for first order reactions).

This equation can be further manipulated to calculate a combination index (CI) on the basis of the multiple drug effect equation as described by Chou and Talalay, *Adv. Enzyme Reg.* (1984) 22:27-55; and by Chou, et al., in: *Synergism and Antagonism in Chemotherapy*, Chou and Rideout, eds., Academic Press: New York 1991:223-244. A computer program for this calculation (CalcuSyn) is found in Chou, Dose-effect analysis with microcomputers: quantitation of ED50, LD50, synergism, antagonism, low-dose risk, receptor ligand binding and enzyme kinetics (CalcuSyn Manual and Software; Cambridge: Biosoft 1987).

The combination index equation is based on the multiple drug-effect equation of Chou-Talalay derived from enzyme kinetic models. An equation determines only the additive effect rather than synergism and antagonism. However, according to the CalcuSyn program, synergism is defined as a more than expected additive effect, and antagonism as a less than expected additive effect. Chou and Talalay in 1983 proposed the designation of CI=1 as the additive effect, thus from the multiple drug effect equation of two drugs, we obtain:

$$CI=(D)_1/(D_x)_1+(D)_2/(D_x)_2 \quad \text{[Eq. 1]}$$

for mutually exclusive drugs that have the same or similar modes of action, and it is further proposed that $$CI=(D)_1/(D_x)_1+(D)_2/(D_x)_2+(D_1)(D_2)/(D_x)_1(D_x)_2 \quad \text{[Eq. 2]}$$

for mutually non-exclusive drugs that have totally independent modes of action. CI<1,=1, and >1 indicates synergism, additive effect, and antagonism, respectively. Equation 1 or equation 2 dictates that drug 1, $(D)_1$, and drug 2, $(D)_2$, (in the numerators) in combination inhibit x % in the actual experiment. Thus, the experimentally observed x % inhibition may not be a round number but most frequently has a decimal fraction. $(D_x)_1$ and $(D_x)_2$ (in the denominators) of equations 1 and 2 are the doses of drug 1 and drug 2 alone, respectively, inhibiting x %.

For simplicity, mutual exclusivity is usually assumed when more than two drugs are involved in combinations (CalcuSyn Manual and Software; Cambridge: Biosoft 1987).

The underlying experimental data are generally determined in vitro using cells in culture or cell-free systems. Preferably, the combination index (CI) is plotted as a function of the fraction of cells affected ($f_a$) as shown in FIG. 1 which, as explained above, is a surrogate parameter for concentration range. Preferred combinations of agents are those that display synergy or additivity over a substantial range of $f_a$ values. Combinations of agents are selected that display synergy over at least 5% of the concentration range wherein greater than 1% of the cells are affected, i.e., an $f_a$ range greater than 0.01. Preferably, a larger portion of overall concentration exhibits a favorable CI; for example, 5% of an $f_a$ range of 0.2-0.8. More preferably 10% of this range exhibits a favorable CI. Even more preferably, 20% of the $f_a$ range, preferably over 50% and most preferably over at least 70% of the $f_a$ range of 0.2 to 0.8 are utilized in the compositions. Combinations that display synergy over a substantial range of $f_a$ values may be re-evaluated at a variety of agent ratios to define the optimal ratio to enhance the strength of the non-antagonistic interaction and increase the $f_a$ range over which synergy is observed.

While it would be desirable to have synergy over the entire range of concentrations over which cells are affected, it has been observed that in many instances, the results are considerably more reliable in an $f_a$ range of 0.2-0.8. Thus, although the synergy exhibited by combinations of the invention is set forth to exist within the broad range of 0.01 or greater, it is preferable that the synergy be established in the $f_a$ range of 0.2-0.8.

The optimal combination ratio may be further used as a single pharmaceutical unit to determine synergistic or additive interactions with a third agent. In addition, a three-agent combination may be used as a unit to determine non-antagonistic interactions with a fourth agent, and so on.

As set forth above, the in vitro studies on cell cultures will be conducted with "relevant" cells. The choice of cells will depend on the intended therapeutic use of the agent. Only one relevant cell line or cell culture type need exhibit the required non-antagonistic effect in order to provide a basis for the compositions to come within the scope of the invention.

For example, in one preferred embodiment of the invention, the combination of agents is intended for anticancer therapy. Appropriate choices will then be made of the cells to be tested and the nature of the test. In particular, tumor cell lines are suitable subjects and measurement of cell death or cell stasis is an appropriate end point. As will further be discussed below, in the context of attempting to find suitable non-antagonistic combinations for other indications, other target cells and criteria other than cytotoxicity or cell stasis could be employed.

not limited to, H460, MCF-7, SF-268, HT29, HCT-116, LS180, B16-F10, A549, Capan pancreatic, CAOV-3, IGROV1, PC-3, MX-1 and MDA-MB-231.

In one preferred embodiment, the given effect ($f_a$) refers to cell death or cell stasis after application of a cytotoxic agent to a cell culture. Cell death or viability may be measured, for example, using the following methods:

| CYTOTOXICITY ASSAY | REFERENCE |
|---|---|
| MTT assay | Mosmann, *J. Immunol. Methods* (1983) 65(1-2): 55-63. |
| Trypan blue dye exclusion | Bhuyan, et al., *Experimental Cell Research* (1976) 97: 275-280. |
| Radioactive tritium ($^3$H)-thymidine incorporation or DNA intercalating assay | Senik, et al., *Int. J. Cancer* (1975) 16(6): 946-959. |
| Radioactive chromium-51 release assay | Brunner, et al., *Immunology* (1968) 14: 181-196. |
| Glutamate pyruvate transaminase, creatine phosphokinase and lactate dehydrogenase enzyme leakage | Mitchell, et al., *J. of Tissue Culture Methods* (1980) 6(3&4): 113-116. |
| Neutral red uptake | Borenfreund and Puerner, *Toxicol. Lett.* (1985) 39: 119-124. |
| Alkaline phosphatase activity | Kyle, et al., *J. Toxicol. Environ. Health* (1983) 12: 99-117. |
| Propidium iodide staining | Nieminen, et al., *Toxicol. Appl. Pharmacol.* (1992) 115: 147-155. |
| Bis-carboxyethyl-carboxyfluorescein (BCECF) retention | Kolber, et al., *J. Immunol. Methods* (1988) 108: 255-264. |
| Mitochondrial membrane potential | Johnson, et al., *Proc. Natl. Acad. Sci. USA* (1980) 77: 990-994. |
| Clonogenic Assays | Puck, et al., *J. of Experimental Medicine* (1956) 103: 273-283. |
| LIVE/DEAD Viability/Cytotoxicity assay | Morris, *Biotechniques* (1990) 8: 296-308. |
| Sulforhodamine B (SRB) assays | Rubinstein, et al., *J. Natl. Cancer Instit.* (1990) 82: 1113-1118. |

For determinations involving antitumor agents, cell lines may be obtained from standard cell line repositories (NCI or ATCC for example), from academic institutions or other organizations including commercial sources. Preferred cell lines would include one or more selected from cell lines identified by the Developmental Therapeutics Program of the NCI/NIH. The tumor cell line screen used by this program currently identifies 60 different tumor cell lines representing leukemia, melanoma, and cancers of the lung, colon, brain, ovary, breast, prostate and kidney. The required non-antagonistic effect over a desired concentration range need be shown only on a single cell type; however, it is preferred that at least two cell lines exhibit this effect, more preferably three cell lines, more preferably five cell lines, and more preferably 10 cell lines. The cell lines may be established tumor cell lines or primary cultures obtained from patient samples. The cell lines may be from any species but the preferred source will be mammalian and in particular human. The cell lines may be genetically altered by selection under various laboratory conditions, and/or by the addition or deletion of exogenous genetic material. Cell lines may be transfected by any gene-transfer technique, including but not limited to, viral or plasmid-based transfection methods. The modifications may include the transfer of cDNA encoding the expression of a specific protein or peptide, a regulatory element such as a promoter or enhancer sequence or antisense DNA or RNA. Genetically engineered tissue culture cell lines may include lines with and without tumor suppressor genes, that is, genes such as p53, pTEN and p16; and lines created through the use of dominant negative methods, gene insertion methods and other selection methods. Preferred tissue culture cell lines that may be used to quantify cell viability, e.g., to test antitumor agents, include, but are The "MTT assay" is preferred.

Non-antagonistic ratios of two or more agents can be determined for disease indications other than cancer and this information can be used to prepare therapeutic formulations of two or more drugs for the treatment of these diseases. With respect to in vitro assays, many measurable endpoints can be selected from which to define drug synergy, provided those endpoints are therapeutically relevant for the specific disease.

Thus, for example, one skilled in the art will be able to define non-antagonistic ratios of two or more agents selected for treatment of inflammatory disorders by measuring, in vitro, suppression of proinflammatory cytokines such as IL-1, IL-18, COX-2, TNF or interferon-gamma. Other inflammatory signals include, but are not limited to, inhibition of prostaglandin E2 and thromboxane B2. In particular, endotoxin-mediated macrophage activation provides a suitable in vitro assay for measuring the anti-inflammatory effects of an added agent or combinations of agents and is commonly used in the art. In such an assay, macrophages grown in large quantities are activated by the addition of an endotoxin, such as lipopolysaccharide. Upon activation, macrophage secretion of cytokines such as IL-1 and TNF is measurable as well as activation of COX-2. Candidate anti-inflammatory drugs are added and evaluated based on their ability to suppress IL-1, TNF and COX-2. Titration with $1 \times 10^{-7}$ M dexamethasone is typically used as a positive control. It will be apparent to those skilled in the art that assays involving macrophage activation are suitable for wide-spread screening of drug combinations and that suppression of IL-1, TNF and COX-2 are suitable endpoints for defining synergy. In addition to measuring inflammatory signals, investigators can consider the use of in vitro models that measure the effect of two or more agents on leukocyte functions. Functional tests can involve, but are not limited to, inhibition of degranulation, superoxide generation, and leukocyte migration.

Similar to cancer, proliferation is a key event in the development of arteriosclerosis, restenosis or other cardiovascular diseases with vasculoproliferative attributes. Thus, one skilled in the art can find non-antagonistic ratios of two or more agents by assessing drug synergy by the methods set forth herein, applied to relevant proliferating cell populations of blood vessels. In particular, restenosis, such as coronary and peripheral artery restenosis that typically results following angioplasty, is attributable to smooth muscle and endothelial cell proliferation (Fuster, *Arch Mal Coeur Vaiss* (1997) 90 Spec No 6:41-47). Using standard methods, set forth herein, one skilled in the art can measure whether two or more agents act non-antagonistically to inhibit endothelial cell or smooth muscle cell proliferation. These assays can be undertaken using immortalized cell lines or, preferably, using primary cell lines. These cell lines can be obtained from commercial sources (e.g., Clonetics, California) or from fresh tissue (e.g., umbilical veins, arteries, brain) and must be maintained in appropriate growth factors that promote cell proliferation. Similar to assays measuring synergy of two or more agents on cancer cells, such assays can include, but are not limited to, endpoints of inhibition of proliferation and migration. Proliferation endpoints can rely on live/dead assays such as the MTT assay described in this application, measurements of proliferation that rely on [$^3$H]-thymidine incorporation, or other similar assays. Also similar to dividing cancer cells, proliferation of endothelial cells and smooth muscle cells is regulated by checkpoints in the cell cycle and assays that measure cell cycle inhibition can be used to define non-antagonistic ratios of two or more agents selected for treatment of vasculoproliferative disorders.

Non-antagonistic combinations of agents may also be identified for their activity against microbial or viral infections. As a first step in identifying antimicrobial agents, the minimum inhibitory concentration (MIC) for an agent can be determined by the classical microtitre broth dilution or agar dilution antimicrobial assays known to those skilled in the art. These assays are regulated by the National Committee of Laboratory Safety and Standards (NCLSS). The standard broth dilution assays are published in Amsterdam (1996) Susceptibility testing of Antimicrobials in liquid media in "Antibiotics in Laboratory Medicine", Lorian, V. 4$^{th}$ Edition, pages 52-111, Williams and Wilkins, Baltimore. The MIC is defined as the lowest concentration of an antibiotic that will inhibit the in vitro growth of an infectious organism. In the above-mentioned assays, the MIC can be determined by plating an inoculum of microbes in a small spot (at, for example, 10$^4$ colony-forming units [CFU] per spot) on growth medium (for example, agar) having different concentrations of the drug. Alternatively, microbes can be inoculated into a suspension of growth media that contains different concentrations of the drug. In addition, the microbes may be either treated as above or may be resident as intracellular infections in a specific cell population (i.e., a macrophage). In the latter instance, mammalian cells grown in culture by standard methods are given intracellular microbial infections by brief exposure to a low concentration of microbes. After a period of time to allow the intracellular replication of the microbes, the cells and their intracellular microbes are treated with a drug in the same manner as described for cytotoxicity tests with mammalian cells. After an appropriate period of time sufficient for the drug to inhibit microbial growth when given at effective concentrations, the bacterial growth can be determined by a variety of means including: (i) determination of the absence or presence (and size, as appropriate) of the inoculum spot; (ii) plating and serial dilution of known volumes of the suspension of treated bacteria onto agar growth plates to allow calculation of the number of microbes that survived treatment; (iii) macroscopic (by eye) determination; (iv) time-kill curves in which microbes in the logarithmic phase of growth are suspended into a growth media containing a drug(s) and, at various times after inoculation, known volumes are removed and serial diluted onto growth agar for counting of the surviving microbes; (v) other spectroscopic, analytic, in vitro or in vivo methods known by those skilled in the art to allow the counting of viable microbes. The efficacy of a drug, or combinations of drugs to kill intracellular-resident infections are typically assessed after the host cells are lysed with detergents (such as 1% Triton X-100 plus 0.1% sodium dodecyl sulfate) to release the microbes, then the lysates are serial diluted onto agar growth plates for counting of the numbers of surviving microbes.

Combinations of effective agents are assessed for their antagonistic, additive or synergistic activity using the means described above. Specifically, pairs of compounds are applied to the bacteria in fixed ratios that can be equimolar, or the ratio of the MIC values or other fixed ratios, and the bacteria treated at a variety of concentrations of the pair of compounds. Activity is determined as described above. Antagonism, additivity or synergy are determined from a variety of mathematical treatments for example by isobolograms, CI, and the like.

Extensive screening of agents or combinations of agents with antiviral activity can be performed by a number of in vitro assays, typically plaque reduction and cytopathic effects (CPE) inhibition assays, which are well known to those of skill in the art. These assays are able to directly measure the extent to which an antiviral drug or drugs inhibits the effects of viral infection in tissue culture. The plaque reduction assay is preferred for virus and cell line combinations which produce a well-defined plaque. Michaelis, et al., demonstrated the use of plaque reduction assays combined with the Chou-Talalay method for determining non-antagonistic antiviral effects of aphidicolin and its derivatives on a number of viruses at various mole ratios (Michaelis, et al., *Arzneimittelforschung* (2002) 52(5):393-399). If a well-defined plaque is not producible by particular virus and cell line combinations, CPE inhibition assays are preferred. Additional methods for rapid and convenient identification of non-antagonistic combinations of antiviral agents include, but are not limited to, cell viability, virus yield and HIV acute or chronic infection assays. Cell viability is used to measure an antiviral agent's or combination of agent's ability to increase cell viability and can be achieved using quantitative assays such as the MTT assay previously described. Alternatively, the virus yield assay and the acute HIV infection assays evaluate an agent's ability to reduce virus yield allowing for direct measurements of antiviral activity. It will be apparent to those knowledgeable in the art that the aforementioned assays are suitable for screening antiviral drug combinations for synergistic, additive or antagonistic effects in vitro and are therefore included within the scope of the invention.

Preferred Agent Combinations

Various combinations of therapeutic agents, having been found to satisfy the criteria for non-antagonistic effects set forth above, are then provided in the form of formulations of drug delivery vehicles. A "therapeutic agent" is a compound that alone, or in combination with other compounds, has a desirable effect on a subject affected by an unwanted condition or disease.

Certain therapeutic agents are favored for use in combination when the target disease or condition is cancer. Examples are:

"Signal transduction inhibitors" which interfere with or prevents signals that cause cancer cells to grow or divide;

"Cytotoxic agents";

"Cell cycle inhibitors" or "cell cycle control inhibitors" which interfere with the progress of a cell through its normal cell cycle, the life span of a cell, from the mitosis that gives it origin to the events following mitosis that divides it into daughter cells;

"Checkpoint inhibitors" which interfere with the normal function of cell cycle checkpoints, e.g., the S/G2 checkpoint, G2/M checkpoint and G1/S checkpoint;

"Topoisomerase inhibitors", such as camptothecins, which interfere with topoisomerase I or II activity, enzymes necessary for DNA replication and transcription;

"Receptor tyrosine kinase inhibitors" which interfere with the activity of growth factor receptors that possess tyrosine kinase activity;

"Apoptosis inducing agents" which promote programmed cell death;

"Antimetabolites," such as Gemcitabine or Hydroxyurea, which closely resemble an essential metabolite and therefore interfere with physiological reactions involving it;

"Telomerase inhibitors" which interfere with the activity of a telomerase, an enzyme that extends telomere length and extends the lifetime of the cell and its replicative capacity;

"Cyclin-dependent kinase inhibitors" which interfere with cyclin-dependent kinases that control the major steps between different phases of the cell cycle through phosphorylation of cell proteins such as histones, cytoskeletal proteins, transcription factors, tumor suppresser genes and the like;

"DNA damaging agents";

"DNA repair inhibitors";

"Anti-angiogenic agents" which interfere with the generation of new blood vessels or growth of existing blood vessels that occurs during tumor growth; and "Mitochondrial poisons" which directly or indirectly disrupt mitochondrial respiratory chain function.

Especially preferred combinations for treatment of tumors are the clinically approved combinations set forth hereinabove. As these combinations have already been approved for use in humans, reformulation to assure appropriate delivery is especially important.

Preferred agents that may be used in combination include DNA damaging agents such as carboplatin, cisplatin, cyclophosphamide, doxorubicin, daunorubicin, epirubicin, mitomycin C, mitoxantrone; DNA repair inhibitors including 5-fluorouracil (5-FU) or FUDR, gemcitabine and methotrexate; topoisomerase I inhibitors such as camptothecin, irinotecan and topotecan; S/G2 or G2/M checkpoint inhibitors such as bleomycin, docetaxel, doxorubicin, etoposide, paclitaxel, vinblastine, vincristine, vindesine and vinorelbine; G1/early-S checkpoint inhibitors; G2/M checkpoint inhibitors; receptor tyrosine kinase inhibitors such as genistein, trastuzumab, ZD1839; cytotoxic agents; apoptosis-inducing agents and cell cycle control inhibitors.

The mechanism of action of one or more of the agents may not be known or may be incorrectly identified. All synergistic or additive combinations of agents are within the scope of the present invention. Preferably, for the treatment of a neoplasm, combinations that inhibit more than one mechanism that leads to uncontrolled cell proliferation are chosen for use in accordance with this invention. For example, the present invention includes selecting combinations that effect specific points within the cell cycle thereby resulting in non-antagonistic effects. For instance, drugs that cause DNA damage can be paired with those that inhibit DNA repair, such as anti-metabolites. The present invention also includes selecting combinations that block multiple pathways that would otherwise result in cell proliferation.

Particularly preferred combinations are DNA damaging agents in combination with DNA repair inhibitors, DNA damaging agents in combination with topoisomerase I or topoisomerase II inhibitors, topoisomerase I inhibitors in combination with S/G2 or G2/M checkpoint inhibitors, G1/S checkpoint inhibitors or CDK inhibitors in combination with G2/M checkpoint inhibitors, receptor tyrosine kinase inhibitors in combination with cytotoxic agents, apoptosis-inducing agents in combination with cytotoxic agents, apoptosis-inducing agents in combination with cell-cycle control inhibitors, G1/S or G2/M checkpoint inhibitors in combination with cytotoxic agents, topoisomerase I or II inhibitors in combination with DNA repair inhibitors, topoisomerase I or II inhibitors or telomerase inhibitors in combination with cell cycle control inhibitors, topoisomerase I inhibitors in combination with topoisomerase II inhibitors, and two cytotoxic agents in combination.

Specific agents that may be used in combination include cisplatin (or carboplatin) and 5-FU (or FUDR), cisplatin (or carboplatin) and irinotecan, irinotecan and 5-FU (or FUDR), vinorelbine and cisplatin (or carboplatin), methotrexate and 5-FU (or FUDR), idarubicin and araC, cisplatin (or carboplatin) and taxol, cisplatin (or carboplatin) and etoposide, cisplatin (or carboplatin) and topotecan, cisplatin (or carboplatin) and daunorubicin, cisplatin (or carboplatin) and doxorubicin, cisplatin (or carboplatin) and gemcitabine, oxaliplatin and 5-FU (or FUDR), gemcitabine and 5-FU (or FUDR), adriamycin and vinorelbine, taxol and doxorubicin, flavopuridol and doxorubicin, UCN01 and doxorubicin, bleomycin and trichlorperazine, vinorelbine and edelfosine, vinorelbine and sphingosine (and sphingosine analogues), vinorelbine and phosphatidylserine, vinorelbine and camptothecin, cisplatin (or carboplatin) and sphingosine (and sphingosine analogues), sphingosine (and sphingosine analogues) and daunorubicin and sphingosine (and sphingosine analogues) and doxorubicin.

Preferred combinations in general include those set forth hereinabove as already shown to be efficacious in the clinic as recognized by the FDA and those further suggested based on literature reports. While the candidate agents for use in the method of the invention are not limited to these specific combinations, those set forth hereinabove have been disclosed as suitable combination therapies, and are thus preferred for use in the methods and compositions of the present invention.

Some lipids are "therapeutic lipids" that are able to exert therapeutic effects such as inducing apoptosis. Included in this definition are lipids such as ether lipids, phosphatidic acid, phosphonates, ceramide and ceramide analogues, dihydroxyceramide, phytoceramide, sphingosine, sphingosine analogues, sphingomyelin, serine-containing lipids and sphinganine The term "serine-containing phospholipid" or "serine-containing lipid" as defined herein is a phospholipid in which the polar head group comprises a phosphate group covalently joined at one end to a serine and at the other end to a three-carbon backbone connected to a hydrophobic portion through an ether, ester or amide linkage. Included in this class are the phospholipids such as phosphatidylserine (PS) that have two hydrocarbon chains in the hydrophobic portion that are between 5-23 carbon atoms in length and have varying degrees of saturation. The term hydrophobic portion with reference to a serine-containing phospholipid or serine-containing lipid refers to apolar groups such as long saturated or unsaturated aliphatic hydrocarbon chains, optionally substituted by one or more aromatic, alicyclic or heterocyclic group(s).

Combinations of therapeutic lipids and other agents can also be used to achieve synergistic or additive effects (see Examples 17-21).

High Throughput Screening for Determining Ratios that Display Non-Antagonistic Combination Effects Chemical libraries of agents may be screened against one another at different ratios to identify novel non-antagonistic drug combinations. Chemical libraries may comprise novel or conventional agents. In addition to screening for two agent combinations, three or four agent combinations may also be screened for non-antagonistic combination effects. Preferably, the data analysis methodology employed to determine drug synergy is the aforementioned Median Effect Analysis. According to this method, libraries of agents are tested individually and in combination at different ratios. Combination indexes are then calculated using the aforementioned method developed by Chou and Talalay. Drug combinations that display non-antagonistic effects at specific ratios are encapsulated in delivery vehicles at a non-antagonistic ratio.

High throughput screening systems are commercially available (see, e.g., Zymark Corp., Hopkinton, Mass.; Air Technical Industries, Mentor, Ohio; Beckman Instruments, Inc. Fullerton, Calif.; Precision Systems, Inc., Natick, Mass., etc.). These systems typically automate entire procedures including all sample and reagent pipetting, liquid dispensing, timed incubations, and final readings of the microplate in detector(s) appropriate for the assay. These configurable systems provide high throughput and rapid start-up, as well as a high degree of flexibility and customization. The manufacturers of such systems provide detailed protocols for the various high throughput screening methods.

Preparation of Non-Antagonistic Compositions

When the appropriate ratios of the agents have been determined as described above, the agents at the appropriate ratio are placed into one or more delivery vehicle compositions wherein one or more delivery vehicles encapsulates two or more agents. Not all the delivery vehicles in the composition need be identical. The delivery vehicles in the compositions are particles of sizes that depend on their route of administration, which can be suspended in an aqueous or other solvent and are able to encapsulate the agents of the invention. Such vehicles include, for example, lipid carriers, liposomes, cyclodextrins, polymer nanoparticles and polymer microparticles, including nanocapsules and nanospheres, block copolymer micelles, lipid stabilized emulsions, derivatized single-chain polymers, polymer lipid hybrid systems, lipid micelles, lipoprotein micelles as mentioned previously. For intravenous administration, delivery vehicles are typically about 4-6,000 nm in diameter. Preferred diameters are about 5-500 nm in diameter, more preferably 5-200 nm in diameter. For inhalation, intra-thecal, intra-articular, intra-arterial, intra-peritoneal or subcutaneous administration, delivery vehicles are typically from 4 µm to an excess of 50 µm. Delivery vehicle compositions designed for intra-ocular administration are generally smaller.

As explained above, the biologically active agents may be formulated into a single composition at the predetermined ratio, or separate compositions comprising delivery vehicles with coordinated pharmacokinetics can be employed along with instructions for administering these compositions in a proportion consistent with the predetermined ratio. Thus, the desired ratio may be achieved by administering the agents in separate compositions simultaneously or sequentially in the proportion described.

The therapeutic agents are "encapsulated" in the delivery vehicles. "Encapsulation," as previously described, includes covalent or non-covalent association of an agent with the delivery vehicle. For example, this can be by interaction of the agent with the outer layer or layers of the delivery vehicle or entrapment of an agent within the delivery vehicle, equilibrium being achieved between different portions of the delivery vehicle. For example, for liposomes, encapsulation of an agent can be by association of the agent by interaction with the bilayer of the liposomes through covalent or non-covalent interaction with the lipid components or entrapment in the aqueous interior of the liposome, or in equilibrium between the internal aqueous phase and the bilayer. For polymer-based delivery vehicles, encapsulation can refer to covalent linkage of an agent to a linear or non-linear polymer. Further, non-limiting examples include the dispersion of agent throughout a polymer matrix, or the concentration of drug in the core of a nanocapsule, a block copolymer micelle or a polymer-lipid hybrid system. "Loading" refers to the act of encapsulating one or more agents into a delivery vehicle.

Encapsulation of the desired combination can be achieved either through encapsulation in separate delivery vehicles or within the same delivery vehicle. Where encapsulation into separate delivery vehicles, such as liposomes, is desired, the lipid composition of each liposome may be quite different to allow for coordinated pharmacokinetics. By altering the vehicle composition, release rates of encapsulated drugs can be matched to allow non-antagonistic ratios of the drugs to be delivered to the tumor site. Means of altering release rates include increasing the acyl-chain length of vesicle forming lipids to improve drug retention, controlling the exchange of surface grafted hydrophilic polymers such as PEG out of the liposome membrane and incorporating membrane-rigidifying agents such as sterols or sphingomyelin into the membrane. It should be apparent to those skilled in the art that if a first and second drug are desired to be administered at a specific drug ratio and if the second drug is retained poorly within the liposome composition of the first drug (e.g., DMPC/Chol), that improved pharmacokinetics may be achieved by encapsulating the second drug in a liposome composition with lipids of increased acyl chain length (e.g., DSPC/Chol). Alternatively, two or more agents may be encapsulated within the same delivery vehicle.

Techniques for encapsulation are dependent on the nature of the delivery vehicles. For example, therapeutic agents may be loaded into liposomes using both passive and active loading methods.

Passive methods of encapsulating agents in liposomes involve encapsulating the agent during the preparation of the liposomes. In this method, the drug may be membrane associated or encapsulated within an entrapped aqueous space. This includes a passive entrapment method described by Bangham, et al., *J. Mol. Biol.* (1965) 12:238, where the aqueous phase containing the agent of interest is put into contact with a film of dried vesicle-forming lipids deposited on the walls of a reaction vessel. Upon agitation by mechanical means, swelling of the lipids will occur and multilamellar vesicles (MLV) will form. Using extrusion, the MLVs can be converted to large unilamellar vesicles (LUV) or small unilamellar vesicles (SUV). Another method of passive loading that may be used includes that described by Deamer and Bangham, *Biochim. Biophys. Acta* (1976) 443:629. This method involves dissolving vesicle-forming lipids in ether and, instead of first evaporating the ether to form a thin film on a surface, this film being thereafter put into contact with an aqueous phase to be encapsulated, the ether solution is directly injected into said aqueous phase and the ether is evaporated afterwards, whereby liposomes with encapsulated agents are obtained. A further method that may be employed is the Reverse Phase Evaporation (REV) method described by Szoka and Papahadjopoulos, *P.N.A.S.* (1978) 75:4194, in which a solution of lipids in a water insoluble organic solvent is emulsified in an aqueous carrier phase and the organic solvent is subsequently removed under reduced pressure.

Other methods of passive entrapment that may be used include subjecting liposomes to successive dehydration and rehydration treatment, or freezing and thawing. Dehydration is carried out by evaporation or freeze-drying. This technique is disclosed by Kirby, et al., *Biotechnology* (1984) 979-984. Also, Shew and Deamer (*Biochim. et Biophys. Acta* (1985) 816:1-8) describe a method wherein liposomes prepared by sonication are mixed in aqueous solution with the solute to be encapsulated, and the mixture is dried under nitrogen in a rotating flask. Upon rehydration, large liposomes are produced in which a significant fraction of the solute has been encapsulated.

Passive encapsulation of two or more agents is possible for many drug combinations. This approach is limited by the solubility of the drugs in aqueous buffer solutions and the large percentage of drug that is not trapped within the delivery system. The loading may be improved by co-lyophilizing the drugs with the lipid sample and rehydrating in the minimal volume allowed to solubilize the drugs. The solubility may be improved by varying the pH of the buffer, increasing temperature or addition or removal of salts from the buffer.

Active methods of encapsulating may also be used. For example, liposomes may be loaded according to a metal-complexation or pH gradient loading technique. With pH gradient loading, liposomes are formed which encapsulate an aqueous phase of a selected pH. Hydrated liposomes are placed in an aqueous environment of a different pH selected to remove or minimize a charge on the drug or other agent to be encapsulated. Once the drug moves inside the liposome, the pH of the interior results in a charged drug state, which prevents the drug from permeating the lipid bilayer, thereby entrapping the drug in the liposome.

To create a pH gradient, the original external medium can be replaced by a new external medium having a different concentration of protons. The replacement of the external medium can be accomplished by various techniques, such as, by passing the lipid vesicle preparation through a gel filtration column, e.g., a Sephadex G-50 column, which has been equilibrated with the new medium (as set forth in the examples below), or by centrifugation, dialysis, or related techniques. The internal medium may be either acidic or basic with respect to the external medium.

After establishment of a pH gradient, a pH gradient loadable agent is added to the mixture and encapsulation of the agent in the liposome occurs as described above.

Loading using a pH gradient may be carried out according to methods described in U.S. Pat. Nos. 5,616,341, 5,736,155 and 5,785,987 incorporated herein by reference. A preferred method of pH gradient loading is the citrate-based loading method utilizing citrate as the internal buffer at a pH of 2-6 and a neutral external buffer.

Various methods may be employed to establish and maintain a pH gradient across a liposome all of which are incorporated herein by reference. This may involve the use of ionophores that can insert into the liposome membrane and transport ions across membranes in exchange for protons (see for example U.S. Pat. No. 5,837,282). Compounds encapsulated in the interior of the liposome that are able to shuttle protons across the liposomal membrane and thus set up a pH gradient (see for example U.S. Pat. No. 5,837,282) may also be utilized. These compounds comprise an ionizable moiety that is neutral when deprotonated and charged when protonated. The neutral deprotonated form (which is in equilibrium with the protonated form) is able to cross the liposome membrane and thus leave a proton behind in the interior of the liposome and thereby cause an decrease in the pH of the interior. Examples of such compounds include methylammonium chloride, methylammonium sulfate, ethylenediammonium sulfate (see U.S. Pat. No. 5,785,987) and ammonium sulfate. Internal loading buffers that are able to establish a basic internal pH, can also be utilized. In this case, the neutral form is protonated such that protons are shuttled out of the liposome interior to establish a basic interior. An example of such a compound is calcium acetate (see U.S. Pat. No. 5,939,096).

Two or more agents may be loaded into a liposome using the same active loading methods or may involve the use of different active loading methods. For instance, metal complexation loading may be utilized to actively load multiple agents or may be coupled with another active loading technique, such as pH gradient loading. Metal-based active loading typically uses liposomes with passively encapsulated metal ions (with or without passively loaded therapeutic agents). Various salts of metal ions are used, presuming that the salt is pharmaceutically acceptable and soluble in an aqueous solutions. Actively loaded agents are selected based on being capable of forming a complex with a metal ion and thus being retained when so complexed within the liposome, yet capable of loading into a liposome when not complexed to metal ions. Agents that are capable of coordinating with a metal typically comprise coordination sites such as amines, carbonyl groups, ethers, ketones, acyl groups, acetylenes, olefins, thiols, hydroxyl or halide groups or other suitable groups capable of donating electrons to the metal ion thereby forming a complex with the metal ion. Examples of active agents which bind metals include, but are not limited to, quinolones such as fluoroquinolones; quinolones such as nalidixic acid; anthracyclines such as doxorubicin, daunorubicin and idarubicin; amino glycosides such as kanamycin; and other antibiotics such as bleomycin, mitomycin C and tetracycline; and nitrogen mustards such as cyclophosphamide, thiosemicarbazones, indomethacin and nitroprusside; camptothecins such as topotecan, irinotecan, lurtotecan, 9-aminocamptothecin, 9-nitrocamptothecin and 10-hydroxycamptothecin; and podophyllotoxins such as etoposide. Uptake of an agent may be established by incubation of the mixture at a suitable temperature after addition of the agent to the external medium. Depending on the composition of the liposome, temperature and pH of the internal medium, and chemical nature of the agent, uptake of the agent may occur over a time period of minutes or hours. Methods of determining whether coordination occurs between an agent and a metal within a liposome include spectrophotometric analysis and other conventional techniques well known to those of skill in the art.

Furthermore, liposome loading efficiency and retention properties using metal-based procedures carried out in the absence of an ionophore in the liposome are dependent on the metal employed and the lipid composition of the liposome. By selecting lipid composition and a metal, loading or retention properties can be tailored to achieve a desired loading or release of a selected agent from a liposome.

Passive and active loading methods may be combined sequentially in order to load multiple drugs into a delivery vehicle. By way of example, liposomes containing a passively entrapped platinum drug such as cisplatin in the presence of $MnCl_2$ may subsequently be used to actively encapsulate an anthracycline such as doxorubicin into the interior of the liposome. This method is likely to be applicable to numerous drugs that are encapsulated in liposomes through passive encapsulation.

Kits

The therapeutic agents in the invention compositions may be formulated separately in individual compositions wherein each therapeutic agent is stably associated with appropriate delivery vehicles. These compositions can be administered separately to subjects as long as the pharmacokinetics of the delivery vehicles are coordinated so that the ratio of therapeutic agents administered is maintained at the target for treatment. Thus, it is useful to construct kits which include, in separate containers, a first composition comprising delivery vehicles stably associated with at least a first therapeutic agent and, in a second container, a second composition comprising delivery vehicles stably associated with at least one second therapeutic agent. The containers can then be packaged into the kit.

The kit will also include instructions as to the mode of administration of the compositions to a subject, at least including a description of the ratio of amounts of each composition to be administered. Alternatively, or in addition, the kit is constructed so that the amounts of compositions in each container is pre-measured so that the contents of one container in combination with the contents of the other represent the correct ratio. Alternatively, or in addition, the containers may be marked with a measuring scale permitting dispensation of appropriate amounts according to the scales visible. The containers may themselves be useable in administration; for example, the kit might contain the appropriate amounts of each composition in separate syringes. Formulations which comprise the pre-formulated correct ratio of therapeutic agents may also be packaged in this way so that the formulation is administered directly from a syringe prepackaged in the kit.

Therapeutic Uses of Delivery Vehicle Compositions Encapsulating Multiple Agents

These delivery vehicle compositions may be used to treat a variety of diseases in warm-blooded animals and in avian species. Thus, suitable subjects for treatment according to the methods and compositions of the invention include humans, mammals such as livestock or domestic animals, domesticated avian subjects such as chickens and ducks, and laboratory animals for research use. Examples of medical uses of the compositions of the present invention include treating cancer, treating cardiovascular diseases such as hypertension, cardiac arrhythmia and restenosis, treating bacterial, viral, fungal or parasitic infections, treating and/or preventing diseases through the use of the compositions of the present inventions as vaccines, treating inflammation or treating autoimmune diseases.

In one embodiment, delivery vehicle compositions in accordance with this invention are preferably used to treat neoplasms. Delivery of formulated drug to a tumor site is achieved by administration of liposomes or other particulate delivery systems. Preferably liposomes have a diameter of less than 200 nm Tumor vasculature is generally leakier than normal vasculature due to fenestrations or gaps in the endothelia. This allows the delivery vehicles of 200 nm or less in diameter to penetrate the discontinuous endothelial cell layer and underlying basement membrane surrounding the vessels supplying blood to a tumor. Selective accumulation of the delivery vehicles into tumor sites following extravasation leads to enhanced drug delivery and therapeutic effectiveness. Because carriers extravasate, it can be assumed that the carrier drug-to-drug ratio determined in the blood will be comparable to the carrier drug-to-drug ratio in the extravascular space.

Administering Delivery Vehicle Compositions

As mentioned above, the delivery vehicle compositions of the present invention may be administered to warm-blooded animals, including humans as well as to domestic avian species. For treatment of human ailments, a qualified physician will determine how the compositions of the present invention should be utilized with respect to dose, schedule and route of administration using established protocols. Such applications may also utilize dose escalation should agents encapsulated in delivery vehicle compositions of the present invention exhibit reduced toxicity to healthy tissues of the subject.

Preferably, the pharmaceutical compositions of the present invention are administered parenterally, i.e., intraarterially, intravenously, intraperitoneally, subcutaneously, or intramuscularly. More preferably, the pharmaceutical compositions are administered intravenously or intraperitoneally by a bolus injection. For example, see Rahman, et al., U.S. Pat. No. 3,993,754; Sears, U.S. Pat. No. 4,145,410; Papahadjopoulos, et al., U.S. Pat. No. 4,235,871; Schneider, U.S. Pat. No. 4,224,179; Lenk, et al., U.S. Pat. No. 4,522,803; and Fountain, et al., U.S. Pat. No. 4,588,578.

In other methods, the pharmaceutical preparations of the present invention can be contacted with the target tissue by direct application of the preparation to the tissue. The application may be made by topical, "open" or "closed" procedures. By "topical", it is meant the direct application of the pharmaceutical preparation to a tissue exposed to the environment, such as the skin, oropharynx, external auditory canal, and the like. "Open" procedures are those procedures that include incising the skin of a patient and directly visualizing the underlying tissue to which the pharmaceutical preparations are applied. This is generally accomplished by a surgical procedure, such as a thoracotomy to access the lungs, abdominal laparotomy to access abdominal viscera, or other direct surgical approach to the target tissue. "Closed" procedures are invasive procedures in which the internal target tissues are not directly visualized, but accessed via inserting instruments through small wounds in the skin. For example, the preparations may be administered to the peritoneum by needle lavage. Likewise, the pharmaceutical preparations may be administered to the meninges or spinal cord by infusion during a lumbar puncture followed by appropriate positioning of the patient as commonly practiced for spinal anesthesia or metrazamide imaging of the spinal cord. Alternatively, the preparations may be administered through endoscopic devices.

Pharmaceutical compositions comprising delivery vehicles of the invention are prepared according to standard techniques and may comprise water, buffered water, 0.9% saline, 0.3% glycine, 5% dextrose and the like, including glycoproteins for enhanced stability, such as albumin, lipoprotein, globulin, and the like. These compositions may be sterilized by conventional, well-known sterilization techniques. The resulting aqueous solutions may be packaged for use or filtered under aseptic conditions and lyophilized, the lyophilized preparation being combined with a sterile aqueous solution prior to administration. The compositions may contain pharmaceutically acceptable auxiliary substances as required to approximate physiological conditions, such as pH adjusting and buffering agents, tonicity adjusting agents and the like, for example, sodium acetate, sodium lactate, sodium chloride, potassium chloride, calcium chloride, and the like. Additionally, the delivery vehicle suspension may include lipid-protective agents which protect lipids against free-radical and lipid-peroxidative damages on storage. Lipophilic free-radical quenchers, such as alpha-tocopherol and water-soluble iron-specific chelators, such as ferrioxamine, are suitable.

The concentration of delivery vehicles in the pharmaceutical formulations can vary widely, such as from less than about 0.05%, usually at or at least about 2-5% to as much as 10 to 30% by weight and will be selected primarily by fluid volumes, viscosities, and the like, in accordance with the particular mode of administration selected. For example, the concentration may be increased to lower the fluid load associated with treatment. Alternatively, delivery vehicles composed of irritating lipids may be diluted to low concentrations to lessen inflammation at the site of administration. For diagnosis, the amount of delivery vehicles administered will depend upon the particular label used, the disease state being diagnosed and the judgment of the clinician.

Preferably, the pharmaceutical compositions of the present invention are administered intravenously. Dosage for the delivery vehicle formulations will depend on the ratio of drug to lipid and the administrating physician's opinion based on age, weight, and condition of the patient.

In addition to pharmaceutical compositions, suitable formulations for veterinary use may be prepared and administered in a manner suitable to the subject. Preferred veterinary subjects include mammalian species, for example, non-human primates, dogs, cats, cattle, horses, sheep, and domesticated fowl. Subjects may also include laboratory animals, for example, in particular, rats, rabbits, mice, and guinea pigs.

In the instance where a single composition containing more than one active agent is included, the above procedures are followed per se. Where the agents are administered in separate delivery vehicle compositions, the administration should be timed in such a manner that the desired ratio is maintained. Typically, this can accomplished by simultaneously administering the compositions in the calculated proportions.

Evaluation of Therapeutic Activity In Vivo

Therapeutic activity of delivery vehicle compositions comprising two or more encapsulated agents may be measured after administration into an animal model. Preferably, the animal model comprises a tumor although delivery vehicle compositions may be administered to animal models of other diseases. Rodent species such as mice and rats of either inbred, outbred, or hybrid origin including immunocompetent and immunocompromised, as well as knockout, or transgenic models may be used.

Models can consist of solid or non-solid tumors implanted as cell suspensions, bries or tumor fragments in either subcutaneous, intravenous, intraperitoneal, intramuscular, intrathecal, or orthotopic regions. Tumors may also be established via the application or administration of tumorigenic/carcinogenic agents or may be allowed to arise spontaneously in appropriate genetically engineered animal models. Tumor types can consist of tumors of ectodermal, mesodermal, or endodermal origin such as carcinomas, sarcomas, melanomas, gliomas, leukemias and lymphomas.

In a preferred embodiment, mouse models of tumors are employed. Human xenograft solid tumors grown in immune compromised mice may be utilized and selected on the basis of defined genetics and growth attributes. Tumor cells utilized in these experiments can be genetically manipulated or selected to express preferable properties and are injected into mice.

Once the tumors have grown to a palpable (measurable) size, delivery vehicle compositions can be administered, preferably intravenously, and their effects on tumor growth are monitored. Intended therapeutic treatments can consist of single bolus or push administrations or multiple or continuous administrations over several days or weeks and by any appropriate route such as by the oral, nasal, subcutaneous, intravenous, intraperitoneal, intrathecal, intratumoral routes using syringes, tablets, liquids, and pumps (such as osmotic). Dose and schedule dependency may be evaluated in order to determine the maximum anti-tumor activity that can be achieved.

Various methods of determining therapeutic activity in animal models comprising a tumor may be utilized. This includes solid tumor model evaluation methods and non-solid tumor model evaluation methods.

Solid tumor model evaluation methods include measurement of tumor volume (mass), tumor weight inhibition (TWI %), tumor growth delay (T-C), tumor regression, cell kill and clonogenic assays.

Tumor volume measurements are determined from vernier caliper measurements of perpendicular length and width measurements (height measurements can often be obtained as well). Tumor volume (mL) or mass (g) is calculated from: volume=(length×width$^2$/2; or volume=n/π/6×(length×width×height). Data is plotted with respect to time.

Tumor weight inhibition (TWI %) is determined by measuring the mean tumor weight of a treated group divided by the mean tumor weight of a control group, minus 1×100 at a defined time point.

Tumor growth delay (T-C) is measured as the median time in days for a treated group (T) to reach an arbitrarily determined tumor size (for example, 300 mg) minus median time in days for the control group to reach the same tumor size.

Tumor regression as a result of treatment may also be used as a means of evaluating a tumor model. Results are expressed as reductions in tumor size (mass) over time.

Cell kill methods of solid tumor model evaluation can involve measuring tumors repeatedly by calipers until all exceed a predetermined size (e.g., 200 mg). The tumor growth and tumor doubling time can then be evaluated. $Log_{10}$ cell kill parameters can be calculated by:

$$\log_{10} \text{ cell kill/dose}=(T-C)/((3.32)(T_d)(\text{No. of doses}))$$

$$\log_{10} \text{ cell kill (total)}=(T-C)/((3.32)(T_d))$$

$$\log_{10} \text{ cell kill (net)}=((T-C)-(\text{duration of } R_x))/((3.3(T_d))$$

Where: (T−C)=tumor growth delay $T_d$=Tumor doubling time

Clonogenicity assays express the effectiveness of therapy. These assays include excision assays and characterization of cell suspensions from solid tumors.

Excision assays, used to assess what fraction of cells, in a suspension prepared from tumors, have unlimited proliferative potential (i.e., are clonogenic). Three types of excision assays are:

i) $TD_{50}$, or endpoint dilution assays: determines the number of cells required to produce tumor takes from inocula in vivo.

ii) In vivo colony assay: assesses the ability of individual cells to form nodules (colonies) in, for example, the lung.

iii) In vitro colony assay, tests the ability of individual cells to grow into colonies either in liquid media, when colonies form on the plastic or glass surface of culture dishes, or in semisolid media such as agar, in which the colonies form in suspension.

Characterization of cell suspensions from solid tumors are required for in vitro and in vivo clonogenic assays, flow-cytometric measurements, and for numerous biochemical and molecular analyses performed on a per cell basis. Preparation is by a number of methods such as enzymatic, mechanical, chemical, combinations thereof, and surface activity agents. Evaluations could include, cell yield, cell morphology, tumor cell clonogenicity, retention of biochemical or molecular characteristics.

Non-solid tumor model evaluation methods include measurement of increase in life span (ILS %), tumor growth delay (T-C), long-term survivors (cures).

Increase in life-span (ILS %) measures the percentage increase in life-span of treated groups versus control or untreated groups. Tumor growth delay (T-C) measures median time in days for treated (T) group survival minus median time in days for control (C) group survival. Long-term survivors (cures) measures treatment groups that survive up to and beyond 3-times the survival times of untreated or control groups.

Methods of determining therapeutic activity in humans afflicted with cancer include measurements of survival and surrogate endpoints. The time at which survival is reasonably evaluated depends on the tumor in question. By way of example, survival rates for patients with low-grade lymphomas may be examined at 5 or 10 years post diagnosis, whereas the survival or patients having aggressive diseases such as advanced non-small cell lung cancer may be best evaluated at 6 or 12 months post diagnosis.

Methods of determining therapeutic activity using surrogate endpoints includes measuring complete response (CR), partial response (PR), progression-free survival (PFS), time-to-progression (TTP) or duration of response (DOR), plasma and urine markers, enzyme inhibition and/or receptor status, changes in gene expression and quality of life (QOL).

A complete response means the disappearance of all known sites of disease without the development of any new disease for a period of time appropriate for the tumor type being treated. Assessments are based on a variety of examinations such as those stated above.

Partial response is at least a 50% decrease in the sum of the products of the bidimensional measurement of all lesions with no new disease appearing for a period of time appropriate for the tumor type being treated. Assessments are based on a variety of examinations (CT scan, MRI, ultrasound, PET scan, bone scan, physical examination) of patients.

Progression-free Survival (PFS): Duration from treatment in which a patient survives and there is no growth of existing tumor nor appearance of new tumor masses. PFS may be expressed as either the duration of time or as the proportion of patients who are surviving and progression-free at a given time after diagnosis.

Time-to-progression (TTP) or duration of response (DOR) refer to the duration of time from treatment to a progression of tumor growth, measured either as an increase in size of existing tumor masses or the appearance of new tumor masses.

Plasma and urine markers include measuring markers such as, but not limited to, the following markers: prostate specific antigen (PSA) and carcinoembryonic antigen (CEA).

Enzyme inhibition and/or receptor status. Growth factor receptors such as, but not limited to, tyrosine kinase receptors, EGF receptor, PDGF receptor, Her-1 and Her-2 receptors. Enzymes such as, but not limited to, integrin-linked kinases, protein kinases and the like.

Changes in gene expression include serial analysis of gene expression (genomics) and changes in protein expression (proteomics).

Quality of Life (QOL) include methods such as the EORTC QLQ-C30 scoring method that evaluates yields scores for five functional scales (physical, role, cognitive, social, and emotional), three symptom scales (nausea, pain, and fatigue), and a global health and quality of life scale. The measure also yields single-item ratings of additional symptoms commonly reported by cancer patients (dyspnea, appetite loss, sleep disturbance, constipation, and diarrhea) as well as the perceived financial impact of the disease and its treatment.

The following examples are given for the purpose of illustration and are not by way of limitation on the scope of the invention.

EXAMPLES

The examples below employ the following methods of determining cytotoxicity and for evaluating non-antagonistic effects.

Cytotoxicity Assay

In the following examples the standard tetrazolium-based colorimetric MTT cytotoxicity assay protocol (Mosmann, et al., *J. Immunol Methods* (1983) 65(1-2):55-63) was utilized to determine the readout for the fraction of cells affected. Briefly, viable cells reduce the tetrazolium salt, 3-(4,5-diethylthiazoyl-2-yl)-2,5-diphenyltetrazolium bromide (MTT) to a blue formazan which can be read spectrophotometrically. Cells, such as human H460 non-small-cell lung carcinoma (NSCLC) cells grown in 25 $cm^2$ flasks are passaged (passage number<20), resuspended in fresh RPMI cell culture medium and added into 96-well cell culture plates at a concentration of 1000 cells per well in 100 μL per well. The cells are then allowed to incubate for 24 hours at 37° C., 5% $CO_2$. The following day, serial drug dilutions are prepared in 12-well cell culture plates. The agents, previously prepared in various solutions, are diluted in fresh RPMI cell culture media. Agents are administered to the appropriate or specified wells for single agents (20 μL) and at specific fixed ratio dual agent combinations (increments of 20 μL) using a Latin square design or "checkerboard" dilution method. The total well volumes are made up to 200 μL with fresh media. The drug exposure is for a duration of 72 hours.

Following drug exposure, MTT reagent (1 mg/mL in RPMI) is added to each well at a volume of 50 μL per well and incubated for 3-4 hours. The well contents are then aspirated and 150 μL of dimethylsulfoxide (DMSO) is added to each well to disrupt the cells and to solubilize the formazan precipitate within the cells. The 96-well plates are shaken on a plate shaker, and read on a microplate spectrophotometer set at a wavelength of 570 nm. The optical density (OD) readings are recorded and the OD values of the blank wells (containing media alone) are subtracted from all the wells containing cells. The cell survival following exposure to agents is based as a percentage of the control wells (cells not exposed to drug). All wells are performed in triplicate and mean values are calculated.

Median-Effect Analysis for Drug Combinations

For the drug combination analysis, the software program CalcuSyn, (Biosoft, Ferguson, Mo., USA) based on the median-effect principle by Chou and Talalay, was utilized. The fixed ratios for the dual-agent combinations are initially derived from the $IC_{50}:IC_{50}$ ratios from single agent cytotoxicity profiles. Subsequently, more relevant fixed ratios (e.g. ranging from 10:1 to 1:10; mole ratios) are chosen based upon considerations for formulation purposes. From the mean values calculated based on agent effects on cell survival, doses and respective fractional effect values are entered into the CalcuSyn computer program. The software then determines whether the drug combinations are synergistic, additive or antagonistic based on combination index (CI) values.

Example 1

Multiple Representation of Dose-Effect Analysis

Quantitative analysis of the relationship between an amount (dose or concentration) of drug and its biological effect as well as the joint effect of drug combinations can be measured and reported in a number of ways. FIG. 2 illustrates 5 such methods using, as an example, a combination of irinotecan and carboplatin.

Based on Chou and Talalay's theory of dose-effect analysis, a "median-effect equation" has been used to calculate a number of biochemical equations that are extensively used in the art. Derivations of this equation have given rise to higher order equations such as those used to calculate Combination Index (CI). As mentioned previously, CI can be used to determine if combinations of more than one drug and various ratios of each combination are antagonistic, additive or synergistic. CI plots are typically illustrated with CI representing the y-axis versus the proportion of cells affected, or fraction affected ($f_a$), on the x-axis. FIG. 2A demonstrates that a 1:10 mole ratio of irinotecan/carboplatin is antagonistic (CI>1.1), while 1:1 and 10:1 have a synergistic effect (CI<0.9).

The present applicants have also designed an alternative method of representing the dependency of CI on the drug ratios used. The maximum CI value is plotted against each ratio to better illustrate trends in ratio-specific effects for a particular combination as seen in FIG. 2B. The CI maximum is the CI value taken at a single $f_a$ value (between 0.2 and 0.8) where the greatest difference in CI values for the drugs at different ratios was observed.

Figure 2C:
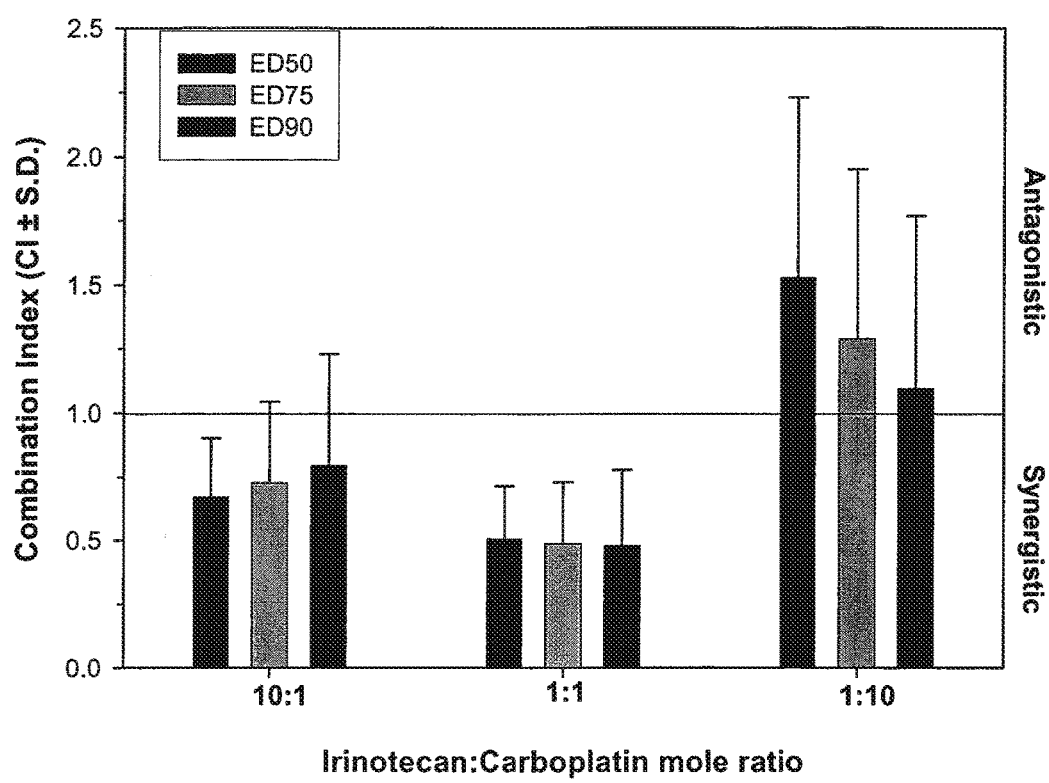

Because the concentrations of drugs used for an individual ratio play a role in determining the effect (i.e., synergism or antagonism), it can also be important to measure the CI at various concentrations. These concentrations, also referred to as "Effective Doses" (ED) by Chou-Talalay, are the concentration of drug required to affect a designated percent of the cells in an in vitro assay, i.e., $ED_{50}$ is the concentration of drug required to affect 50% of the cells relative to a control or untreated cell population. As shown in FIG. 2C, trends in concentration-effect are readily distinguished between the various ratios. The error bars shown represent one standard deviation around the mean and is determined directly through the CalcuSyn program.

Figure 2D:
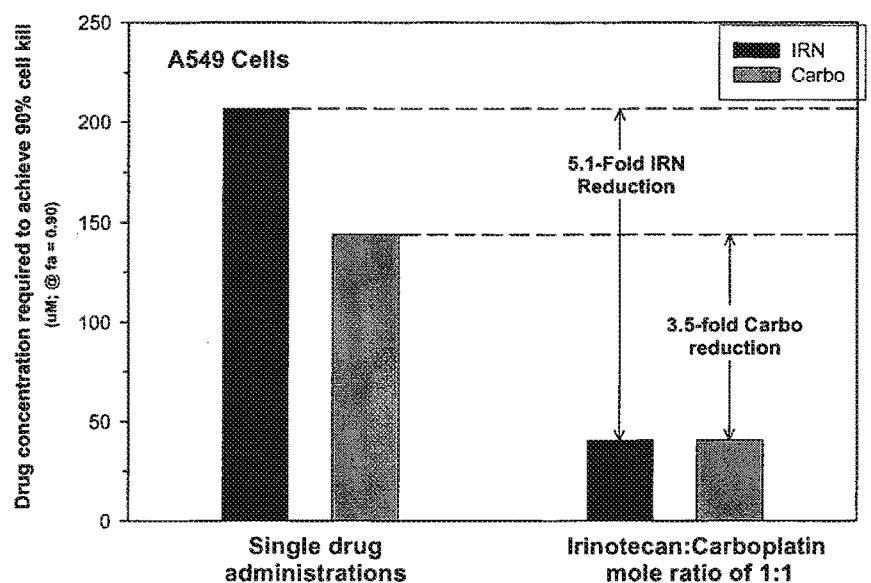

A synergistic interaction between two or more drugs has the benefit that it can lower the amount of each drug required in order to result in a positive effect, otherwise known as "dose-reduction." Chou and Talalay's "dose-reduction index" (DRI) is a measure of how much the dose of each drug in a synergistic combination may be reduced at a given effect level compared with the doses for each drug alone. DRI has been important in clinical situations, where dose-reduction leads to reduced toxicity for the host while maintaining therapeutic efficacy. The plot in FIG. 2D shows that the concentrations of irinotecan and carboplatin required to achieve a 90% cell kill on their own is significantly higher than their individual concentrations required when they are combined at a non-antagonistic ratio.

Figure 2E:
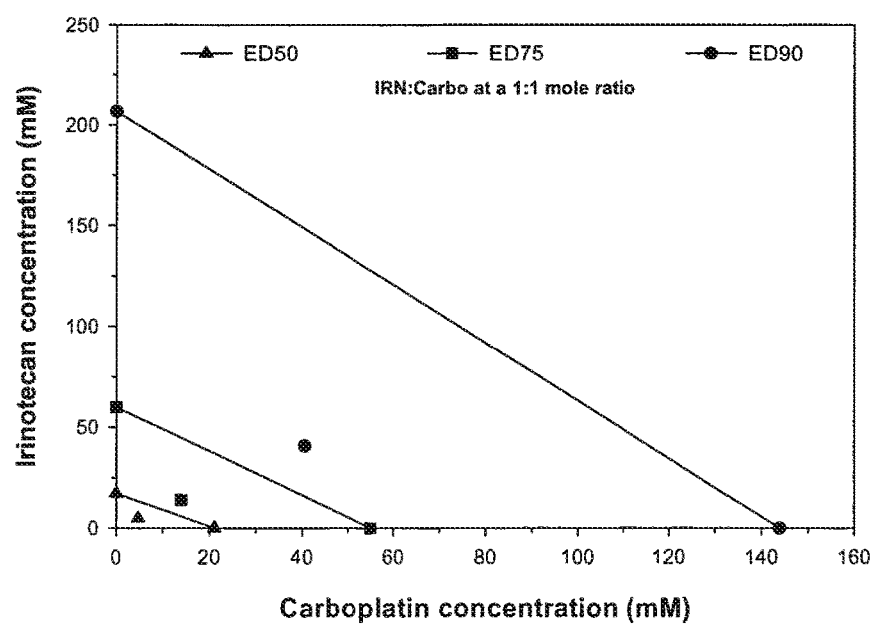

Furthermore the aforementioned data can be represented in a classical isobologram (FIG. 2E). Isobolograms have the benefit that they can be generated at different ED values; however, they become more difficult to read as more effect levels are selected for interpretation. For this reason, the data in the examples below are generally presented in accordance with the types of plots shown in FIGS. 2A and 2B.

Example 2

CI is Dependent Upon Concentrations

Drug combinations of irinotecan and 5-Fluorouracil (5-FU) at mole ratios of 1:1 and 1:10 and etoposide and carboplatin at mole ratios of 10:1 and 1:10 were tested for additive, synergistic or antagonistic effects using the standard tetrazolium-based colorimetric MTT cytotoxicity assay and the median-effect analysis as described in the previous example sections. HT29 or MCF-7 cells were exposed to single agents as well as agents in combination at defined ratios. Eight drug concentrations were utilized for single agents and combinations. Optical density values were obtained from the MTT assay, converted into a percentage of the control, averaged and then converted into fraction affected values. Dose and fraction affected values were entered into CalcuSyn which yielded the CI versus $f_a$ graph, shown in FIG. 3.

Figure 3A:
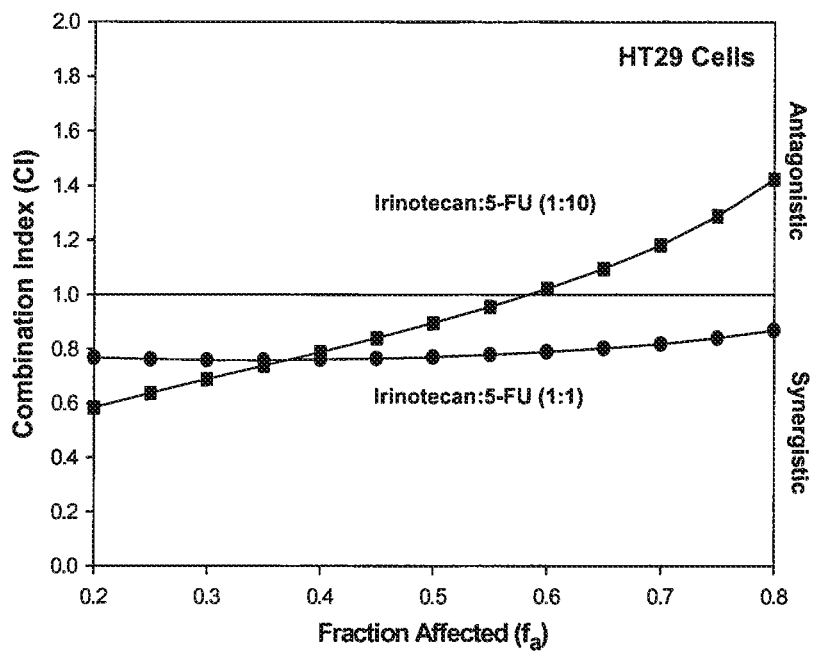
FIG. 3A is a graph of combination index (CI) for irinotecan:5-FU at mole ratios of 1:10 (filled squares) and 1:1 (filled circles) as a function of the fraction of HT29 cells affected ($f_a$).
Figure 3B:
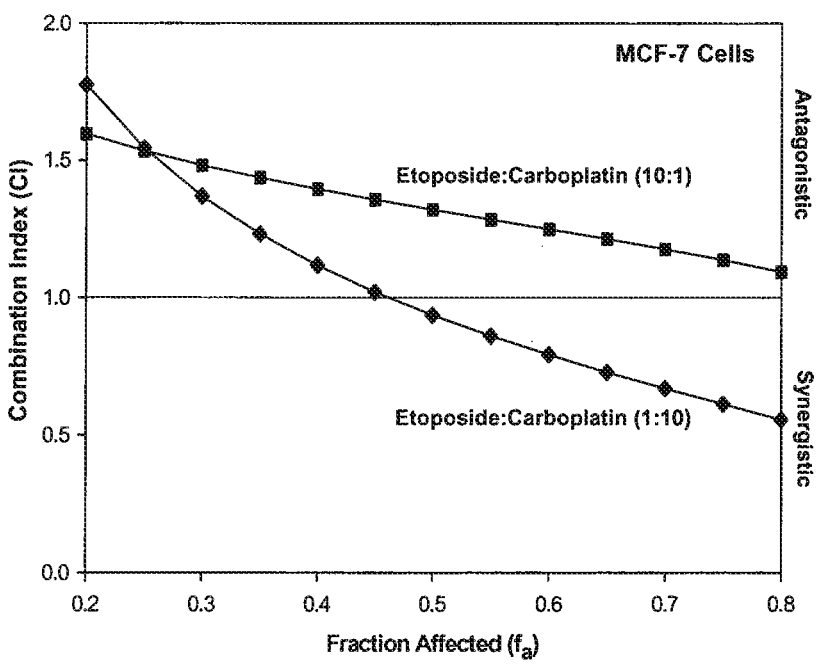
FIG. 3B is a graph of CI for etoposide:carboplatin at mole ratios of 1:10 (filled diamonds) and 10:1 (filled squares) as a function of the fraction of MCF-7 cells affected ($f_a$).

FIG. 3A shows that irinotecan and 5-FU at a mole ratio of 1:1 were non-antagonistic over the entire range of concentrations as measured by the fraction-affected dose. In contrast, at a mole ratio of 1:10, the same two drugs were non-antagonistic at low concentrations, yet antagonistic at higher concentrations. As seen in FIG. 3B, etoposide and carboplatin were antagonistic at a mole ratio of 10:1 over the entire concentration range. In contrast, at a 1:10 mole ratio, etoposide and carboplatin were antagonistic at low concentrations while non-antagonistic at higher concentrations.

Figure 4:
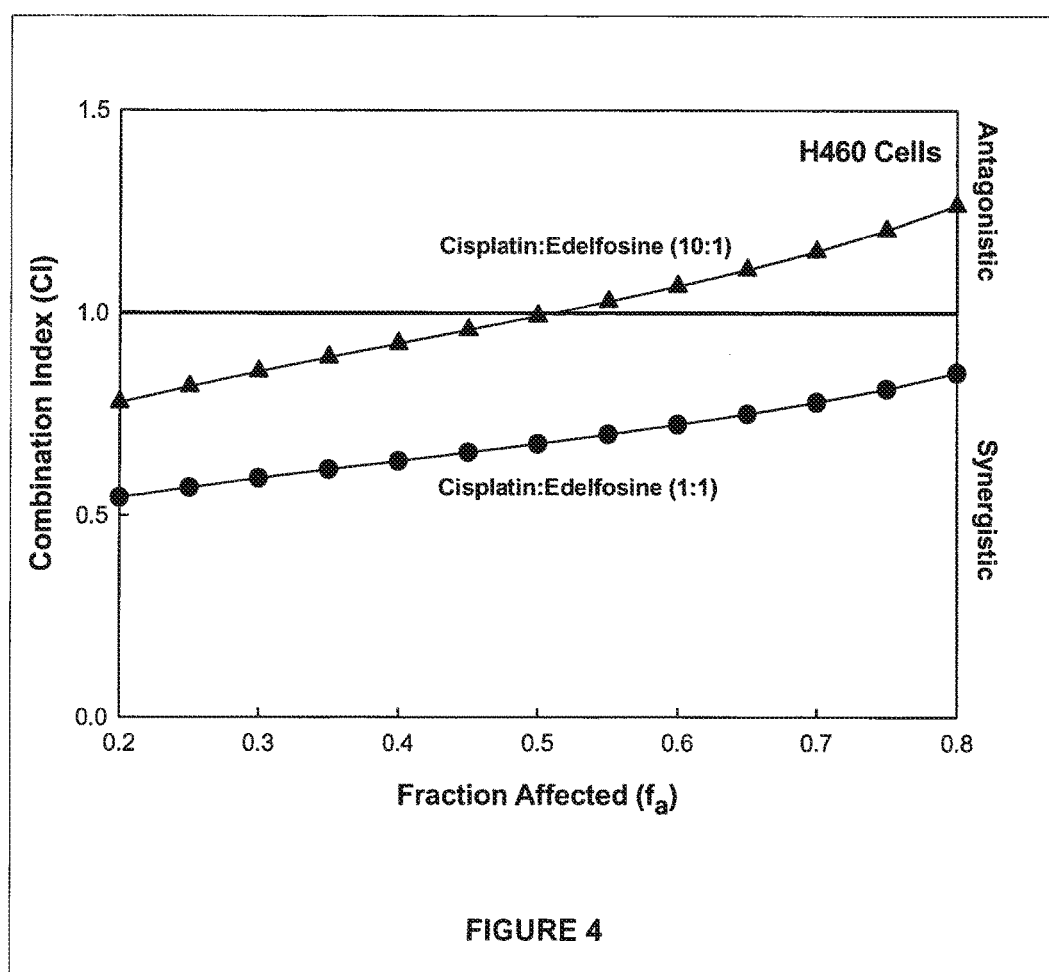
FIG. 4 is a graph of the CI for cisplatin:edelfosine at mole ratios of 10:1 (filled triangles) and 1:1 (filled circles) as a function of the fraction of H460 cells affected ($f_a$).

Cisplatin and edelfosine at mole ratios of 10:1 and 1:1 were also shown to exhibit distinct combination effects in H460 cells as summarized by plotting CI versus $f_a$. As shown in FIG. 4, the combination at a 10:1 mole ratio was non-antagonistic for approximately 50% of the fraction affected range at low concentrations and antagonistic at higher concentrations, while a 1:1 mole ratio demonstrated synergy over the entire concentration range.

These results thus demonstrate that synergy is highly dependent on not only the ratio of the agents to one another but also their concentrations.

Example 3

Determination of CI for Various Two-Drug Combinations

Various drug combinations presented in the table below were tested for additive, synergistic or antagonistic effects using the MTT cytotoxicity assay protocol and the median-effect analysis procedure described above. Results from the CI versus $f_a$ graphs are tabulated below. The approximate percentage of the $f_a$ range that exhibited a non-antagonistic effect is reported in brackets following the ratio. Measurements were taken between $f_a$ values of 0.2 and 0.8 and the percent of that $f_a$ range exhibiting a synergistic or additive effect (non-antagonistic) was calculated by determining the percentage of the curve falling below a CI value of 1.1. Data is derived from at least one experiment performed in triplicate.

Figure 5A:
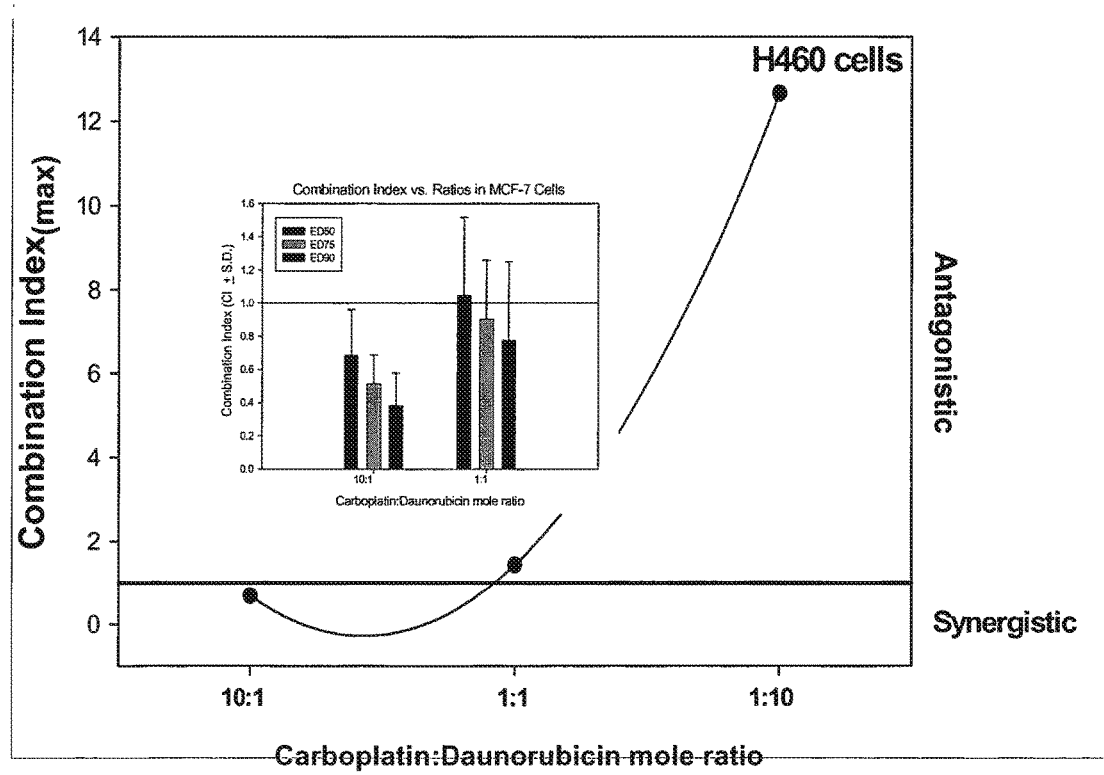
FIG. 5A is a graph of the CI maximum as a function of carboplatin:daunorubicin at 10:1, 1:1 and 1:10 mole ratios in H460 cells. The inset is a histogram of the CI for carboplatin:daunorubicin at mole ratios of 10:1 and 1:1 at Effective Dose (ED) values of 50, 75 and 90 in MCF-7 cells.

Standard deviations were calculated by the CalcuSyn program. As shown in the inset of FIG. 5A, carboplatin and daunorubicin at a mole ratio of 10:1 displays a synergistic interaction at ED50, ED75 and ED90 values in MCF-7 cells. As further shown in the inset of FIG. 5A, carboplatin and daunorubicin at a 1:1 mole ratio is synergistic, as judged by the mean CI values at ED75 and ED90 while being additive at ED50. In H460 cells, a plot of the CI maximum versus mole ratio of carboplatin/daunorubicin reveals that at a mole ratio of 10:1, the drugs are synergistic while at a mole ratio of 1:1, a slightly antagonistic effect is observed. In contrast, a strongly antagonistic effect is exhibited at a ratio of 1:10 (FIG. 5A). Data have also been plotted in FIG. 5B as CI versus the fraction of H460 cells affected to better illustrate the effect of concentration on synergy. A 1:1 mole ratio of carboplatin/daunorubicin is non-antagonistic at fraction affected values up to 0.42. At a ratio of 10:1, synergy is observed over a substantial range of $f_a$ values (greater than

| DRUG COMBINATION | CELL LINE | MOLE RATIO [% Synergistic or Additive[a]] |
|---|---|---|
| Irinotecan:5-FU | H460 | 1:10 [83%], 1:1 [17%], 10:1 [100%] |
| Irinotecan:5-FU | MCF-7 | 1:10 [48% additive[b]], 1:1 [58%], 10:1 [90%] |
| Irinotecan:5-FU | HT29 | 1:10 [75%], 1:1 [100%] |
| FUDR:Irinotecan | HCT-116 | 1:10 [0%], 1:5 [92%], 1:1 [100%], 5:1 [100%], 10:1 [100%] |
| FUDR:Irinotecan | HT29 | 1:10 [40%], 1:5 [73%], 1:1 [100%], 5:1 [100%], 10:1 [95%] |
| 5-FU:Carboplatin | H460 | 1:10 [48%], 1:1 [100%], 10:1 [100%] |
| FUDR:Carboplatin | H460 | 1:10 [37%], 1:5 [100%], 1:1 [100%], 5:1 [100% additive[b]], 10:1 [100% additive[b]] |
| Irinotecan:Carboplatin | H460 | 1:10 [0%], 1:1 [13%], 10:1 [100% additive[b]] |
| Irinotecan:Carboplatin | A549 | 1:10 [0%], 1:1 [100%], 10:1 [100%] |
| Cisplatin:Irinotecan | H460 | 1:10 [100%], 1:1 [56%], 10:1 [100% additive[b]] |
| Cisplatin:Irinotecan | MCF-7 | 1:10 [100%], 1:1 [92%], 10:1 [50%] |
| Etoposide:Carboplatin | H460 | 1:10 [55%], 1:1 [76% additive[b]], 10:1 [0%] |
| Etoposide:Carboplatin | MCF-7 | 1:10 [65%], 1:1 [30%], 10:1 [0%] |
| Carboplatin:Taxol | H460 | 1:10 [100%], 1:1 [100%], 1:100 [0%] |
| Carboplatin:Taxol | MCF-7 | 1:10 [100%], 1:1 [43%], 1:100 [0%] |
| Taxol:Doxorubicin | H460 | 1:5 [52%], 1:1 [37% additive[b]], 1:10 [22%] |
| Taxol:Doxorubicin | MCF-7 | 1:5 [70%], 1:1 [100%], 1:10 [63%] |
| Camptothecin:Taxol | H460 | 1:1 [0%], 1:10 [100%] |
| Doxorubicin:Vinorelbine | H460 | 20:1 [0%], 1:1 [100%] |
| Cisplatin:Etoposide | H460 | 50:1 [0%], 1:1 [100%] |
| Cisplatin:Etoposide | MCF-7 | 25:1 [0%], 1:1 [100%] |
| Suramin:Vinorelbine | H460 | 10:1 [0%], 20,000:1 [72%] |
| Cisplatin:Edelfosine | H460 | 10:1 [72%], 1:1 [100%] |
| Cisplatin:Safingol | H460 | 1:1 [0%], 0.1:1 [100%] |
| Cisplatin:Safingol | MCF-7 | 1:1 [58%], 0.1:1 [100%] |
| Cisplatin:β-sitosterol | H460 | 10:1 [0%], 0.1:1 [100%] |
| Cisplatin:β-sitosterol | MCF-7 | 10:1 [34%], 0.1:1 [100%] |
| Cisplatin:Suramin | H460 | 1:100 [37%], 1:40 [0%] |
| Vinorelbine:Cisplatin | H460 | 1:500 [0%], 1:200 [8% additive[b]] |
| Vinorelbine:Edelfosine | H460 | 1:10 [0%], 1:1 [0%] |
| Doxorubicin:Cytosine Arabinoside | H460 | 1:0.45 [0%] |
| Doxorubicin:Methotrexate | H460 | 1:0.36 [0%] |

[a] "% Synergistic or Additive" is calculated as the percent of the $f_a$ range that does not fall in the antagonistic range (CI values >1.1 are antagonistic) on a CI vs. fraction affected ($f_a$) plot, based on the Chou-Talalay Method, between $f_a$ values of 0.2 to 0.8. CI was measured by entering dose and $f_a$ values into CalcuSyn.
[b] The data set for this ratio was in the "additive" range (CI between 0.9 and 1.1).

Example 4

Synergism of Carboplatin and Daunorubicin

The procedure set forth above for measuring additive, synergistic or antagonistic effects was repeated using carboplatin/daunorubicin at 10:1, 1:1 and 1:10 mole ratios in H460 cells and at 10:1 and 1:1 ratios in MCF-7 cells. A combination index was determined for each dose by producing CI versus $f_a$ curves as described above and then determining the CI at $f_a$ values of 0.50, 0.75 and 0.90 (to yield CI values at ED50, ED75 and ED90, respectively).

Figure 5B:
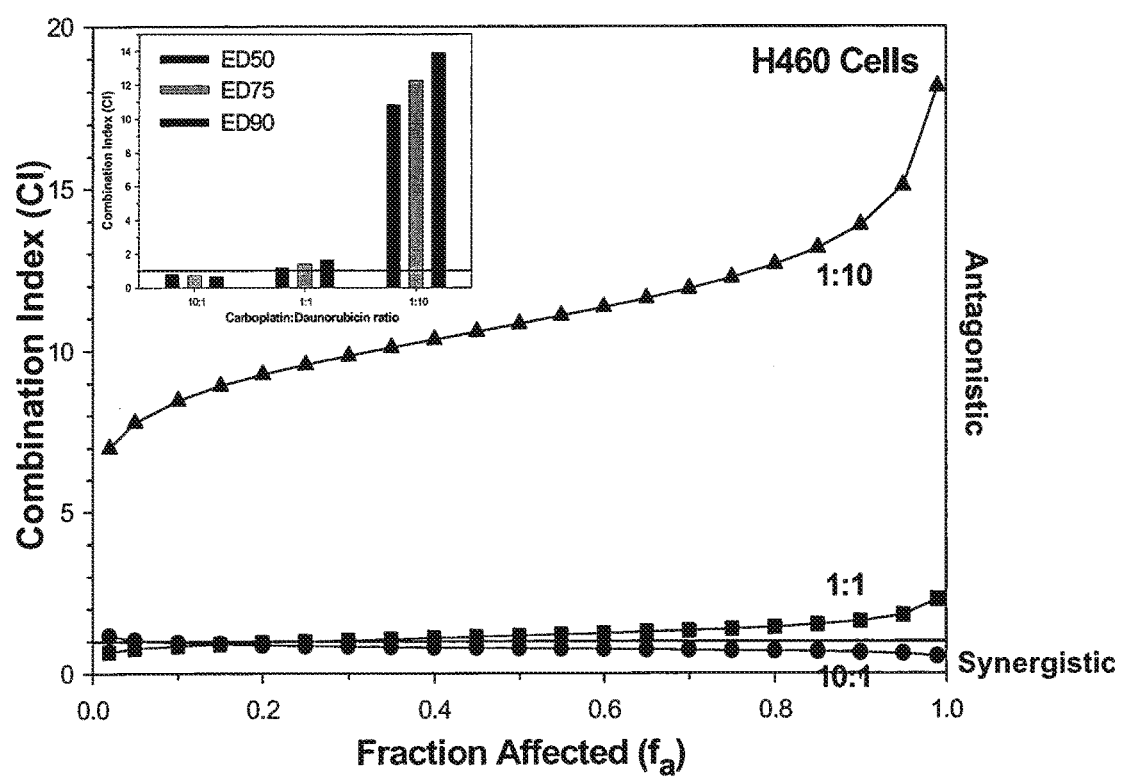
FIG. 5B is a graph of the CI for carboplatin:daunorubicin at mole ratios of 1:10 (filled triangles), 1:1 (filled squares) and 10:1 (filled circles) as a function of the fraction of H460 cells affected ($f_a$). The inset is a histogram of the CI for carboplatin:daunorubicin at mole ratios of 1:10, 1:1 and 10:1 at ED values of 50, 75 and 90 in H460 cells.

0.2) and a 1:10 ratio is antagonistic at all $f_a$ values. The inset of FIG. 5B shows that at a 10:1 ratio in H460 cells, synergy (as judged by the mean CI values) is observed at ED50, 75 and 90 and at a 1:1 ratio, additivity is indicated at the ED50. At a 1:10 ratio, carboplatin/daunorubicin is strongly antagonistic at ED50, 75 and 90 values. Based on these results, carboplatin and daunorubicin at a 1:10 mole ratio would therefore not be selected for further formulation and in vivo studies, as antagonism is observed at all ED values measured and over the full $f_a$ range in the CI versus $f_a$ plots. Mole ratios of 10:1 and 1:1 carboplatin:daunorubicin are selected for formulation and efficacy studies as at each of these ratios, the drugs demonstrate synergistic effects over at least 5% of the $f_a$ range (where greater than 1% of the cells are affected).

Example 5

Maintaining Synergism of Carboplatin and Daunorubicin In Vivo

Carboplatin and daunorubicin were co-loaded into a single cholesterol-free liposome at mole ratios of 10:1, 5:1 and 1:1 (carboplatin/daunorubicin). DSPC was dissolved in chloroform and DSPG was dissolved in chloroform/methanol/water (50:10:1 vol/vol) with trace amounts of $^{14}$C-CHE. The solutions were combined at a mole ratio of 80:20 (DSPC/DSPG). Solvent was removed under a stream of $N_2$ gas while maintaining the temperature at greater than 60° C. The lipid film was then placed in a vacuum pump for 2 minutes and subsequently redissolved in chloroform only. The chloroform was then removed as above. The resulting lipid films were left under vacuum overnight to remove any residual solvent followed by rehydration in 150 mM $CuSO_4$, pH 7.4 (pH adjusted with triethanolamine) containing 80 mg/mL carboplatin with 4% (v/v) DMSO to increase carboplatin solubility. The resulting multilamellar vesicles (MLVs) were extruded at 70° C. through two stacked 80 and 100 nm pore size filters for a total of ten passes. The samples were exchanged into saline and then into 300 mM sucrose, 20 mM HEPES, 30 mM EDTA, pH 7.4 (SHE) using tangential flow dialysis. Daunorubicin (with trace amounts of $^3$H-daunorubicin) was loaded into the liposomes by incubation at 60° C. for 5 minutes at drug to lipid ratios to achieve carboplatin/daunorubicin mole ratios of 10:1, 5:1 and 1:1. Subsequently, each sample was buffer exchanged into saline by tangential flow. To determine the extent of drug loading at various times, during preparation of the co-loaded formulation, daunorubicin and lipid levels were measured by liquid scintillation counting. Carboplatin concentrations were measured by atomic absorption spectrometry. Balb/c mice were intravenously administered 8 mg/kg carboplatin and daunorubicin was dosed at 1.2 mg/kg, 6 mg/kg and 12 mg/kg for mole ratios of 10:1, 5:1 and 1:1 carboplatin/daunorubicin, respectively in the co-loaded formulation. At the indicated time points (3 mice per time point), blood was collected by cardiac puncture and placed into EDTA coated microtainers. The samples were centrifuged and plasma was carefully transferred to another tube. Liquid scintillation counting was used to quantitate plasma daunorubicin and lipid levels; plasma carboplatin levels were determined by atomic absorption spectrometry. For quantitation by atomic absorption spectrometry, samples were diluted in 0.1% nitric acid to fall within the linear range of a standard curve.

Figure 6:
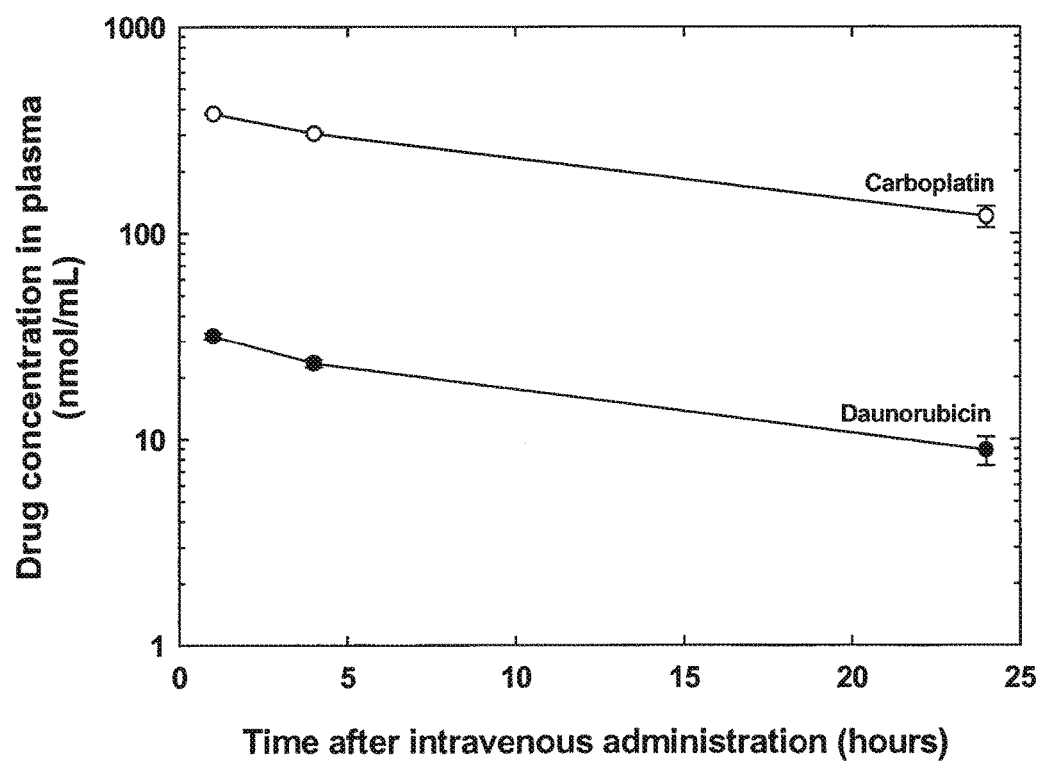
FIG. 6 is a graph of the carboplatin (open circles) and daunorubicin (filled circles) concentrations in plasma (nmoles/mL) as a function of time after intravenous administration when the drugs are formulated in a single liposome (DSPC/DSPG, 80:20 mol %) at a non-antagonistic ratio (10:1).
Figure 7A:
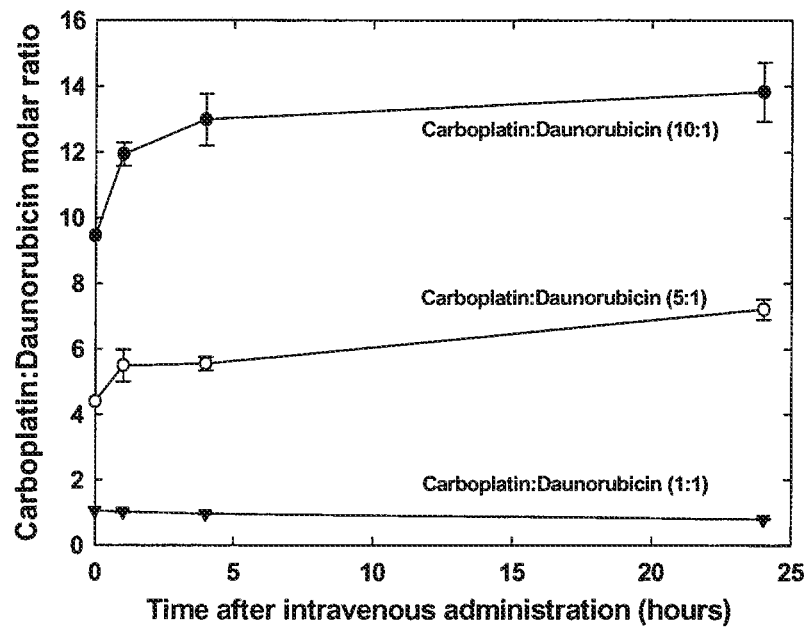
FIG. 7A is a graph of the carboplatin:daunorubicin mole ratio as a function of time after intravenous administration at three different ratios when the drugs are formulated in a single liposome (DSPC/DSPG, 80:20 mol %) at 10:1 (filled circles), 5:1 (open circles) and 1:1 (filled triangles).
Figure 7B:
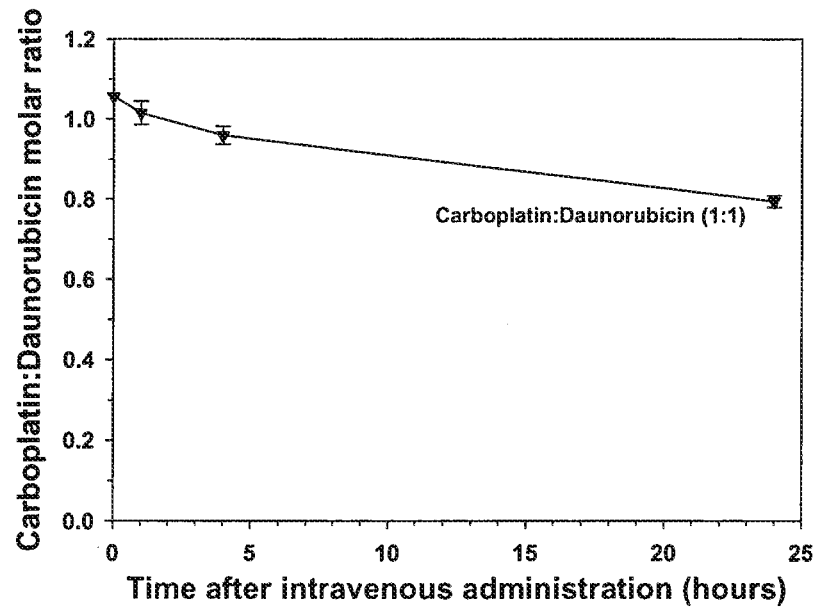
FIG. 7B is a graph of the 1:1 carboplatin:daunorubicin data in FIG. 7A re-plotted as a function of time after intravenous administration.

Results in FIG. 6, where the mean plasma drug concentration (+/−standard deviation, SD) is plotted at the specified times, indicate that the co-loaded liposomal formulations containing carboplatin and daunorubicin at a 10:1 mole ratio maintained the ratio of the drugs after intravenous administration as the mole plasma concentrations of carboplatin were present at ten times that of daunorubicin. Results in FIGS. 7A and 7B demonstrate that 10:1, 5:1 and 1:1 mole ratios of carboplatin to daunorubicin formulated in DSPC/DSPG liposomes were maintained in the blood compartment over the 24 hour time course (3 mice per time point) after intravenous administration of formulations prepared at these ratios (FIG. 7B more clearly highlights the results obtained following administration of the 1:1 carboplatin/daunorubicin formulation). These results thus demonstrate that coordinated release kinetics of two drugs at a variety of mole ratios can be achieved.

Carboplatin and daunorubicin were also co-formulated into DSPC/SM/DSPE-PEG2000 (90:5:5 mol %) liposomes in order to determine whether coordinated release of the drugs in vivo could be achieved using this formulation as well. A mole ratio of 10:1 was selected that was determined to be synergistic in Example 4.

Lipid films (with trace amounts of $^{14}$C-CHE) were prepared as described above by solubilizing the lipids in chloroform, removing the chloroform under $N_2$ gas and placing the samples in a vacuum pump overnight. The resulting lipid films were hydrated in 150 mM $CuSO_4$, 20 mM histidine, pH 7.4 (pH adjusted with triethanolamine) containing 40 mg/mL carboplatin. MLVs were extruded at 70° C. through two stacked filters of 100 nm pore sizes for a total of ten passes. Samples were then exchanged into 300 mM sucrose, 20 mM HEPES, pH 7.4 by tangential flow dialysis to remove unencapsulated metal solution (or carboplatin). Daunorubicin loading (with trace levels of $^3$H-daunorubicin) was carried out at 60° C. for 5 minutes at a drug concentration to achieve a 10:1 mole ratio of carboplatin/daunorubicin. To determine the extent of drug loading, daunorubicin and lipid levels were measured by liquid scintillation counting; carboplatin levels were determined by atomic absorption spectrometry. Male SCID/rag2 mice were administered 2.25 mg/kg daunorubicin and 15 mg/kg carboplatin intravenously of the combination co-loaded in DSPC/SM/DSPE-PEG2000 liposomes. At the indicated time points (3 mice per time point), blood was collected by cardiac puncture and placed into EDTA coated microtainers. The samples were centrifuged and plasma was carefully transferred to another tube. Plasma carboplatin and daunorubicin levels were determined by atomic absorption spectrometry and liquid scintillation counting, respectively.

Figure 8:
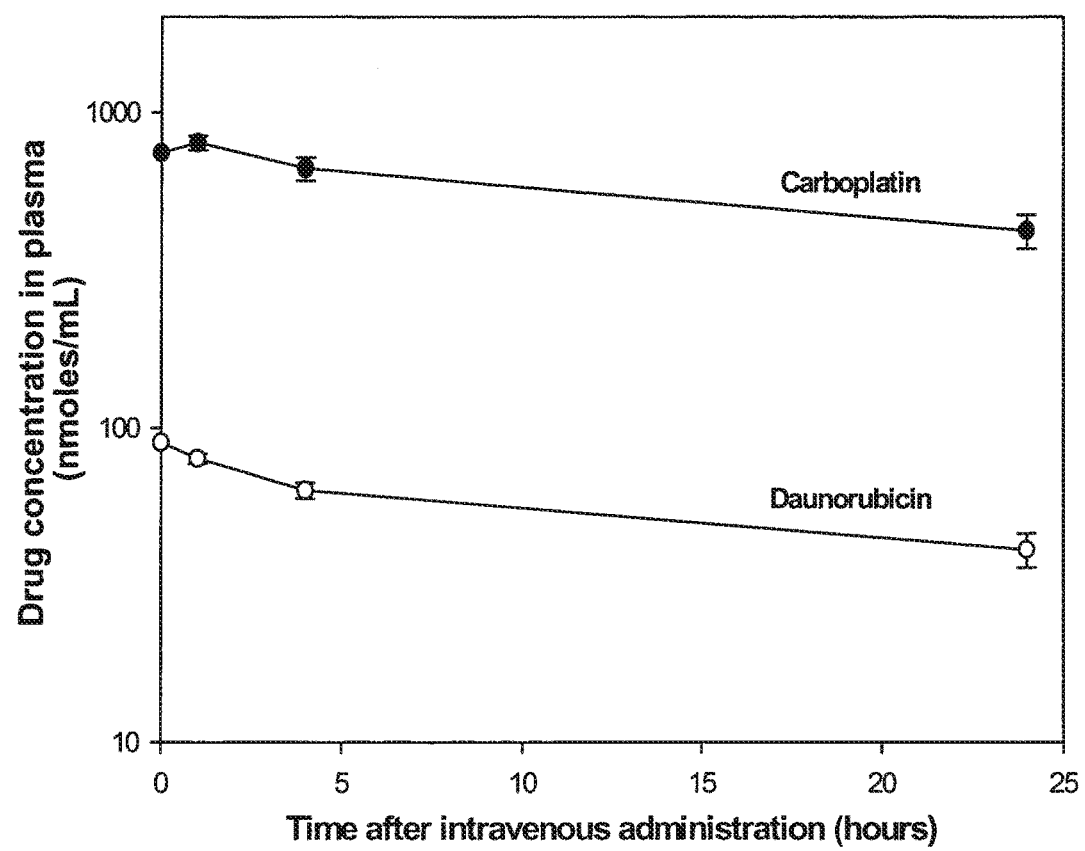
FIG. 8 is a graph of carboplatin (filled circles) and daunorubicin (open circles) concentrations in plasma (nmoles/mL) as a function of time after intravenous administration when the drugs are formulated at a non-antagonistic mole ratio (10:1) in a single liposome (DSPC/sphingomyelin/DSPE-PEG2000, 90:5:5 mol %).

The results set forth in FIG. 8, where the mean plasma drug concentration (+/−standard deviation, SD) is plotted at the indicated times, reveal that carboplatin and daunorubicin were eliminated from the plasma compartment at the same rate following intravenous administration when formulated in DSPC/SM/DSPE-PEG2000 liposomes. Carboplatin and daunorubicin were thus maintained at a 10:1 mole ratio, as the plasma concentration of carboplatin (nmoles/mL) was present at roughly ten times that of daunorubicin (nmoles/mL) during the time course. These results illustrate that a variety of formulations can be utilized to coordinate the pharmacokinetics of two drugs co-encapsulated in a single liposome such that similar pharmacokinetic release profiles are achieved.

Example 6

Efficacy of Liposomal Carboplatin and Daunorubicin

DSPC/DSPG liposomes (80:20 mol %) co-encapsulated with daunorubicin and carboplatin at a mole ratio of 1:1 (that was selected for formulation in Example 4) were prepared as described in Example 5 except lipid films were hydrated in a 150 mM $CuSO_4$, pH 7.4 (pH adjusted with triethanolamine), solution containing 25 mg/mL of carboplatin. As well, the lipid films were re-dissolved after being dried down in chloroform to remove methanol or water and then solvent was removed as described previously.

As in the method of Example 26, efficacy studies were carried out by first inoculating H460 cells ($1\times10^6$ cells)

subcutaneously into the flank of female SCID/rag2 mice. Tumors were allowed to grow until about 50 mg (0.05 cm³) in size at which time (day 12) the formulations were injected via the tail vein. Animals (4 mice per group) were treated with three injections, with injections being given every fourth day (q4d schedule; on days 12, 16 and 20). Tumor growth was determined by direct caliper measurements. Mice were treated with saline, free drug cocktail at a 1:1 mole ratio or a liposomal formulation of carboplatin/daunorubicin at a 1:1 mole ratio. For both the free and liposome-formulated treatments, the doses were 6.6 mg/kg carboplatin and 10 mg/kg daunorubicin. Lipid doses were 260 mg/kg lipid for liposome formulated samples.

Figure 9:
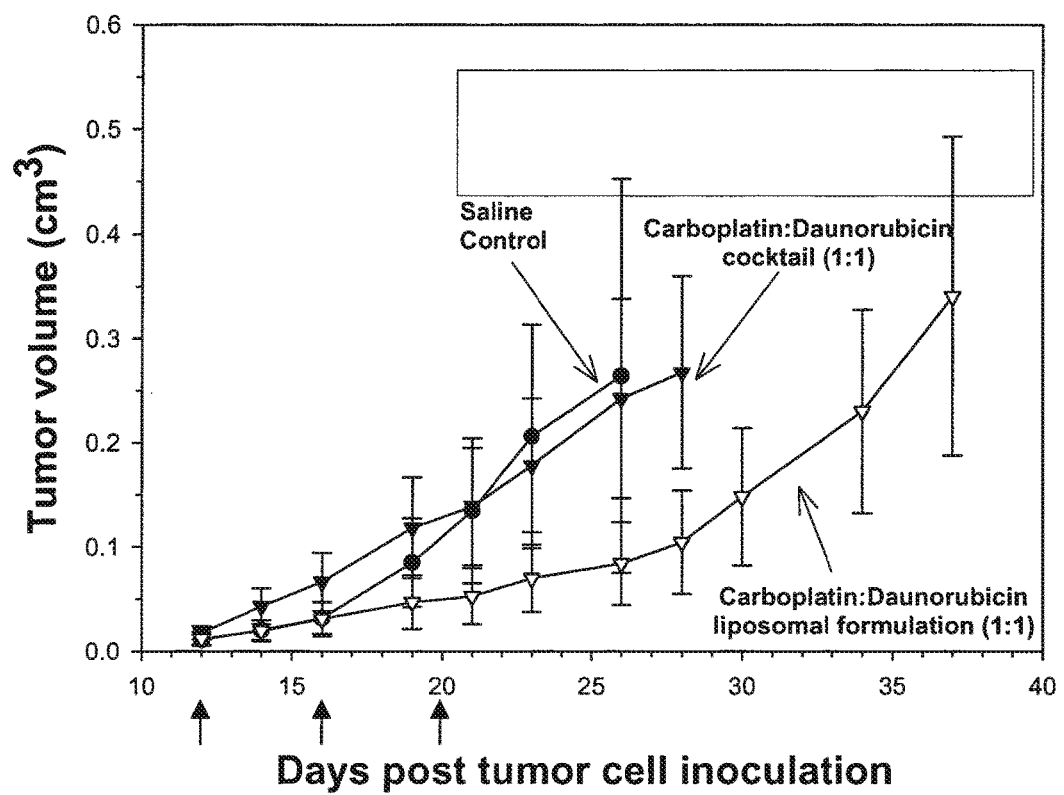
FIG. 9 is a graph comparing the activity of a cocktail of carboplatin and daunorubicin (filled inverted triangles), carboplatin and daunorubicin formulated in a single liposome (open inverted triangles) or saline control (filled circles) given to mice bearing the human H460 non-small cell lung tumor. Carboplatin and daunorubicin were formulated in DSPC/DSPG (80:20 mol %) liposomes at a 1:1 mole ratio. The arrows indicate the days at which the doses were administered.

Results presented in FIG. 9 (points represent mean tumor size+/−standard error of the mean (SEM) determined on the specified day) show that administration of liposomal carboplatin and daunorubicin at a 1:1 mole ratio increased efficacy in relation to free drug cocktail and saline controls.

Efficacy was also examined in sphingomyelin containing liposomes co-loaded with carboplatin and daunorubicin at a 10:1 mole ratio (determined to be synergistic in Example 4) to examine if the large improvements in efficacy observed for DSPC/DSPG liposomes could be achieved using this formulation as well. Carboplatin and daunorubicin were co-formulated into DSPC/SM/DSPE-PEG2000 (90:5:5 mol %) liposomes according to the procedure outlined in Example 5 except liposomes were extruded through an 80 nm and a 100 nm pore size filter ten times. As well, the samples were buffer exchanged into SHE buffer prior to loading of daunorubicin by fixed volume dialysis rather than tangential flow dialysis. As detailed in Example 26, H460 tumor bearing female SCID/rag2 mice (4 mice per group) were administered 15 mg/kg carboplatin and 2.25 mg/kg daunorubicin for liposome formulated drug and free drug cocktail on days 14, 18 and 22. Liposomal drug was administered at a lipid dose of 375 mg/kg.

Figure 10:
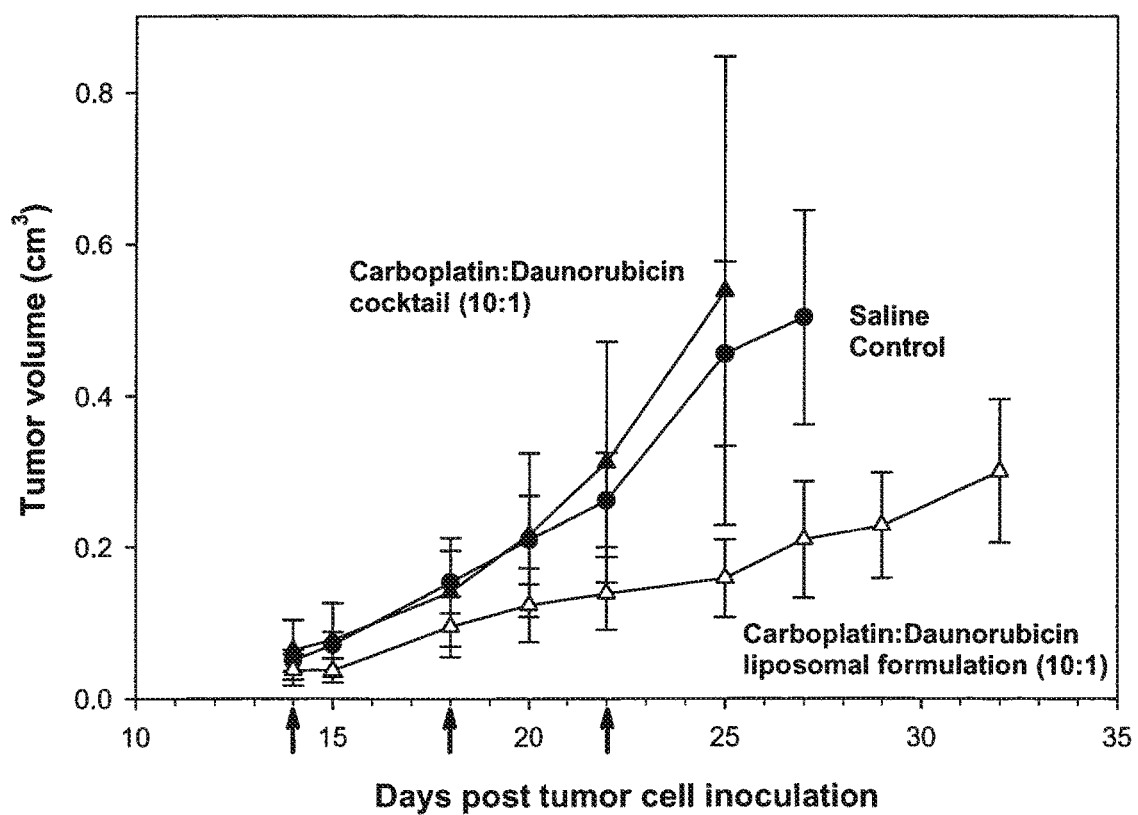
FIG. 10 is a graph comparing the activity of a cocktail of carboplatin and daunorubicin (filled triangles), carboplatin and daunorubicin formulated in a single liposome (open triangles) or saline control (filled circles) given to mice bearing the human H460 non-small cell lung tumor. Carboplatin and daunorubicin were formulated in DSPC/SM/DSPE-PEG2000 (90:5:5 mol %) liposomes at a 10:1 mole ratio. The arrows along the x-axis indicate the dosing schedule.

Results presented in FIG. 10 (points represent mean tumor size+/−SEM determined on the specified day) show that liposomal carboplatin and daunorubicin encapsulated at a 10:1 non-antagonistic mole ratio in sphingomyelin-containing liposomes exhibit substantially increased efficacy in relation to controls consisting of free drug and saline Example 7

Synergism of Cisplatin and Daunorubicin

Figure 11B:
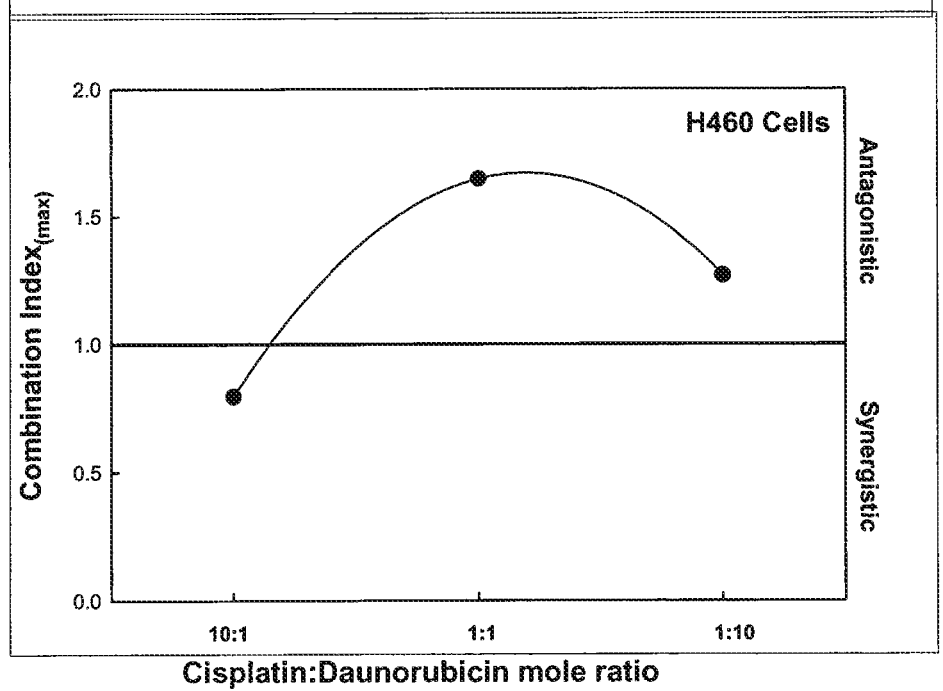
FIG. 11B is a graph of the CI maximum as a function of the cisplatin:daunorubicin at 10:1, 1:1 and 1:10 mole ratios against H460 cells.

Cisplatin/daunorubicin combinations were tested for additive, synergistic or antagonistic effects using the methods described above. The results are summarized in FIG. 11. As shown in FIG. 11A, synergy was observed at a cisplatin/daunorubicin mole ratio of 10:1 over the entire $f_a$ range while the 1:1 mole ratios displayed antagonism over the complete $f_a$ range. FIG. 11B, a plot of CI maximum (CI max) vs. cisplatin-to-daunorubicin ratio, further illustrates the dependence of the combination ratio of two agents on the combination index. These results show that at a 10:1 mole ratio, the CI max value is synergistic while at 1:1 and 1:10 mole ratios the CI max value is antagonistic.

Example 8

Maintaining Synergism of Cisplatin and Daunorubicin In Vivo

Cisplatin and daunorubicin were co-loaded into DMPC/Chol (55:45 mol %) liposomes at a 10:1 mole ratio identified in Example 7 as being non-antagonistic.

Cisplatin was passively entrapped in liposomes by first solubilizing the drug (at 40 mg/mL) in a solution consisting of 150 mM $CuCl_2$, 20 mM histidine (pH 7.4, pH adjusted with triethanolamine) plus 4% (v/v) DMSO and heating the resulting solution to 80° C. to enhance the solubility of cisplatin. The cisplatin solution was then added at 80° C. to a lipid film composed of DMPC and cholesterol with trace levels of $^{14}$C-CHE. The hydrated lipid films were extruded at 80° C. through two 100 nm filters and the liposomes cooled to room temperature. Upon cooling, the samples were centrifuged in a bench top centrifuge at 2000×g for 5 minutes to pellet any unencapsulated cisplatin, and the supernatant collected. Removal of excess metal ions was carried out by passage through a Sephadex G-50 gel filtration column and collection of the liposome fraction.

The cisplatin-loaded liposomes were further loaded with daunorubicin (labeled with trace levels of $^3$H-daunorubicin) at a 10:1 cisplatin/daunorubicin mole ratio by incubation of the liposomes with the drug at 60° C. for 15 minutes. In order to determine the extent of drug loading, cisplatin levels were measured by atomic absorption spectrometry and $^3$H-daunorubicin and lipid levels were measured by liquid scintillation counting.

In order to determine whether coordinated release was achieved by this formulation, the loaded liposomes were injected into the tail vein of male SCID/rag2 mice at 5.0 mg/kg cisplatin and 1.0 mg/kg daunorubicin per mouse. At the indicated time points (3 mice per time point), blood was collected by cardiac puncture and placed into EDTA coated microtainers. The samples were centrifuged and plasma was carefully transferred to another tube. Liposomal lipid and daunorubicin levels in the plasma were both determined by liquid scintillation counting and cisplatin levels were measured by atomic absorption spectrometry.

Figure 12:
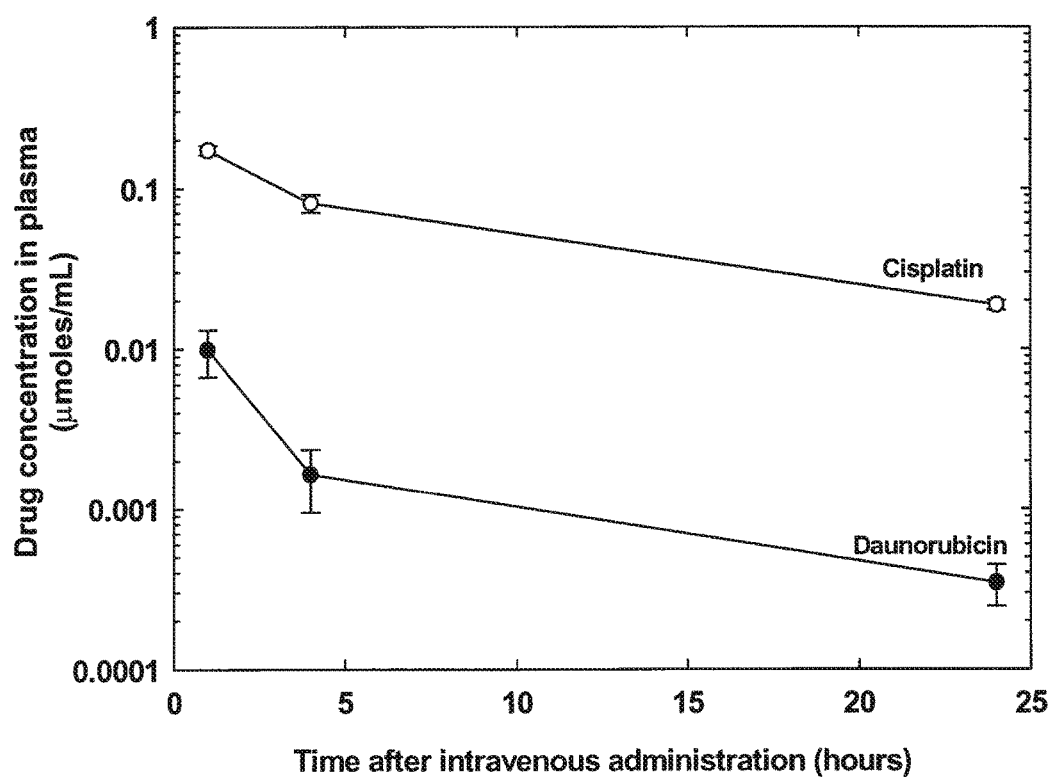
FIG. 12 is a graph of cisplatin (open circles) and daunorubicin (closed circles) concentrations in plasma (μmoles/mL) as a function of time after intravenous administration when the drugs are formulated at a non-antagonistic mole ratio (10:1) in a single liposome (DMPC/Chol, 55:45 mol %).

Results depicted in FIG. 12 (points represent mean drug concentration in plasma +/−SD determined at the specified time) indicate that coordinated release of daunorubicin and cisplatin was achieved as the concentrations in the plasma (μmoles/mL) were maintained at a mole ratio of 10:1 at the time points measured.

Although liposomes may be co-loaded with cisplatin and daunorubicin by the method described above, other techniques may be employed to load the drugs into a single liposome. An alternative method employs the use of a pH gradient to load daunorubicin after passively entrapping cisplatin along with citrate, pH 4.0, and imposing a pH gradient across the membrane by buffer exchange. This technique may be carried out as follows:

Lipid films consisting of DSPC/Chol (55:45 mol %) are prepared as described above along with trace amounts of $^3$H-CHE. A cisplatin solution is prepared by dissolving cisplatin powder into 150 mM NaCl and 150 mM citrate (pH 4). To maximize the solubility of cisplatin in the buffer, the solution is heated to 65° C. and added to the lipid films. The resulting MLVs are extruded at 65° C. through two 100 nm pore size filters for a total of ten passes. Unencapsulated cisplatin is then removed from the formulation by centrifuging the solution at 2000×g for 10 minutes. The resulting supernatant containing liposomal cisplatin is passed down a Sephadex G-50 column that is pre-equilibrated in 150 mM NaCl and 20 mM HEPES (pH 7.4) to remove any residual unentrapped cisplatin and to establish a pH gradient across the bilayer.

Daunorubicin is subsequently loaded into the liposomes by first incubating the liposomes at 60° C. for 5 minutes to achieve thermal equilibration and then adding daunorubicin to the lipid formulation at a 0.1:1 drug/lipid mole ratio while vortexing. To determine the extent of drug loading at various times, the concentration of daunorubicin is determined by solubilizing the liposomes with OGP and measuring the absorbance of daunorubicin at 480 nm. The cisplatin concentration of the formulation is measured using atomic absorption spectrometry. Lipid concentrations are measured by liquid scintillation counting.

An alternative means of coordinating the release kinetics of two drugs can be achieved by formulating each drug in separate carriers. This was demonstrated by formulating cisplatin in DMPC/cholesterol liposomes and daunorubicin in DSPC/DSPE-PEG2000 liposomes and administering them intravenously to mice at a 10:1 mole ratio.

Liposomal cisplatin was prepared by first dissolving cisplatin (8.5 mg/mL) in 150 mM NaCl at 80° C. The solution was next added to a DMPC/cholesterol (55:45 mol %) lipid film containing trace amounts of $^3$H-CHE and allowed to hydrate. The resulting MLVs were extruded at 80° C. through two 100 nm pore size filters and the liposomes were subsequently exchanged into 20 mM HEPES, 150 mM NaCl (pH 7.4) (HBS) by tangential flow dialysis to remove excess metal ions. The liposomes were centrifuged to pellet any unencapsulated cisplatin after extrusion. The cisplatin concentration was determined by atomic absorption spectrometry and lipid levels were determined by liquid scintillation counting.

Liposomal daunorubicin was prepared by hydration of a lipid film composed of DSPC/ DSPE-PEG2000 (95:5 mol %) and trace amounts of $^{14}$C-CHE with a solution of 300 mM CuSO$_4$. The resulting MLVs were extruded by ten passes through two stacked 100 nm pore size filters at 70° C. After extrusion, the liposomes were exchanged into HBS (pH 7.4) by tangential flow dialysis. Loading of daunorubicin (with trace levels of $^3$H-daunorubicin) was initiated by the addition of daunorubicin to a final drug/lipid weight ratio of 0.1 and holding the solution at 60° C. for 10 minutes. The extent of drug loading was measured by liquid scintillation counting to measure $^3$H-daunorubicin and $^{14}$C-CHE levels.

Male SCID/rag 2 mice were injected intravenously with liposomal cisplatin at a drug dose of 2 mg/kg and liposomal daunorubicin at a drug dose of 0.375 mg/kg. At the indicated time points (3 mice per time point), blood was collected by cardiac puncture and placed into EDTA coated microtainers. The samples were centrifuged and plasma was carefully transferred to another tube. Plasma cisplatin levels were determined by atomic absorption spectrometry and daunorubicin levels were determined by scintillation counting.

Figure 13:
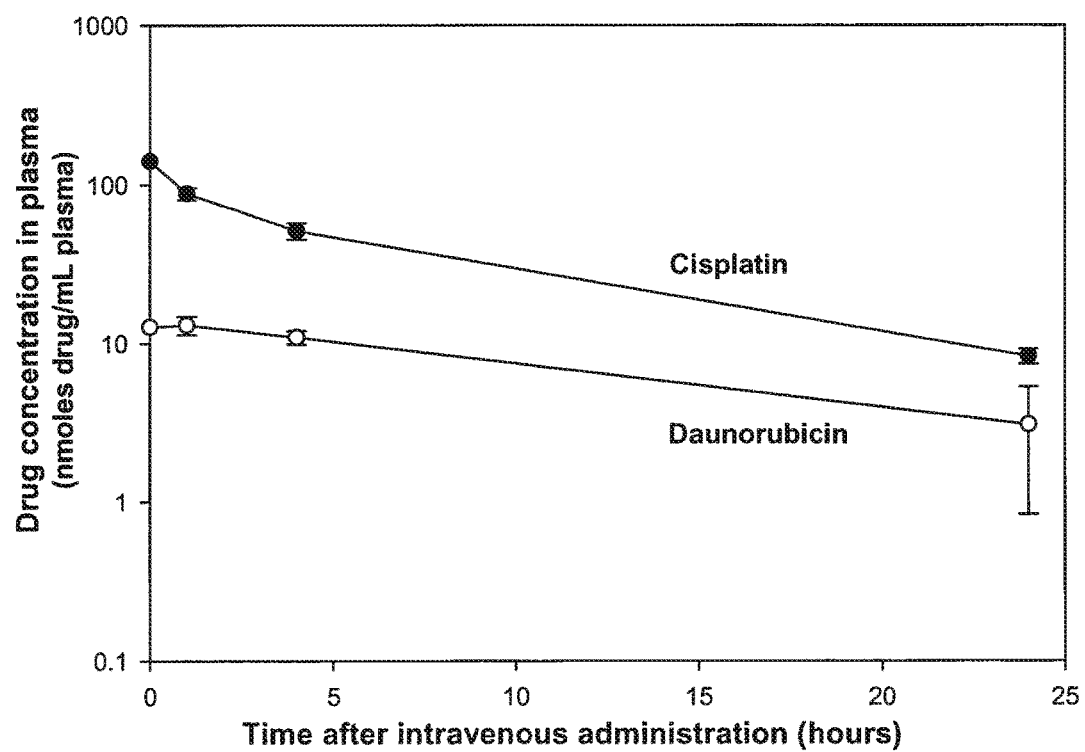
FIG. 13 is a graph of cisplatin (closed circles) and daunorubicin (open circles) concentrations in the plasma (μmoles/mL) as a function of time after intravenous administration when the drugs are formulated at a non-antagonistic mole ratio (10:1) in two separate liposomes (DMPC/Chol, 55:45 mol % for cisplatin and DSPC/DSPE-PEG2000, 95:5 mol % for daunorubicin).

Results shown in FIG. 13 (points represent mean drug concentrations determined in plasma+/−SD at the specified time points) reveal that cisplatin and daunorubicin formulated in separate liposomes were maintained at a 10:1 mole ratio at various time points after intravenous administration.

Example 9

Efficacy of Liposomal Cisplatin and Daunorubicin

The efficacy of cisplatin and daunorubicin formulated in separate liposomes was determined in SCID/rag2 mice (H460 xenograft model) as detailed in Example 26. H460 tumor bearing mice (4 mice per group) were treated with saline or with cisplatin/daunorubicin at a 10:1 mole ratio that was identified in vitro in Example 7 as being non-antagonistic. Cisplatin and daunorubicin were formulated in DMPC/Chol (55:45 mol %) and DSPC/DSPE-PEG2000 (95:5 mol %) liposomes respectively as set forth in Example 8, except DMPC/Chol liposomes were dialyzed against HBS after extrusion. Animals treated with the drug combination received the agents as either a cocktail of the free agents (cocktail; 10:1, mole ratio) or by co-administration of liposomal daunorubicin and liposomal cisplatin (liposome formulation; 10:1 mole ratio) on days 14, 17 and 21. For both the free and formulated treatments, the doses were 2.0 mg/kg of cisplatin and 0.375 mg/kg of daunorubicin. Lipid doses were 400 mg/kg for liposomal cisplatin and 3.75 mg/kg for liposomal daunorubicin.

Figure 14:
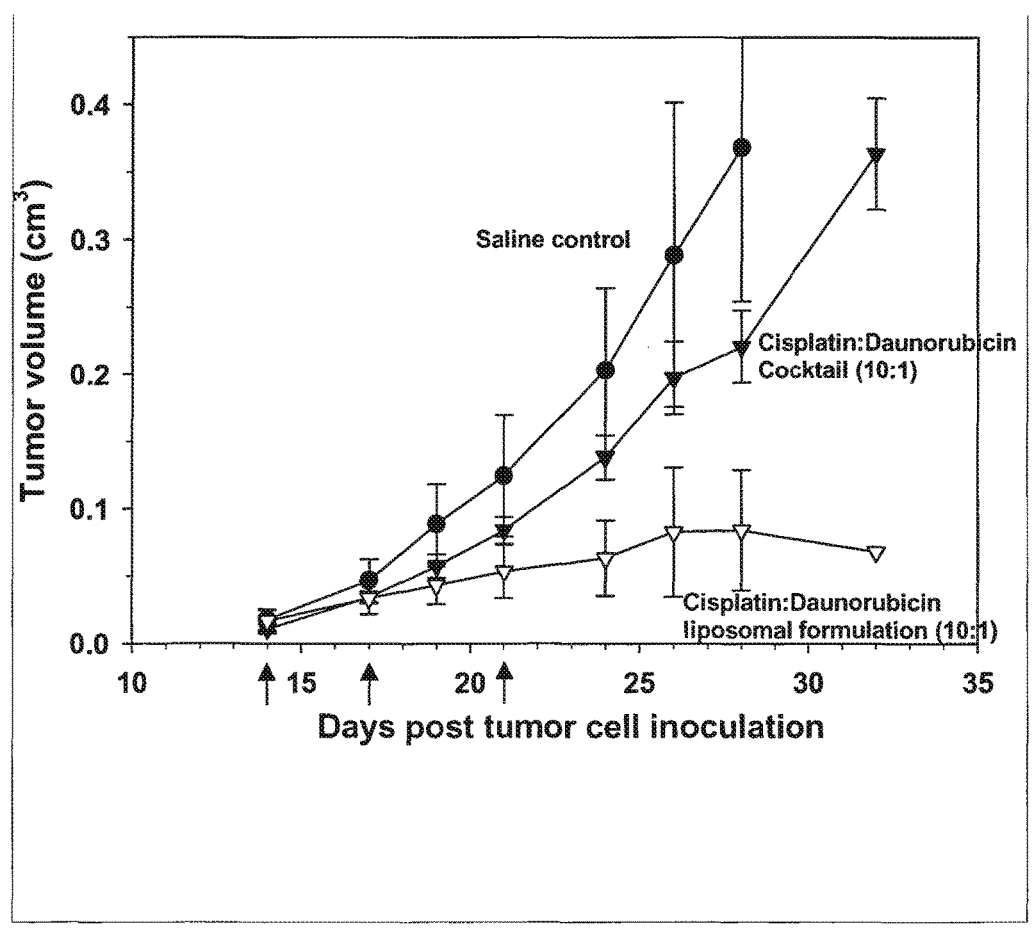
FIG. 14 is a graph comparing the activity of a cocktail of cisplatin and daunorubicin (filled inverted triangles), cisplatin and daunorubicin formulated in separate liposomes (open inverted triangles) or saline control (filled circles) given to mice bearing the human H460 non-small cell lung tumor. Cisplatin was formulated in DMPC/Chol (55:45 mol %) liposomes and daunorubicin was formulated in DSPC/DSPE-PEG2000 (95:5 mol %) liposomes and administered at a non-antagonistic mole ratio (10:1). Arrows indicate the days on which the doses were administered.

FIG. 14 shows the results, where each data point represents mean tumor size+/−SEM determined on the specified day. The saline control (solid circles) did not inhibit tumor growth; similarly, the free cocktail (solid inverted triangles) showed only a slight effect on tumor growth. In comparison, the liposomal formulation (open triangles) inhibited tumor growth over a period of at least 32 days.

Example 10

Effect of Liposomal Administration of a Drug Combination at an Antagonistic Mole Ratio Cisplatin and daunorubicin were co-loaded into DMPC/Chol (55:45 mol %) liposomes at a 1:1 mole ratio that was determined in Example 7 to be antagonistic. Cisplatin was passively entrapped and daunorubicin actively entrapped to achieve a cisplatin/daunorubicin mole ratio of 1:1. The procedure outlined in Example 8 was employed to load the drugs into a single liposome.

Figure 15:
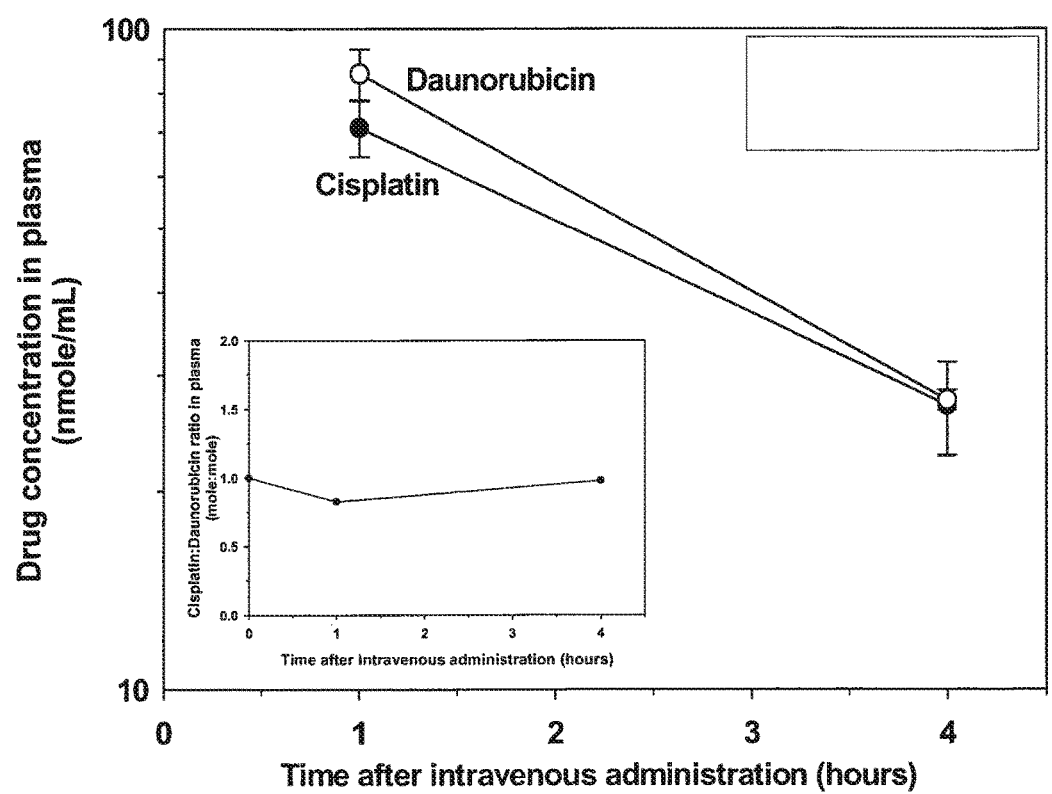
FIG. 15 is a graph showing concentrations of cisplatin (closed circles) and daunorubicin (open circles) remaining in the plasma (nmoles/mL) at various times after intravenous administration when the drugs were formulated in a single liposome (DMPC/Chol, 55:45 mol %) at an antagonistic 1:1 mole ratio. The inset shows the cisplatin:daunorubicin mole ratio at various time points after administration.

In order to determine whether coordinated release was achieved by formulation in DMPC/Chol liposomes, the loaded liposomes were injected into the tail vein of Balb/c mice at 2 mg/kg cisplatin and 3.75 mg/kg daunorubicin. At the indicated time points (3 mice per time point), blood was collected by cardiac puncture and placed into EDTA coated microtainers. The samples were centrifuged and plasma was carefully transferred to another tube. Lipid and daunorubicin plasma levels were both determined by liquid scintillation counting and cisplatin levels were measured by atomic absorption spectrometry. Results summarized in FIG. 15 (data points represent mean drug concentrations determined in plasma+/−SD at the specified time points) show that daunorubicin and cisplatin were eliminated from the plasma at the same rate, thus the concentrations in the plasma (nmoles/mL) were maintained at a mole ratio of 1:1 (see insert to FIG. 15).

Efficacy studies were carried out as described in Example 26, where H460 tumor bearing female SCID/rag2 mice were dosed at 2.5 mg/kg cisplatin, 4.7 mg/kg daunorubicin in either cocktail or liposomal formulation and 52.83 mg/kg lipid on days 11, 15 and 19.

Figure 16:
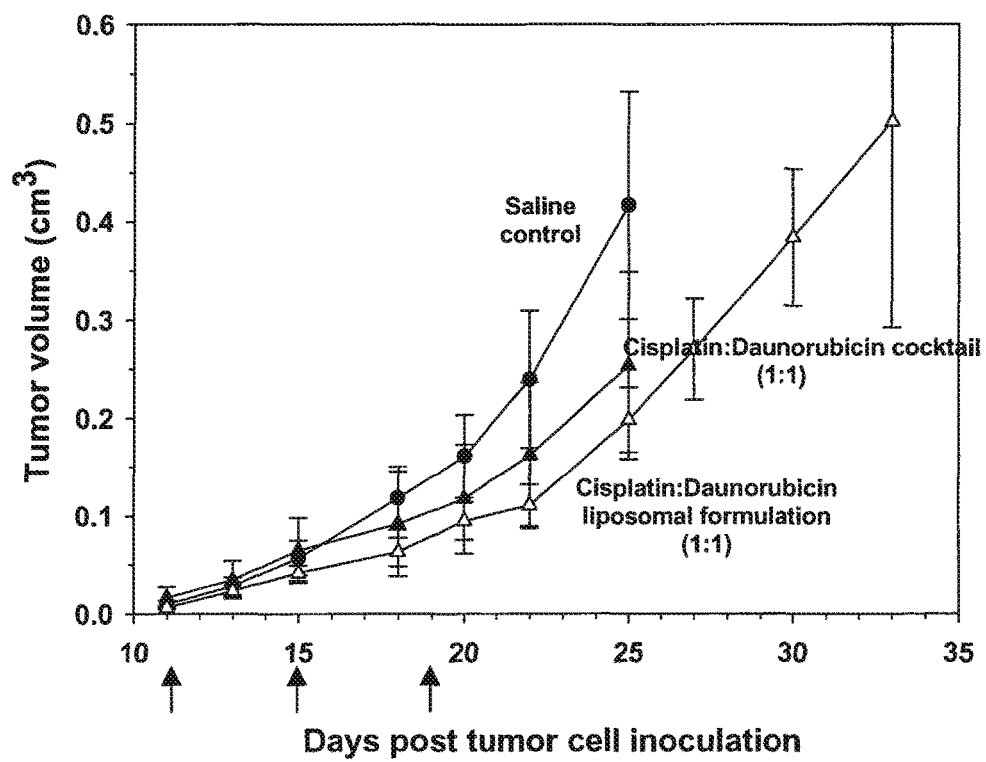
FIG. 16 is a graph comparing the activity of a cocktail of cisplatin and daunorubicin (filled triangles), cisplatin and daunorubicin formulated in a single liposome (open triangles) or saline control (filled circles) given to mice bearing the human H460 non-small cell lung tumor. The drugs were formulated in DMPC/Chol (55:45 mol %) liposomes at an antagonistic mole ratio (1:1). Arrows indicate the days on which the doses were administered.

Efficacy results in FIG. 16 (data points represent mean tumor size+/−SEM determined on the specified day) show that treatment with daunorubicin and cisplatin at an antagonistic ratio is ineffective at reducing tumor growth when compared to results at a non-antagonistic ratio (10:1 mole ratio) of the agents where tumor growth was substantially inhibited (see FIG. 14). These results thus highlight the importance of selecting drug combinations at ratios that exhibit non-antagonistic effects over a range of concentrations in vitro. It should be noted that the drug doses used in FIG. 16 (2.5 mg/kg cisplatin and 4.7 mg/kg daunorubicin) are actually higher than those used in FIG. 14 (2 mg/kg cisplatin, 0.375 mg/kg daunorubicin).

Example 11

Synergism of Cisplatin and Topotecan

Figure 17A:
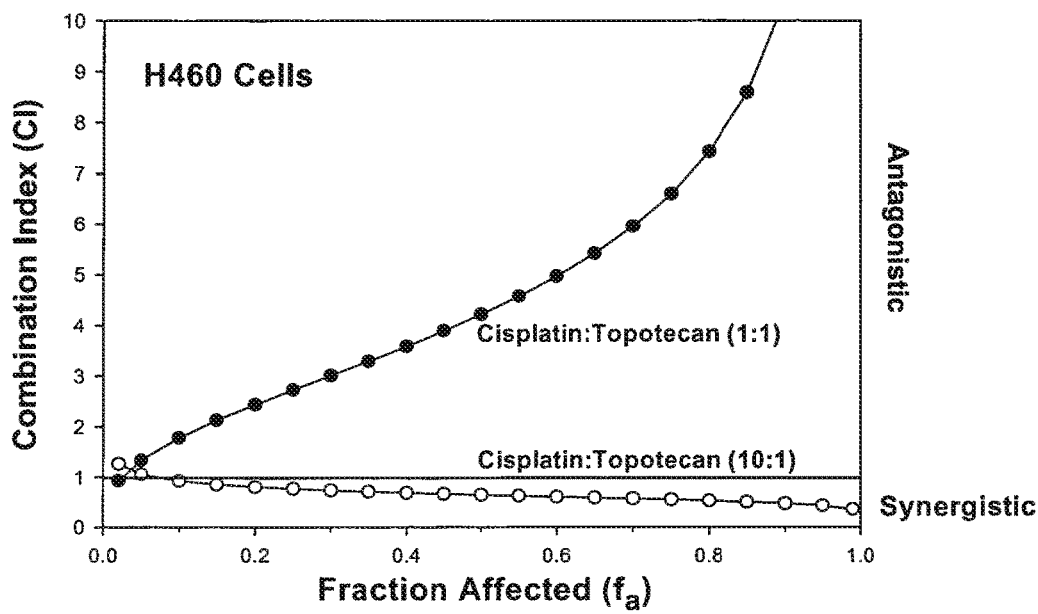
FIG. 17A is a graph of the CI for cisplatin:topotecan at mole ratios of 1:1 (filled circles) and 10:1 (open circles) as a function of the fraction of H460 cells affected ($f_a$).

The procedure set forth above (see Example 1) for determining synergistic, additive or antagonistic effects was repeated using cisplatin/topotecan, both at a 10:1 mole ratio and at a 1:1 mole ratio. As shown in FIG. 17A, cisplatin/topotecan at a 10:1 mole ratio has a non-antagonistic interaction over a wide range of doses that affect 5% to 99% of cells ($f_a$=0.05 to $f_a$=0.99). In contrast, cisplatin/topotecan at a 1:1 mole ratio was strongly antagonistic over the same $f_a$ range (FIG. 17A).

Figure 17B:
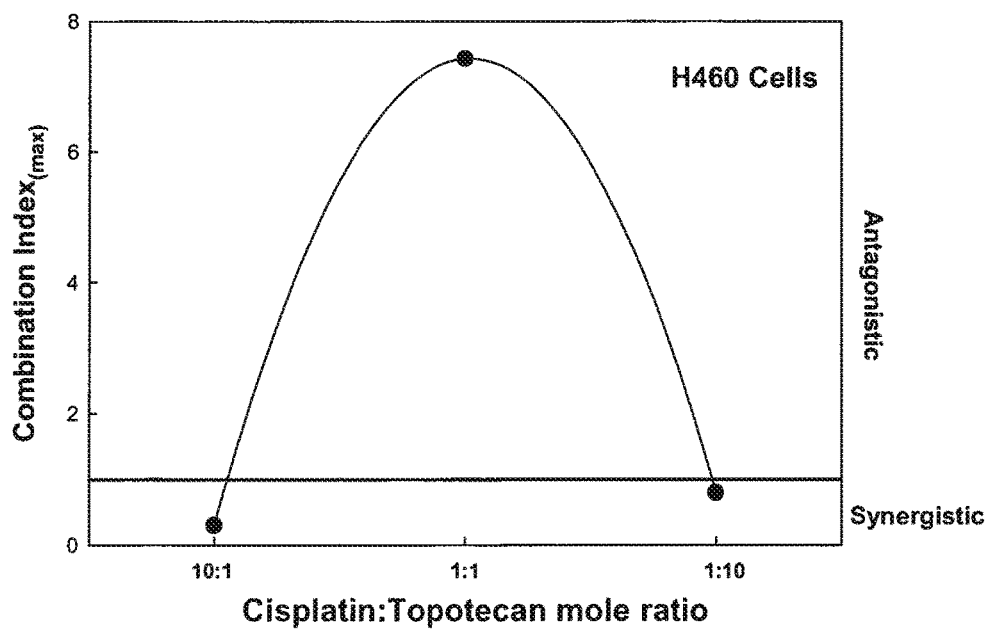
FIG. 17B is a graph of the CI maximum as a function of the cisplatin:topotecan mole ratio against H460 cells.

This effect of concentration was also evidenced by calculating a CI maximum for various mole ratios of cisplatin/topotecan. As shown in FIG. 17B, an antagonist effect appears maximized at a 1:1 mole ratio and non-antagonistic effects are apparent when either drug is in excess.

Example 12

Maintaining Synergism of Cisplatin and Topotecan In Vivo

Cisplatin and topotecan were formulated into DMPC/Chol and DSPC/Chol liposomes, respectively, and injected intravenously into mice at a 10:1 mole ratio identified in Example 11 to be synergistic.

Liposomal cisplatin was prepared by hydration of a lipid film consisting of DMPC and cholesterol (55:45 mol %) with a solution consisting of 150 mM NaCl and 8.5 mg/mL of cisplatin. The resulting MLVs were extruded at 80° C. by ten passes through two stacked 100 nm pore size filters. After extrusion, the sample was cooled and precipitated cisplatin was removed by centrifugation. The remaining soluble cisplatin that was not encapsulated in the liposomes was removed by dialysis against HBS. After the removal of non-encapsulated cisplatin, the concentration of the drug was measured by atomic absorption spectrometry.

Liposomal topotecan was prepared by hydration of a lipid film composed of DSPC and cholesterol (55:45 mol %) with a solution of 300 mM $MnSO_4$. The resulting MLVs were extruded at 65° C. by ten passes through two stacked 100 nm filters. After extrusion, the liposomes were exchanged into SHE buffer (300 mM sucrose, 20 mM HEPES and 30 mM EDTA, pH 7.4) by gel filtration chromatography. Loading of topotecan was initiated by the addition of 1 μg of A23187/μmol lipid (A23187 is a cationic ionophore that mediates the exchange of a divalent metal ion for two protons across a bilayer) and topotecan to a final topotecan/lipid ratio of 0.08 (w/w), then holding the solution at 65° C. for 15 minutes. The extent of topotecan loading was measured by absorbance at 380 nm after separation of encapsulated and non-encapsulated drug using gel filtration chromatography and solubilization in Triton X-100.

The preparations were injected intravenously via the tail vein into SCID/rag2 female mice. Doses of the liposomal formulations were 5 mg/kg of cisplatin and 0.758 mg/kg of topotecan. At the indicated time points (3 mice per time point), blood was collected by cardiac puncture and placed into EDTA coated microtainers. The samples were centrifuged and plasma was carefully transferred to another tube. Liquid scintillation counting was used to quantitate radio-labeled lipid. Cisplatin was measured using atomic absorption spectrometry while topotecan was measured by fluorescence spectroscopy (excitation at 380 nm and emission at 518 nm) after disruption of the liposomes with excess detergent.

Figure 18:
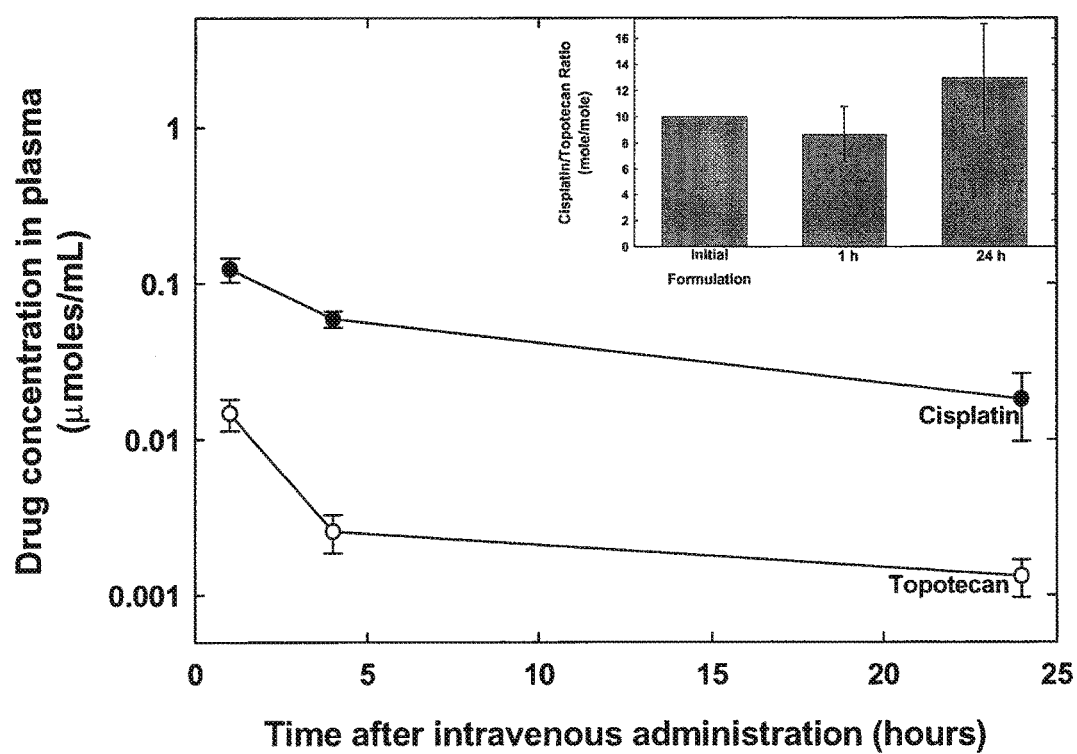
FIG. 18 is a graph showing concentrations of cisplatin (closed circles) and topotecan (open circles) remaining in the plasma (µmoles/mL) at various times after intravenous administration when the drugs are formulated in separate liposomes (DMPC/Chol, 55:45 mol % for cisplatin and DSPC/Chol, 55:45 mol % for topotecan). The inset shows the cisplatin to topotecan mole ratio at various time points after administration.

FIG. 18 (data points represent mean drug concentrations determined in plasma +/−SD at the specified time points) shows that plasma levels of cisplatin and topotecan were maintained at a 10:1 mole ratio as plasma levels of cisplatin were roughly ten times that of topotecan at various time points after intravenous administration when they were delivered in the above-described liposomes. These results demonstrate that the drug retention and liposome elimination characteristics of two encapsulated agents in two different liposomes can be coordinated such that coordinated drug elimination rates are realized. The inset of FIG. 18 shows that the plasma cisplatin-to-topotecan mole ratios (+/−SD) present in the plasma after intravenous administration vary little over time.

Cisplatin and topotecan can also be formulated in a single liposome in order to ensure non-antagonistic ratios are maintained in vivo. This may be carried out by passive entrapment of cisplatin followed by ionophore-mediated loading of topotecan. A cisplatin solution is first prepared by dissolving cisplatin powder into a solution of 150 mM $MnCl_2$. To maximize the solubility of cisplatin in the $MnCl_2$ solution, the solution is heated to 65° C. A lipid film composed of DSPC/Chol (55:45 mol %) along with trace amounts of $^3$H-CHE is hydrated with the cisplatin/$MnCl_2$ solution. The resulting MLVs are extruded at 65° C. through two 100 nm filters for a total of ten passes. Insoluble cisplatin is then removed from the formulation by cooling the formulation to room temperature and centrifuging the solution at 2000×g. The resulting supernatant containing liposomal and soluble but unencapsulated cisplatin is dialyzed against SHE buffer, 300 mM sucrose, 20 mM HEPES, and 30 mM EDTA (pH 7.4) overnight at room temperature.

Topotecan is subsequently loaded into the liposomes using an ionophore-mediated proton gradient. Drug uptake is performed at a 0.08:1 drug to lipid weight ratio (w/w). The divalent cation ionophore A23187 (1 μg ionophore/μmol lipid) is added to the liposomes, and then the mixture is incubated at 60° C. for 15 minutes to facilitate A23187 incorporation into the bilayer. Subsequently, topotecan is added, and the mixture is incubated at 60° C. for 60 minutes to facilitate drug uptake. Unencapsulated topotecan and A23187 are removed from the preparation by dialyzing the sample against 300 mM sucrose. The extent of topotecan loading is quantified by measuring absorbance at 380 nm. Cisplatin levels are measured by atomic absorption spectrometry and lipid levels by liquid scintillation counting.

Example 13

Efficacy of Liposomal Cisplatin and Topotecan

The efficacy of cisplatin and topotecan loaded into separate liposomes was investigated by formulating the two drugs in separate liposomes and administering the formulation at a 10:1 mole ratio identified in Example 11 as being non-antagonistic. Liposomal cisplatin was passively entrapped in DMPC/Chol (55:45 mol %) liposomes as described in the procedures of Example 12. Topotecan was formulated in DSPC/Chol (55:45 mol %) as in Example 12 as well, except loading of topotecan was to a final topotecan/lipid weight ratio of 0.1 (w/w). Following loading, the external buffer was exchanged into HBS.

Efficacy studies were conducted as detailed in Example 26, where H460 tumor bearing female SCID/rag2 mice (4 mice per group) were treated intravenously (on days 13, 17, 21) with saline (control), free cocktail or a liposomal mixture of cisplatin/topotecan at a 10:1 mole ratio identified as non-antagonistic in Example 11. For both the free and liposome-formulated treatments, the doses were 1.6 mg/kg of cisplatin and 0.25 mg/kg of topotecan. Lipid doses were 250 mg/kg arising from the cisplatin formulation plus 2.5 mg/kg from the topotecan formulations.

Figure 19:
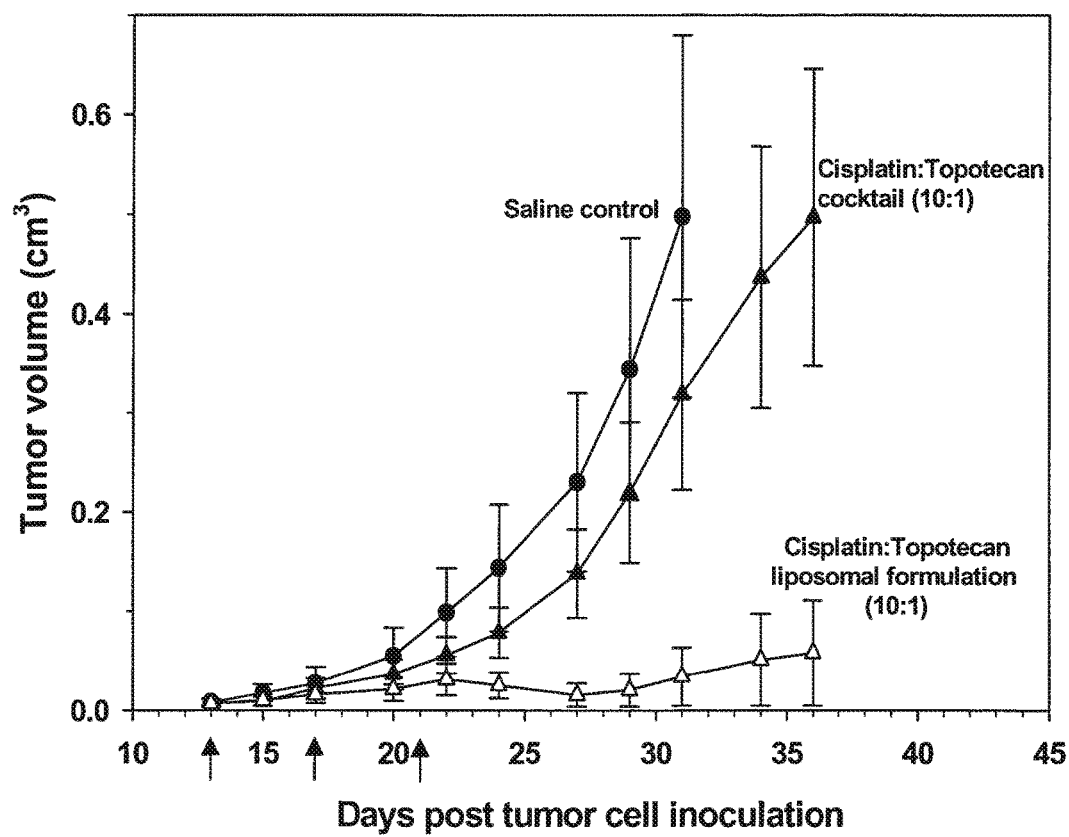
FIG. 19 is a graph comparing the activity of a cocktail of cisplatin and topotecan (filled triangles), cisplatin and topotecan formulated in separate liposomes (open triangles) or saline control (filled circles) given to mice bearing the human H460 non-small cell lung tumor. Cisplatin was formulated in DMPC/Chol (55:45 mol %) liposomes and topotecan was formulated in DSPC/Chol (55:45 mol %) liposomes and were administered at a non-antagonistic mole ratio (10:1). Arrows indicate the days on which the doses were administered.

FIG. 19 shows the results (data points represent mean tumor size+/−SEM determined on the specified day). The saline control (solid circles) and the cocktail of cisplatin/topotecan 10:1 (solid triangles) did not effectively arrest tumor volume. However, the liposomal preparation of cisplatin/topotecan 10:1 (open triangles) prevented the increase in tumor volume for a period of at least 35 days.

Example 14

Synergism of Cisplatin and Irinotecan

Figure 20A:
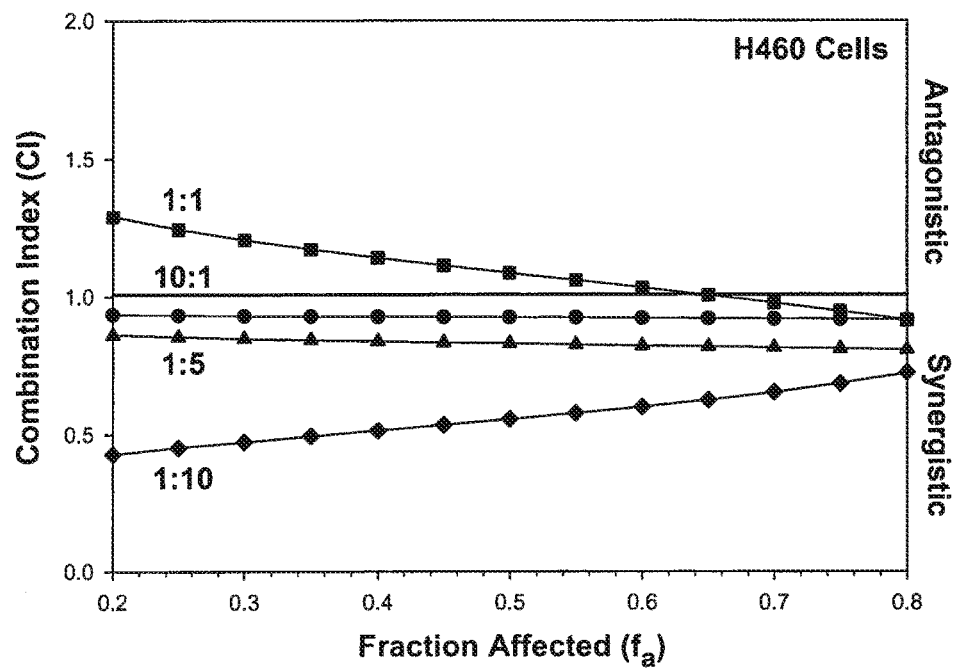
FIG. 20A is a graph of the CI for cisplatin:irinotecan at mole ratios of 1:1 (squares), 10:1 (circles), 1:5 (triangles) and 1:10 (diamonds) as a function of the fraction of H460 cells affected ($f_a$).
Figure 20B:
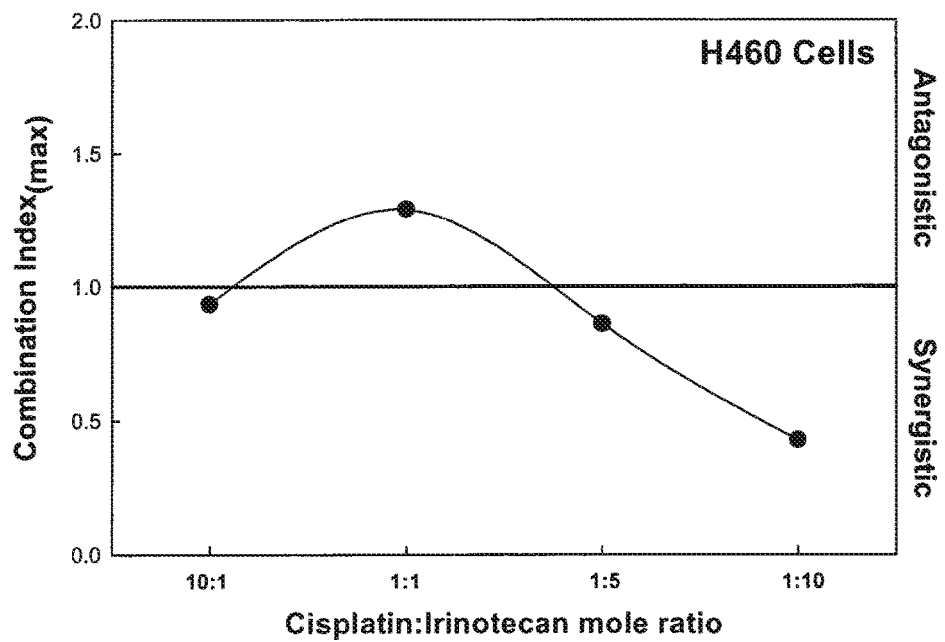
FIG. 20B is a graph of the CI maximum as a function of the cisplatin:irinotecan mole ratio against H460 cells.

Combinations of cisplatin and irinotecan at mole ratios of 1:1, 10:1, 1:5 and 1:10 were tested for synergy, additivity or antagonism according to the methods described above (see Example 1). Results summarized in FIG. 20A show that mole ratios of 10:1, 1:5 and 1:10 were non-antagonistic over the complete range of $f_a$ values whereas a 1:1 ratio was antagonistic over a substantial range of $f_a$ values. FIG. 20B further illustrates the dependency of the ratio on the nature of the combination effect as summarized by plotting the combination index maximum against the cisplatin to irinotecan mole ratio.

Example 15

Maintaining Synergism of Cisplatin and Irinotecan In Vivo

Cisplatin and irinotecan were co-loaded into DSPC/DSPG (80:20 mol %) liposomes, which were prepared as described in Example 5 except that lipid films were rehydrated in 225 mM copper (75 mM $CuCl_2$, 150 mM $CuSO_4$, triethanolamine (TEA), pH 6.8) containing 6.0 mg/mL of cisplatin. The liposomal cisplatin concentration after extrusion and removal of unencapsulated drug was 0.025 mole cisplatin/mole lipid. The resulting liposomes were dialyzed against SHE, pH 6.8 overnight. Irinotecan was then added to the preparation and the liposomes were incubated at 45° C. for 1.5 hours. The liposomes loaded 60% of the added irinotecan as determined by HPLC. The liposomes were then buffer exchanged into 0.9% saline by tangential flow. After tangential flow, the liposomes retained approximately 80% of the original cisplatin and irinotecan. Analysis of cisplatin and irinotecan, as determined by atomic absorption spectrometry and HPLC analysis, respectively, indicated that the final preparation had a cisplatin-to-irinotecan mole ratio of 1:3. SCID/rag2 mice were intravenously administered 2 mg/kg cisplatin and 38.6 mg/kg irinotecan. At the indicated time points (3 mice per time point), blood was collected by cardiac puncture and placed into EDTA coated microtainers. The samples were centrifuged and plasma was carefully transferred to another tube. Plasma irinotecan and cisplatin levels were determined by HPLC and atomic absorption spectrometry, respectively.

Figure 21:
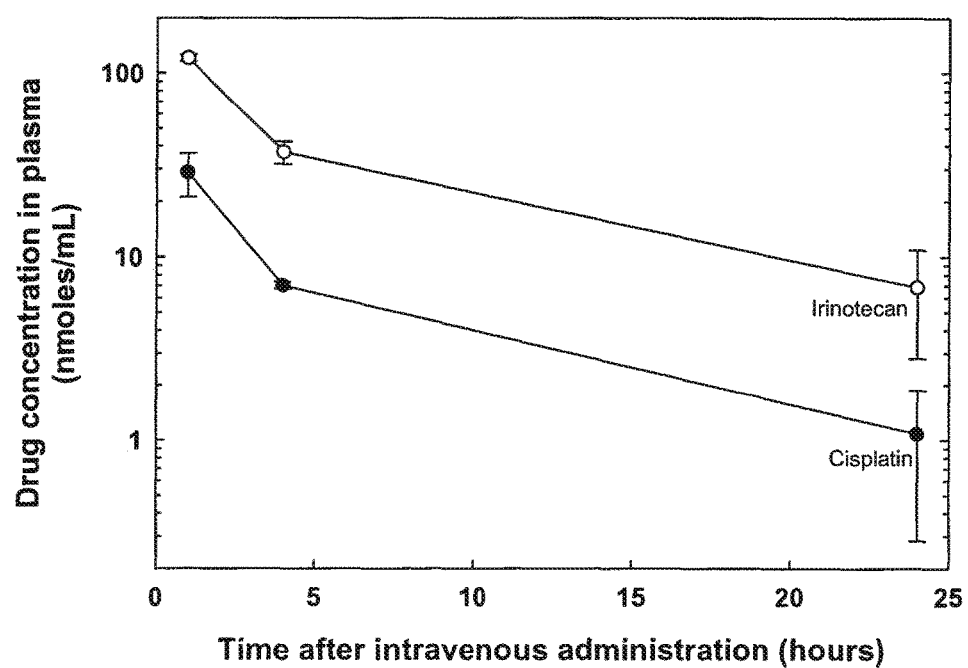
FIG. 21 is a graph showing the concentrations of cisplatin (filled circles) and irinotecan (open circles) remaining in the plasma (nmoles/mL) at various time points after intravenous administration when the drugs were co-loaded into a single liposome (DSPC/DSPG, 80:20 mol %).

Results in FIG. 21 (data points represent mean drug concentrations determined in plasma+/−SD at the specified time points) show that following intravenous injection of formulations containing cisplatin and irinotecan, co-loaded into DSPC/DSPG liposomes, the rates of drug elimination were comparable and non-antagonistic mole drug ratios could be maintained over the 24-hour time course after administration.

Coordinated release of liposomal cisplatin and irinotecan in vivo was also achieved by formulating the two drugs in separate delivery vehicles and administering the drugs at a 1:5 mole ratio (cisplatin/irinotecan).

Liposomal cisplatin was prepared according to the passive loading technique described above. Lipid films consisting of DMPC/Chol (55:45 mol %) were hydrated with a solution of 150 mM NaCl containing 8.5 mg/mL cisplatin, then extruded as described above. The liposomes were collected in the supernatant after centrifugation as above then exchanged into HBS by tangential flow dialysis.

Liposomal irinotecan was prepared by hydrating lipid films consisting of DSPC/DSPE-PEG2000 (95:5 mol %) with a solution consisting of 150 mM $CuCl_2$, 20 mM histidine, pH 6.8 (pH adjusted with TEA). The resulting MLVs were extruded at 65° C. through two stacked 100 nm pore size filters and buffer exchanged with HBS by tangential flow. The extruded liposomes were loaded with irinotecan at 60° C. for 1 minute at a 0.1:1 drug to lipid weight ratio. The extent of loading of irinotecan was determined by absorbance at 370 nm after solubilization in Triton X-100; lipid levels were measured by liquid scintillation counting.

Liposomal cisplatin was administered to male SCID/rag2 mice at a drug dose of 2.0 mg/kg and liposomal irinotecan was administered to the mice at 20 mg/kg. At the indicated time points (3 mice per time point), blood was collected by cardiac puncture and placed into EDTA coated microtainers. The samples were centrifuged and plasma was carefully transferred to another tube. Plasma irinotecan levels were measured by HPLC and cisplatin was measured by atomic absorption spectrometry.

Figure 22:
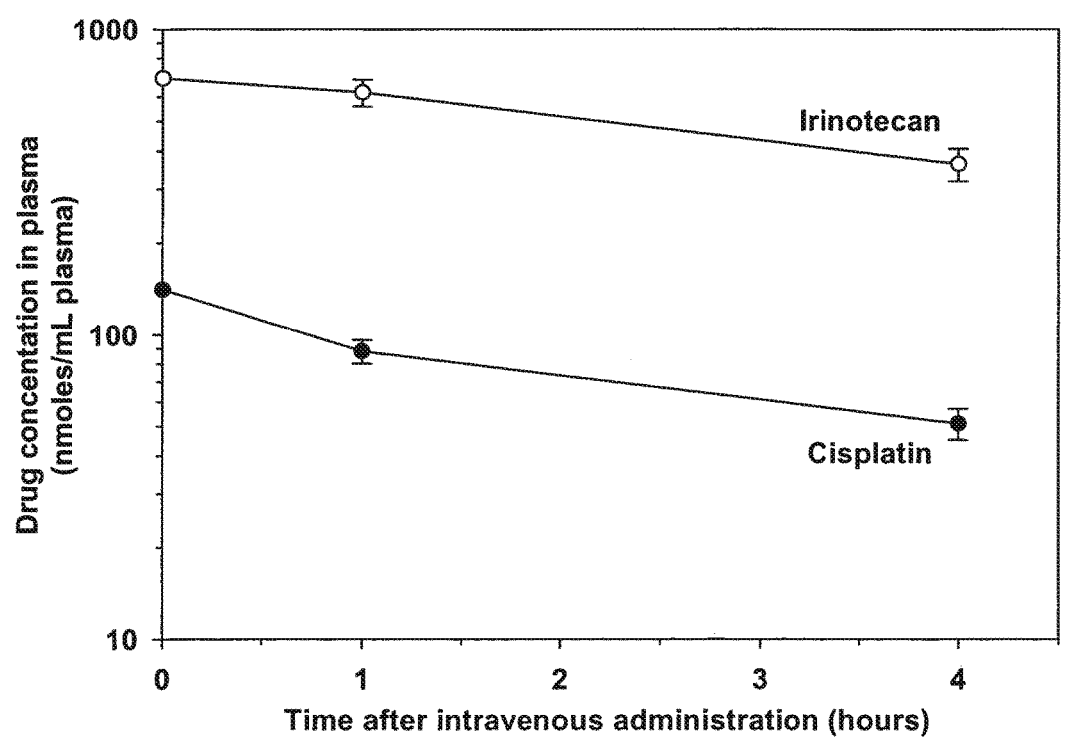
FIG. 22 is a graph showing the concentrations of cisplatin (closed circles) and irinotecan (open circles) remaining in the plasma (nmoles/mL) at various time points after intravenous administration when the drugs are formulated in separate liposomes (DMPC/Chol, 55:45 mol % for cisplatin and DSPC/DSPE-PEG2000, 95:5 mol % for irinotecan).

Cisplatin and irinotecan administered together in these liposomal formulations at this synergistic ratio (1:5 mole ratio) maintain this ratio at 1:5 following intravenous administration as evidenced by the plasma concentrations of irinotecan (nmoles/mL) being roughly five times that of cisplatin (nmoles/mL) at various time points (FIG. 22).

Example 16

Efficacy of Liposomal Cisplatin and Irinotecan

Efficacy studies were carried out on liposomal cisplatin and irinotecan formulated into separate liposomes. Cisplatin was passively entrapped in DMPC/Chol (55:45 mol %) liposomes and irinotecan was loaded into DSPC/DSPE-PEG2000 (95:5 mol %) liposomes as detailed in Example 15. Liposomal cisplatin and irinotecan were co-administered to H460 tumor bearing SCID/rag2 mice according to the methods described in Example 26 at a 1:5 mole ratio determined to be non-antagonistic in Example 14. Liposomal cisplatin and irinotecan were administered (4 mice per group on days 14, 18 and 22) at the non-antagonistic mole ratio of 1:5 with doses of 1 mg/kg cisplatin, 10 mg/kg irinotecan and 130 mg/kg lipid (open squares); 2.5 mg/kg cisplatin, 25 mg/kg irinotecan and 175 mg/kg lipid (open upward triangles); or, 5 mg/kg cisplatin, 50 mg/kg irinotecan and 250 mg/kg lipid (open inverted triangles). Free cisplatin/irinotecan was dosed at 1 mg/kg cisplatin and 10 mg/kg irinotecan which reflects a 1:5 mole ratio (solid squares).

Figure 23:
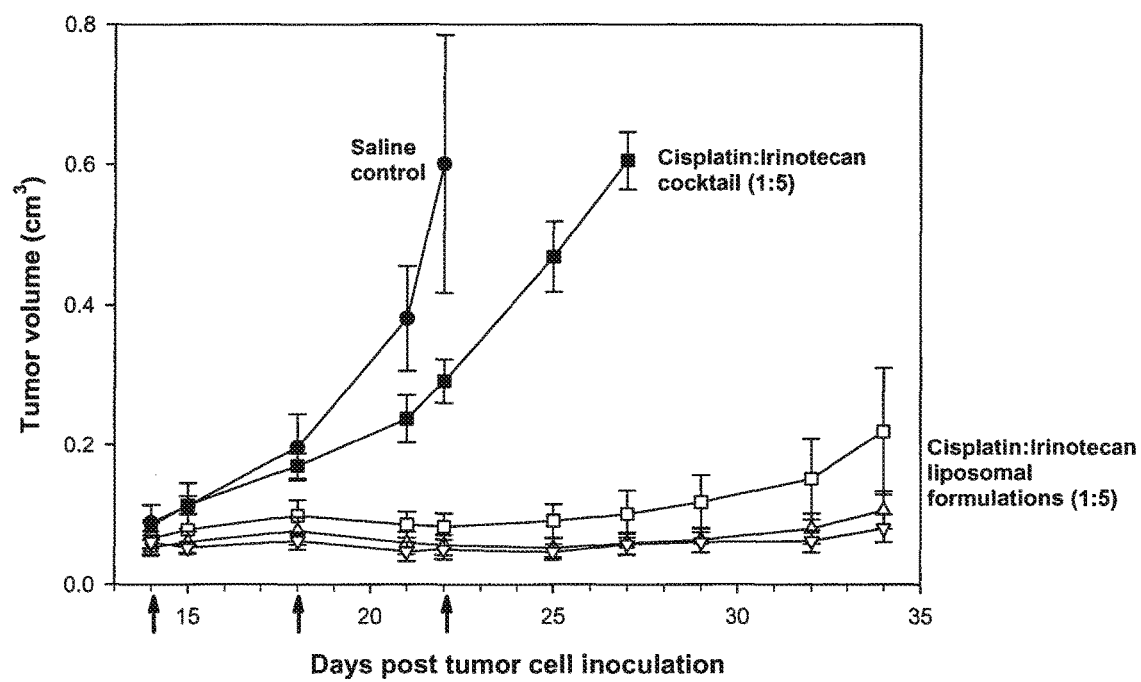
FIG. 23 is a graph comparing the activity of a cocktail of cisplatin and irinotecan (filled squares), cisplatin and irinotecan formulated in separate liposomes and administered at different doses (open symbols) or saline control (filled circles) given to mice bearing the human H460 non-small cell lung tumor. Cisplatin formulated in DMPC/Chol (55:45 mol %) liposomes and irinotecan formulated in DSPC/DSPE-PEG2000 (95:5 mol %) liposomes were administered at a non-antagonistic mole ratio (1:5). Arrows indicate the days on which the doses were administered.

FIG. 23 (data points represent mean tumor size+/−SEM determined on the specified day) illustrates that tumor growth for the liposomal preparations was substantially suppressed in relation to free drug cocktail and saline treated mice.

Example 17

Synergism of Drug and Lipid Combinations

Combinations comprising vinorelbine at a 1:1 mole ratio with various potentially therapeutic lipids incorporated into the lipid bilayer, such as POPS (inverted triangles), DPPS (upward triangles), DLPS (circles), DSPS (diamonds) or DOPS (squares), were tested for additive, synergistic or antagonistic effects using the method described above (see Example 1).

Figure 24:
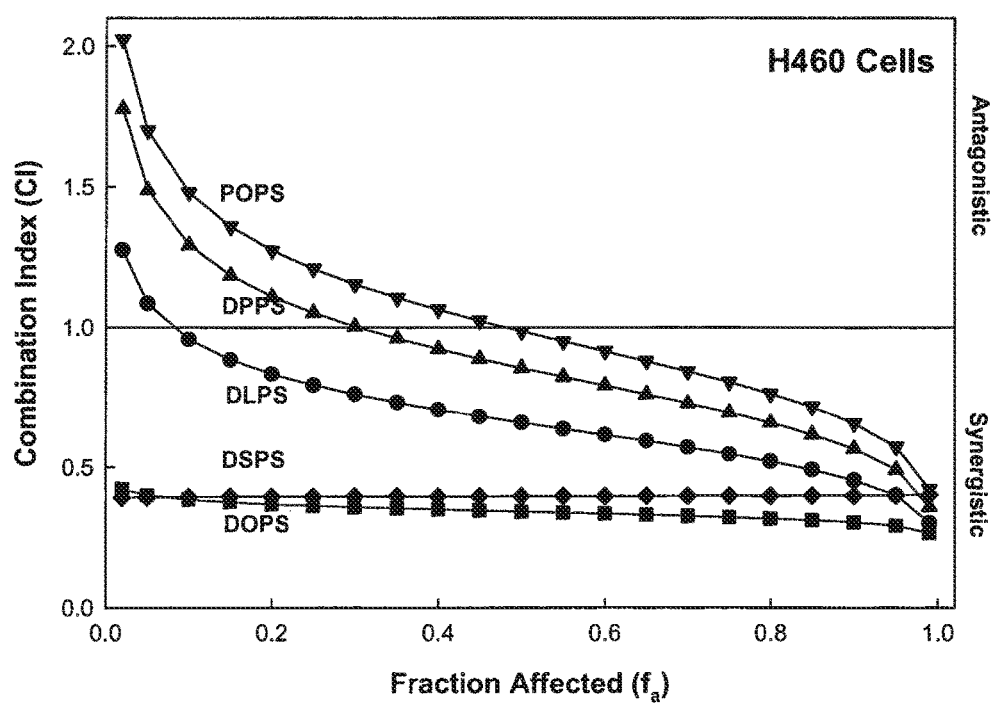
FIG. 24 is a graph of CI for vinorelbine in combination with POPS (inverted triangles), DPPS (upward triangles), DLPS (circles), DSPS (diamonds) or DOPS (squares) as a function of the H460 cells affected ($f_a$) at vinorelbine:PS mole ratios of 1:1.

Results in FIG. 24 show that all combinations of vinorelbine and lipids tested on H460 cells exhibit synergy over a substantial range of $f_a$ values. In particular, the combinations of vinorelbine with DLPS, DSPS and DOPS exhibit synergy at the majority of $f_a$ values, most notably between $f_a=0.2$ to $f_a=0.8$.

Example 18

Pharmacokinetics of Liposomal Vinorelbine and Phosphatidylserine

Liposomes consisting of SM/Chol/DPPS/DSPE-PEG2000 (35:45:10:10 mol %) were prepared and loaded with vinorelbine as follows:

Lipids were dissolved in chloroform at 100 mg/mL, and then combined in the appropriate amounts. The exception to this is DPPS which was dissolved at 25 mg/mL using $CHCl_3$/methanol/$H_2O$/citrate buffer (20:10.5:1:1 v/v). Trace amounts of the radioactive lipid $^3$H-CHE was added at this point to follow the lipid throughout the formulation process. The chloroform was removed under a stream of $N_2$ gas until very little solvent remained. The resulting lipid films were left under vacuum overnight to remove any residual solvent. The lipid films were rehydrated in citrate buffer (300 mM, pH 4.0) and the resulting MLVs were extruded at 65° C. through two 100 nm pore size filters for a total of ten passes.

Vinorelbine was loaded into these formulations using the pH gradient loading method by titrating up the external buffer pH with the use of 0.2 M $Na_2HPO_4$. A known amount of liposomes were combined with the corresponding amount of vinorelbine (0.1 drug/lipid weight ratio (w/w)) and incubated at 60° C. for 15 minutes. In order to establish a pH gradient, 0.2 M $Na_2HPO_4$ was added at ten times the volume of the citrate buffer. Vinorelbine was loaded into the liposomes to achieve a vinorelbine/phosphatidylserine mole ratio that was identified as non-antagonistic in Example 17.

The detergent OGP was used to solubilize the vinorelbine-loaded liposomes; drug levels were measured by absorbance at 270 nm and liquid scintillation counting was used to quantify lipid.

The resulting vinorelbine-loaded liposomes and free vinorelbine were administered intravenously into SCID/rag2 mice at a drug dose of 10 mg/kg. At the indicated time points (3 mice per time point), blood was collected by cardiac puncture and placed into EDTA coated microtainers. The samples were centrifuged and plasma was carefully transferred to another tube. Blood was analyzed for remaining $^3$H-CHE liposomal marker using scintillation counting. Plasma levels of vinorelbine were assayed by HPLC.

Figure 25A:
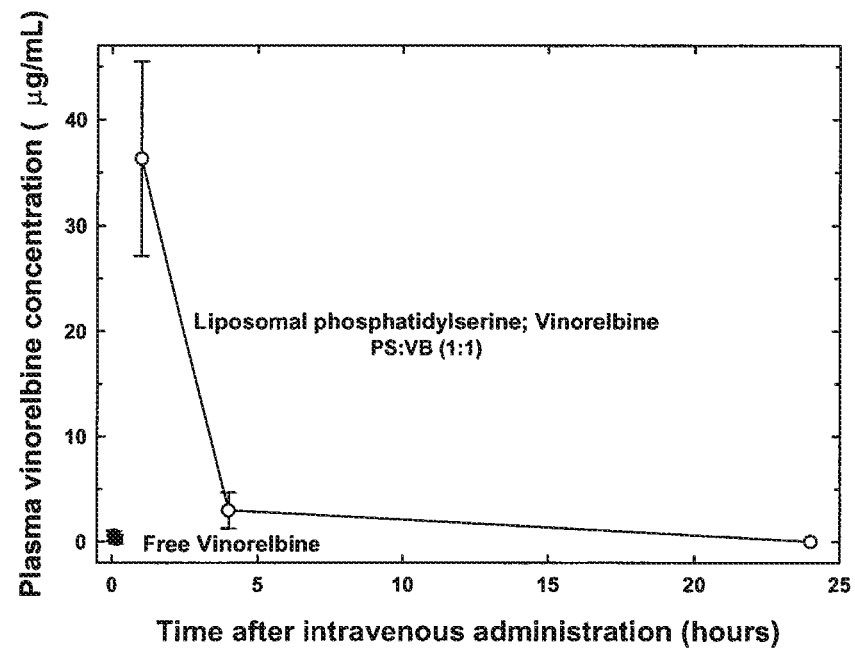
FIG. 25A is a graph of the vinorelbine concentration in plasma as a function of time after intravenous administration to SCID/rag2 mice of free vinorelbine (filled circles) or encapsulated in SM/Chol/DPPS/DSPE-PEG2000, 35:45:10:10 mol % liposomes (open circles) at a vinorelbine:PS mole ratio of 1:1.
Figure 25B:
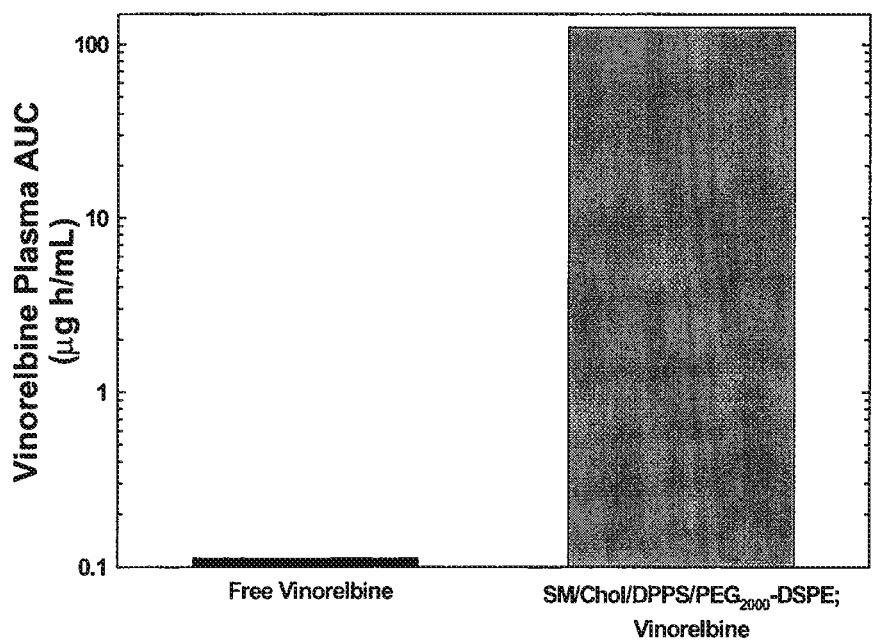
FIG. 25B is a histogram showing plasma concentration area under the curve (AUC) for free vinorelbine (black bar) or encapsulated in SM/Chol/DPPS/DSPE-PEG2000, 35:45:10:10 mol % (grey bar) after intravenous administration to SCID/rag2 mice, using the data of FIG. 25A.

FIGS. 25A and 25B show that SM/Chol/DPPS/DSPE-PEG2000 liposomes encapsulating vinorelbine exhibit substantially increased plasma drug levels in relation to administration of free vinorelbine. The free vinorelbine mean area under the curve (AUC) of 0.112 μg h/mL was increased to 125.3 μg h/mL by formulation in the liposomes, representing a 1120 fold increase in mean AUC.

Example 19

Efficacy of Liposomal Phosphatidylserine and Vinorelbine in the H460 Human Lung Cancer Model DSPC/Chol/DSPS/DSPE-PEG2000 (35:45:10:10 mol %), SM/Chol/DPPS/DSPE-PEG2000 (35:45:10:10 mol %) and DAPC/Chol/DPPS/DSPE-PEG2000 (35:45:10:10 mol %) liposomes were prepared and loaded with vinorelbine as described in Example 18. Phosphatidylserine and vinorelbine were present in the liposomes at a non-antagonistic mole ratio (1:1). Efficacy studies were carried out in the H460 human lung cancer model as described in Example 26.

Figure 26:
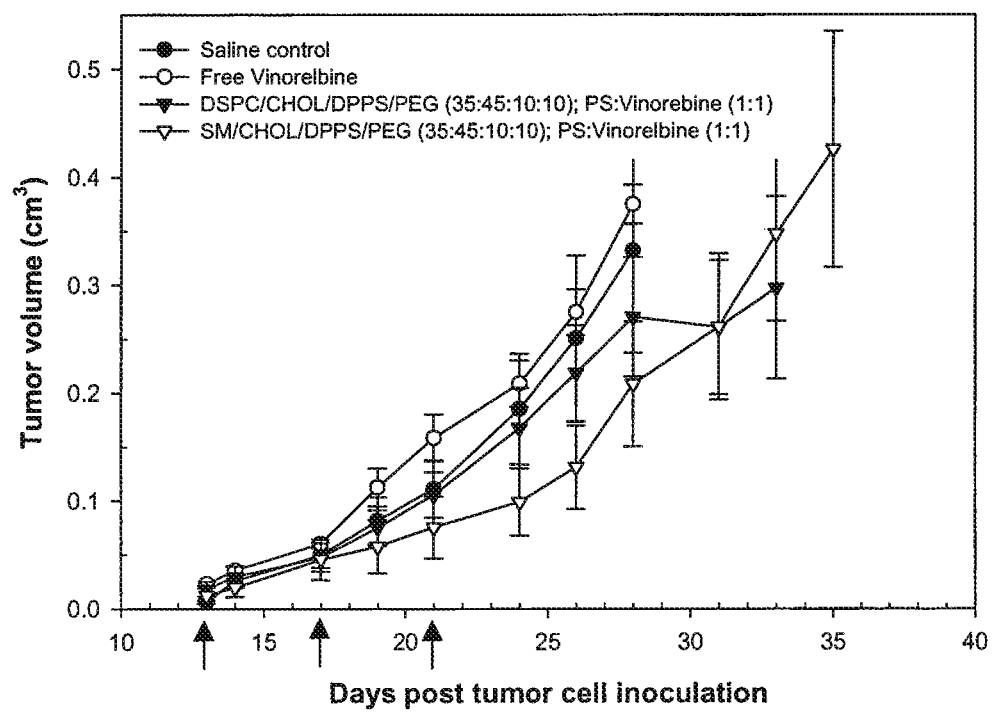
FIG. 26 is a graph comparing the activity of free vinorelbine (open circles), vinorelbine encapsulated in DSPC/Chol/DPPS/DSPE-PEG2000, 35:45:10:10 mol % liposomes (filled inverted triangles), vinorelbine encapsulated in SM/Chol/DPPS/DSPE-PEG2000, 35:45:10:10 mol % liposomes (open triangles) or saline control (filled circles) given to mice bearing the H460 non-small cell lung tumor. Vinorelbine and phosphatidylserine (DPPS) were formulated at a non-antagonistic mole ratio (1:1). Arrows indicate the days on which the doses were administered.

FIG. 26 shows for H460 tumor bearing mice (4 mice per group) given intravenous administration of liposomes consisting of DSPC/Chol/DPPS/DSPE-PEG2000 and SM/Chol/DPPS/DSPE-PEG2000 and encapsulated vinorelbine, that treatment engendered decreased tumor growth rates relative to those observed following treatment with free vinorelbine and saline. Free vinorelbine was administered at 5 mg/kg and liposomal vinorelbine was administered at a dose of 5 mg/kg of the drug and 50 mg/kg lipid at 13, 17 and 21 days post tumor cell inoculation.

Figure 27:
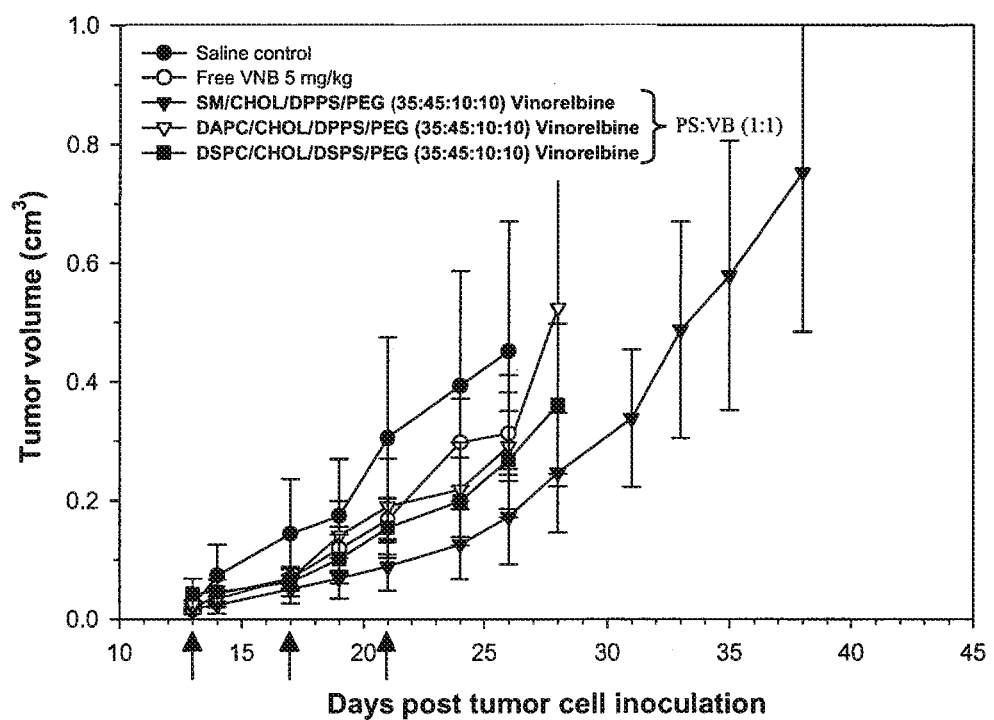
FIG. 27 shows the effect of saline control (filled circles); free vinorelbine (open circles); vinorelbine encapsulated in: SM/Chol/DPPS/DSPE-PEG2000, 35:45:10:10 (filled inverted triangles), DAPC/Chol/DPPS/DSPE-PEG2000, 35:45:10:10 mol % (open triangles), and DSPC/Chol/DSPS/DSPE-PEG2000, 35:45:10:10 mol % (filled squares) liposomes given to mice bearing the H460 non-small cell lung tumor. Vinorelbine and phosphatidylserine (DPPS or DSPS) were formulated at a non-antagonistic mole ratio (1:1). Arrows indicate the days on which the doses were administered.

FIG. 27 (data points represent mean tumor size+/−SEM determined on the specified day) shows that liposomes consisting of SM/Chol/DPPS/DSPE-PEG2000; DAPC/Chol/DPPS/DSPE-PEG2000 and DSPC/Chol/DSPS/DSPE-PEG2000 and encapsulating vinorelbine display decreased tumor volume with time relative to free vinorelbine and saline. Tumor-bearing mice (4 per group) were treated at a vinorelbine dose of 5 mg/kg (free and liposomal) and a lipid dose of 50 mg/kg for the liposomal group. Mice were treated intravenously on days 13, 17 and 21.

Example 20

Efficacy of Liposomal Phosphatidylserine and Vinorelbine in the Murine Leukemia Cancer Model Liposomes consisting of SM/Chol/DPPS/DSPE-PEG2000 (35:45:10:10 mol %) were prepared and loaded with vinorelbine as described in Example 18, except that liposomes were extruded through a 100 nm pore filter stacked with an 80 nm filter.

P388/wt cells were inoculated intraperitonealy into BDF-1 mice as described in Example 27. Subsequently, BDF1 female mice were intraperitonealy administered one of the following: saline; free vinorelbine (10 mg/kg) and SM/Chol/DPPS/DSPE-PEG2000 liposomes loaded with vinorelbine (10 mg/kg vinorelbine and 100 mg/kg lipid). Intraperitoneal administration of free and liposomal vinorelbine was carried out on day 1 with 4 mice per treatment group.

Figure 28:
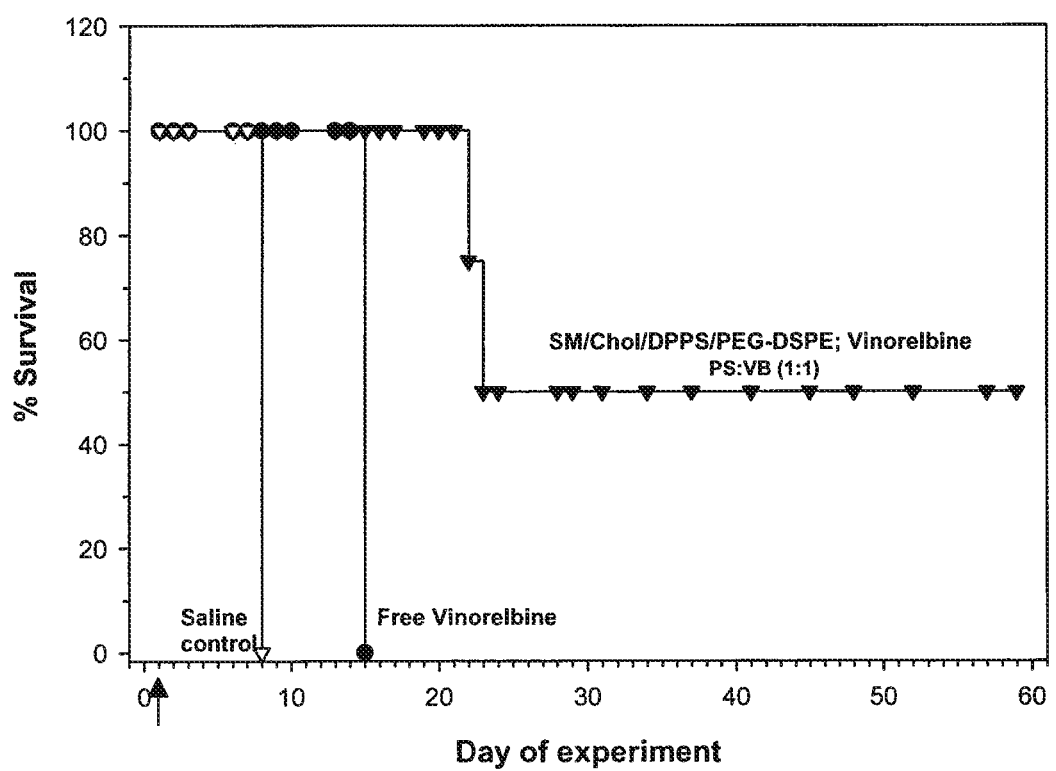
FIG. 28 shows the effect of saline control (open triangles); free vinorelbine (filled circles); and vinorelbine encapsulated in SM/Chol/DPPS/DSPE-PEG2000, 35:45:10:10 mol % liposomes (filled inverted triangles) on percent survival of P388 murine leukemia bearing mice. Vinorelbine and phosphatidylserine were formulated at a non-antagonistic mole ratio (1:1). The arrow along the x-axis indicate the day on which the doses were administered.

The survival curves shown in FIG. 28 demonstrate that administration of vinorelbine encapsulated in liposomes consisting of SM/Chol/DPPS/DSPE-PEG2000 results in substantially increased survival rates in BDF-1 mice relative to free vinorelbine and saline treatment.

Example 21

Co-Formulation of Sphingosine and Doxorubicin

Other therapeutic lipids besides phosphatidylserine may be incorporated into liposome membranes. For instance, sphingosine and sphingosine analogues are lipids that are amenable to formulation in liposomes and may be co-formulated with a therapeutic agent that is encapsulated in the aqueous interior (for example, doxorubicin). The preparation of such a pharmaceutical composition (sphingosine) may be carried out as follows:

A typical liposomal formulation of sphingosine is composed of DSPC/Chol/sphingosine (45:45:10 mol %). Lipid films are prepared as detailed in the previous examples. The lipid films are rehydrated in citrate buffer (300 mM, pH 4) and the resulting MLVs are extruded at 65° C. through two 100 nm filters for a total of ten passes. Doxorubicin is subsequently loaded into these formulations using the pH gradient loading method by exchanging the external buffer of the liposomes by passage down a Sephadex G-50 column that is equilibrated in HBS (pH 7.4) to establish a pH gradient.

The liposomes and doxorubicin solution are then incubated together at 60° C. to allow loading to occur. To determine the extent of loading at various times, 100 uL of the sample is applied to a 1 mL Sephadex G-50 spun column and then centrifuged. A drug to lipid ratio for the spun column eluent is generated using liquid scintillation counting to quantitate lipid and absorbance at 480 nm to quantitate doxorubicin. To assay for drug, the liposomes are solubilized by incubation in Triton X-100 before absorbance readings are taken.

Example 22

Synergism of Floxuridine (FUDR) and Irinotecan (CPT-11)

Figure 29:
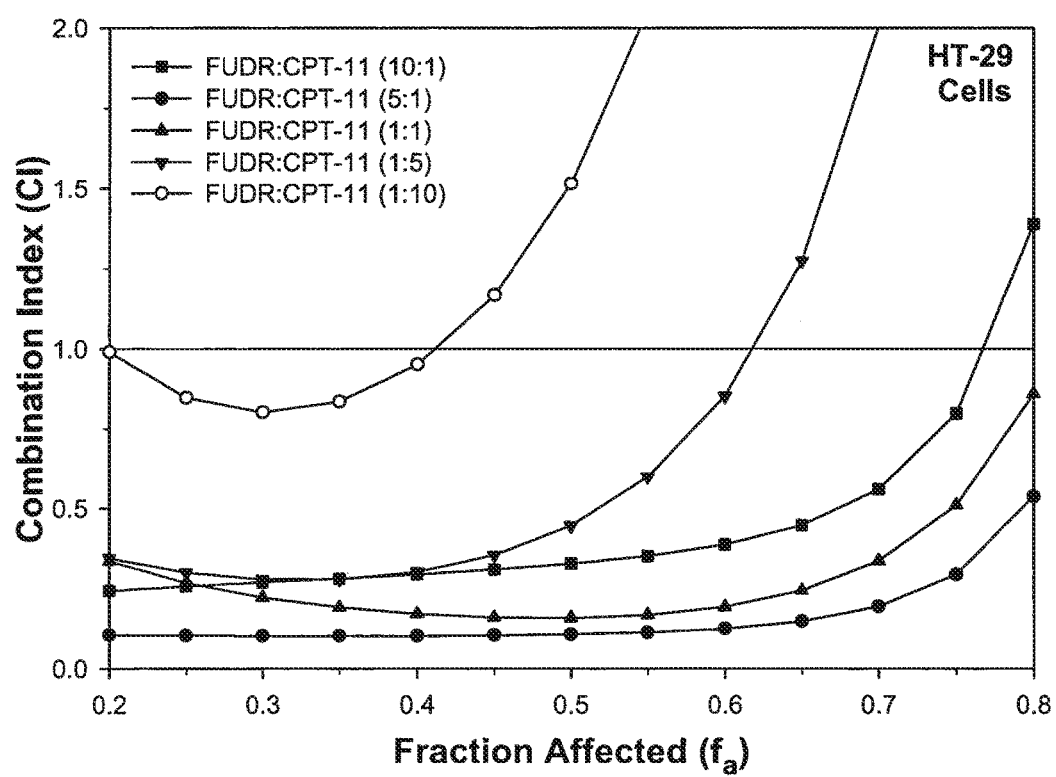
FIG. 29 shows CI plotted as a function of the fraction of HT-29 cells affected by combinations of FUDR:CPT-11 at various ratios: 10:1 (solid squares); 5:1 (solid circles); 1:1 (solid triangles); 1:5 (solid inverted triangles); and 1:10 (open circles).

The procedure set forth above for measuring additive, synergistic or antagonistic effects was repeated using FUDR/CPT-11 at 10:1, 5:1, 1:1, 1:5 and 1:10 mole ratios in HT 29 cells. A combination index was determined for each dose by producing CI versus $f_a$ curves as described above. Data in FIG. 29, plotted as CI versus the fraction of HT-29 cells affected, clearly illustrates the effect of concentration on synergy. At a ratio of 5:1 or 1:1 synergy is observed over the entire range of fraction affected values (0.2 to 0.8) while a 10:1 ratio is non-antagonistic at $f_a$ values below 0.76 and a 1:5 mole ratio of FUDR/CPT-11 is non-antagonistic at $f_a$ values less than 0.62. A 1:10 ratio is antagonistic over a substantial range of $f_a$ values (more than 50%). Based on these results, a mole ratio of 1:1 FUDR:CPT-11 was selected for formulation and efficacy studies as this ratio demonstrated synergistic effects over a significant range of $f_a$ values (at least 20% where greater than 1% of the cells are affected). Formulations prepared at the 5:1 and 10:1 ratio would also meet the requirements of a defined non-antagonistic ratio over a substantial range of $f_a$ values.

Example 23

Maintaining Synergism of FUDR and CPT-11 In Vivo

FUDR and CPT-11 were formulated into DSPC/DSPG/Chol (70:20:10 mol %) liposomes at a 1:1 mole ratio identified in Example A to be synergistic. Lipid films were prepared by dissolving DSPC and cholesterol in chloroform and DSPG in chloroform/methanol/water (16/18/1). The solutions were combined together such that the specified mole ratio was achieved and trace quantities of $^{14}$C-CHE were added as a liposomal lipid label. Following solvent removal the resulting lipid films were hydrated in a solution consisting of 250 mM $CuSO_4$ and 25 mg/mL of FUDR (with trace amounts of $^3$H-FUDR) at 70° C. The resulting MLVs were extruded at 70° C. by ten passes through two stacked 100 nm pore size filters. Subsequently, the liposomes were buffer exchanged into SHE, pH 7.4, by tangential flow dialysis, thus removing any unencapsulated FUDR and $CuSO_4$.

CPT-11 was added to these liposomes such that the FUDR to CPT-11 mole ratio would be 1:1. Loading of CPT-11 into the liposomes was facilitated by incubating the samples at 50° C. for 5 minutes. After loading, the samples were exchanged into HBS, pH 7.4, by tangential flow dialysis to remove EDTA or unencapsulated drug. The extent of CPT-11 loading was measured using HPLC. FUDR and lipid levels were measured using liquid scintillation.

The preparations were injected intravenously via the tail vein into Balb/c female mice. Doses of the liposomal formulations were 8.38 mg/kg of FUDR and 20 mg/kg of CPT-11. At the indicated time points (3 mice per time point), blood was collected by cardiac puncture and placed into EDTA coated microtainers. The samples were centrifuged and plasma was transferred to another tube. Liquid scintillation counting was used to quantitate radiolabeled lipid and FUDR in the plasma. CPT-11 plasma levels were quantified with HPLC.

Figure 30:
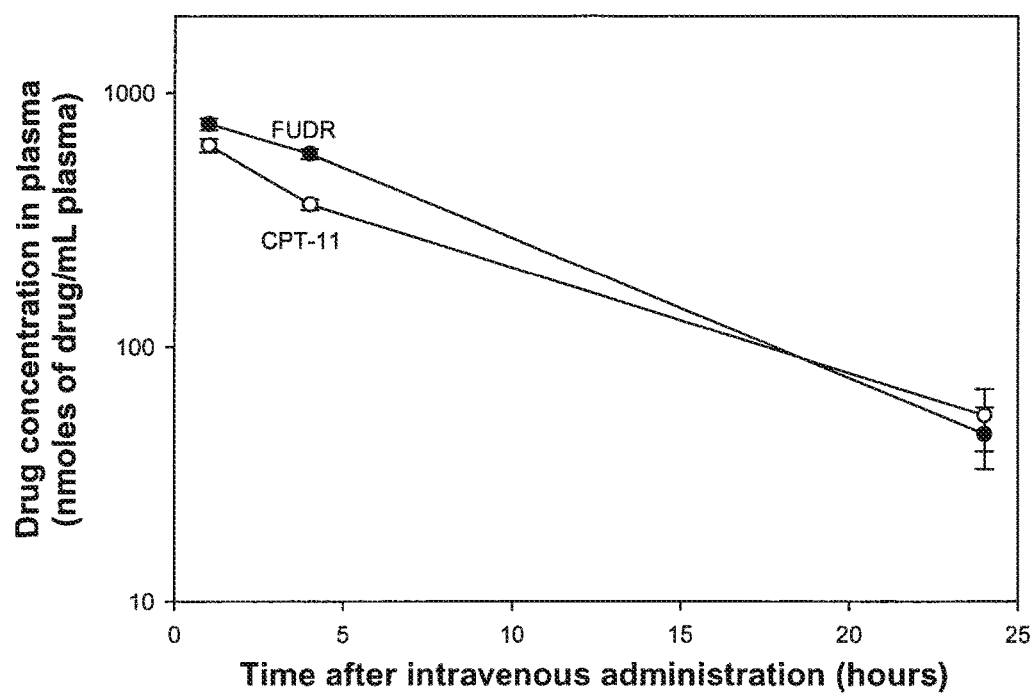
FIG. 30 is a graph of plasma concentration levels of FUDR (solid circles) and CPT-11 (open circles) as a function of time after intravenous administration.

FIG. 30 shows that plasma levels of FUDR and CPT-11 were maintained at a 1:1 mole ratio as plasma levels of FUDR were roughly equal to that of CPT-11 at various time points after intravenous administration when they were delivered in the above-described liposomes. Data points represent mean drug concentrations (nmoles drug/mL plasma) determined in plasma+/−standard deviation at the specified time points.

Example 24

Efficacy of Liposomal FUDR and CPT-11

DSPC/DSPG/Chol (70:20:10 mol %) liposomes co-encapsulated with FUDR and irinotecan at a mole ratio of 1:1 were prepared as described in Example B except that after drug loading the external liposome buffer was exchanged to 0.9% NaCl.

Using the methods of Example 26, efficacy studies were carried out in female SCID/rag2 mice that had been inoculated subcutaneously in the flank with 2×10$^6$ HT-29 cells. Tumors were allowed to grow until they measured to be 180 mg (0.18 cm$^3$) in size, at which time (day 21) the indicated formulations were injected. Tumor growth was determined by direct caliper measurements. Mice were treated with a single dose (arrow) of saline, free drug cocktail at a 1:1 mole ratio or a liposomal formulation of FUDR/CPT-11 at a 1:1 mole ratio. For both the cocktail and liposome-formulated treatments, the doses were 9.25 mg/kg FUDR and 25 mg/kg CPT-11. Lipid doses were 278 mg/kg lipid for liposome formulated samples.

Figure 31:
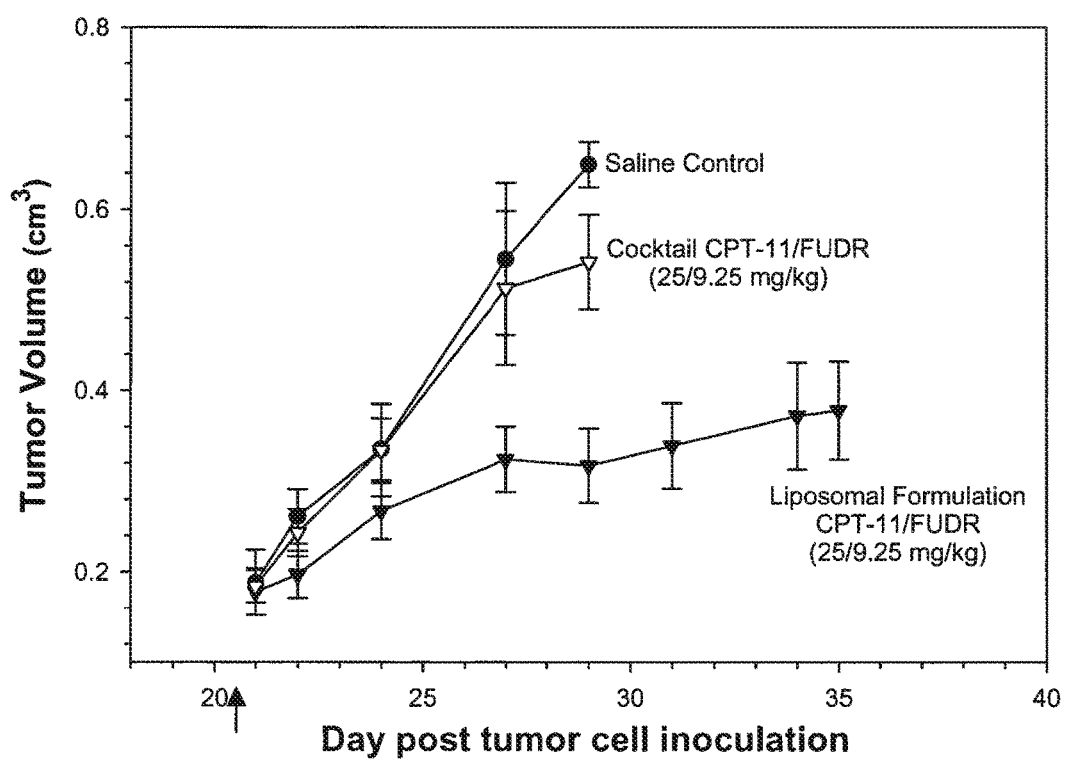
FIG. 31 is a graph of tumor volume versus time after tumor cell inoculation for saline controls (solid circles)

Results presented in FIG. 31 show that administration of FUDR and CPT-11 encapsulated in a single liposome at a 1:1 mole ratio provided significantly better therapeutic activity when compared to animals injected with either the free drug cocktail or saline. Data points represent mean tumor size+/−standard error of the mean (SEM).

Example 25

Determination of CI for Various Three-Drug Combinations

Combinations comprising topotecan, cisplatin, HB5-5A (an analog of edelfosine) and sphingosine were tested for additive, synergistic or antagonistic effects using the standard tetrazolium-based colorimetric MTT cytotoxicity assay (see Examples—Cytotoxicity Assay). Combination effects were calculated using the median-effect analysis described in the previous examples. CI versus $f_a$ graphs were created as described in the preceding examples and CI values corresponding to $f_a$ values at 0.50, 0.75 and 0.90 (represented by ED50, 75 and 90) are reported in table below:

| AGENT 1 | AGENT 2 | AGENT 3 | FIXED RATIO | COMBINATION INDEX[a] | | |
|---|---|---|---|---|---|---|
| | | | | $ED_{50}$[b] | $ED_{75}$ | $ED_{90}$ |
| Topotecan | Cisplatin | HB5-5A | 1:10:1 | 0.56 | 0.34 | 0.26 |
| Topotecan | Cisplatin | HB5-5A | 1:10:10 | 0.73 | 0.53 | 0.43 |
| Topotecan | Cisplatin | HB5-5A | 1:10:100 | 2.22 | 1.78 | 1.45 |
| Topotecan | Cisplatin | Sphingosine | 1:10:1 | 0.23 | 0.12 | 0.07 |
| Topotecan | Cisplatin | Sphingosine | 1:10:10 | 0.47 | 0.34 | 0.29 |
| Topotecan | Cisplatin | Sphingosine | 1:10:100 | 1.22 | 0.95 | 0.76 |

[a]Combination Index (CI) is used to determine synergy (CI < 0.9) or additivity (CI between 0.9 and 1.1) based on the Chou Talalay theory of dose effect analysis. Values were calculated using CalcuSyn Software.
[b]$ED_{50}$, $ED_{75}$, $ED_{90}$ refer to the dose of the agent(s) affecting 50, 75 or 90% of the measured response, respectively.

Example 26

Preparation of Tumor Models, Cell Preparation and Implantation for a Solid Subcutaneous Tumor Method H460 human non-small cell lung carcinoma cells are obtained from the DCTC Tumor Repository of the NCI. The cells are maintained in tissue culture for up to 20 passages. After 20 passages, new cells are expanded from a frozen stock stored in liquid nitrogen. When the cultured cells reached a confluence of 80-90% they are rinsed with Hanks Balanced Salt Solution and the adherent cells are removed with a 0.25% trypsin solution. Cells are counted on a haemocytometer and diluted with media to a concentration of $20 \times 10^6$ cells/mL.

A patch of hair approximately 2 cm×2 cm is shaved using electric clippers in the lower back region of each mouse. Using a 28 g needle, mice are inoculated subcutaneously with $1 \times 10^6$ tumor cells on day 0 (one inoculum/mouse) in a volume of 50 μL.

When tumors reach a defined size of approximately 0.50-to-0.100 cm$^3$, either one-day prior to treatment or on the day of treatment (~day 10-14), all tumors are measured. After selecting the appropriate tumor sizes, excluding tumors too small or large, the tumors are randomly distributed (n=4) and the mean tumor volume of the groups are determined.

Mice are organized into appropriate treatment groups and consist of control and treatment groups such as, saline control, vehicle control, positive control and various dilutions of test articles.

Treatment groups are as follows:

| GROUP | MICE/ GROUP | TREATMENT | DOSE (MG/KG) | SCHEDULE[a] | VOLUME INJECTION |
|---|---|---|---|---|---|
| 1 | 4 | Saline control | N/A | q4dx3 | 10 μL/g |
| 2 | 4 | Vehicle control | 20 | q4dx3 | 10 μL/g |
| 3 | 4 | Positive control | 10 | q4dx3 | 10 μL/g |
| 4 | 4 | Test agent (low dose) | 5 | q4dx3 | 10 μL/g |
| 5 | 4 | Test agent (medium dose) | 10 | q4dx3 | 10 μL/g |
| 6 | 4 | Test agent (high dose) | 20 | q4dx3 | 10 μL/g |

[a]Alternative dosing schedules can be considered such as a single dose or 3 doses every 4-7 days Mice are injected intravenously with the required volume of sample to administer the prescribed dose (10 μL/g as indicated) to the animals based on individual mouse weights.

Tumor growth measurements are monitored using vernier calipers beginning on the day of treatment. Tumor length measurements (mm) are made from the longest axis and width measurements (mm) will be perpendicular to this axis. From the length and width measurements tumor volumes (cm$^3$) are calculated according to the equation $(L \times W^2/2)/1000$. Animal weights are collected at the time of tumor measurement.

Individual mouse body weights are recorded at various days (generally two days apart such as Monday, Wednesday and Friday) during the efficacy study for a period of 14-days after the last dosing.

All animals are observed at least once a day, more if deemed necessary, during the pre-treatment and treatment periods for mortality and morbidity. In particular, signs of ill health are based on body weight loss, change in appetite, rough coat, lack of grooming, behavioral changes such as altered gait, lethargy and gross manifestations of stress. Should signs of severe toxicity or tumor-related illness be seen, the animals are euthanized ($CO_2$ asphyxiation) and a necropsy is performed to assess other signs of toxicity. Moribund animals must be terminated for humane reasons and the decision to terminate will be at the discretion of the Animal Care Technician and the Study Director/Manager. Any and all of these findings will be recorded as raw data and the time of death will be logged as the following day.

Data are presented in either tabular or figure form as follows:
1. Plot of individual mouse tumor volumes with respect to each group, prior to treatment start and after grouping.
2. Mean body weights for each group as a function of time.
3. Mean tumor volumes for each group as a function of time.
4. Raw data including figures and tables are generated and include tumor growth vs. time, tumor growth inhibition, and tumor growth delay.

5. Summary of abnormal or remarkable observations.

Example 27

Preparation of Tumor Models, Cell Preparation and Implantation for an Intraperitoneal Tumor Method Mice are grouped according to body weight. Animals (n=4) are inoculated (Day=0) with $1 \times 10^6$ P388 cells implanted in the peritoneum cavity of BDF-1 mice in a volume of 500 µL with a 25 g needle. P388 cells from the ATCC tumor repository are maintained as an ascitic fluid in the BDF-1 mouse, which are passaged to new mice weekly. Mice are euthanized, and the ascitic cells removed through the abdominal wall with a 20 g needle. The cells used for experiment are used within passage 3-20. After 20 passages in the mice, new cells are brought up from the frozen stock in liquid nitrogen, and mice are inoculated. For experiments, cells are rinsed with Hanks Balanced Salt Solution, counted on a haemocytometer and diluted with HBSS to a concentration of $2 \times 10^6$ cells/mL.

Study groupings are performed randomly after all mice have been administered tumor cells. The required groupings are similar to what is performed for solid tumor studies (see Example 26).

Mice are injected intravenously or intraperitonealy with the required volume of sample to administer the prescribed dose (10 µL/g as indicated) to the animals based on individual mouse weights. With intraperitoneal tumors, administrations generally begin 1-day post tumor cell inoculation.

Animal well-being is closely monitored daily. Signs of ill health and progression of morbidity are closely monitored as described in Example 26. Animals are weighed at the time of examination.

Upon termination of any mice, gross necropsies are performed to evaluate the extent of tumor burden and/or physiologically observable changes in organ appearances. Findings are recorded.

Group body weights are recorded Monday through Friday during the efficacy study for a period of 14 days after the last dosing.

All animals are observed at least once a day, more if deemed necessary, during the pre-treatment and treatment periods for mortality and morbidity. In particular, signs of ill health are based on body weight loss, change in appetite, behavioral changes such as altered gait, lethargy and gross manifestations of stress. Should signs of severe toxicity or tumor-related illness be seen, the animals are terminated ($CO_2$ asphyxiation) and a necropsy is performed to assess other signs of toxicity. Moribund animals must be terminated for humane reasons and the decision to terminate will be at the discretion of the animal care technician and the study manager. These findings are recorded as raw data and the time of death is logged on the following day.

Data is presented in tables or figures and includes mean body weights for each group as a function of time and increase in life-span.

The invention claimed is:

1. A pharmaceutical composition for parenteral administration, comprising particulate delivery vehicles having associated therewith at least a first antineoplastic agent and a second antineoplastic agent, wherein said first and second agents are in a mole ratio which exhibits a non-antagonistic cytotoxic or cytostatic effect in an in vitro assay, over at least 20% of the concentration range over which the fraction of cells affected is 0.2-0.8; and wherein said first and second agents are associated with the delivery vehicles to maintain said non-antagonistic ratio in the blood for at least one hour after administration, wherein said delivery vehicles comprise
liposomes, and/or
lipid micelles, and/or
block copolymer micelles, and/or
polymer microparticles, and/or
polymer nanoparticles, and/or
polymer lipid hybrid systems, and/or
derivatized single chain polymers, and
wherein the composition comprises one or more additional therapeutic agents.

2. The composition of claim 1 wherein said delivery vehicles are 4 to 6,000 nm in diameter.

3. The composition of claim 1 wherein said delivery vehicles have a mean diameter of between 4.5 and 500 nm.

4. The composition of claim 1 wherein said vehicles have a mean diameter of less than 250 nm.

5. The composition of claim 1 wherein said delivery vehicles are from 4 µm to 50 µm in diameter.

6. The composition of claim 1 wherein said delivery vehicles comprise liposomes.

7. The composition of claim 1 wherein said first and second antineoplastic agents are co-encapsulated.

8. The composition of claim 1 wherein at least one of the antineoplastic agents is selected from the group consisting of a DNA damaging agent, a DNA repair inhibitor, a topoisomerase I inhibitor, a topoisomerase II inhibitor, a cell checkpoint inhibitor, a CDK inhibitor, a receptor tyrosine kinase inhibitor, a cytotoxic agent, an apoptosis inducing agent, an antimetabolite, a cell cycle control inhibitor, a therapeutic lipid, a telomerase inhibitor, an anti-angiogenic agent, a mitochondrial poison, a signal transduction inhibitor and an immunoagent.

9. The composition of claim 7 wherein the first antineoplastic agent is a cytoxic agent and the second antineoplastic agent is a cell-cycle inhibitor, or wherein the first antineoplastic agent is a DNA damaging agent and the second antineoplastic agent is a DNA repair inhibitor, or
wherein the first antineoplastic agent is a topoisomerase I inhibitor and the second antineoplastic agent is a $S/G_2$- or a $G_2/M$-checkpoint inhibitor, or
wherein the first antineoplastic agent is a $G_1/S$ checkpoint inhibitor or a cyclin-dependent kinase inhibitor and the second antineoplastic agent is a $G_2/M$ checkpoint inhibitor, or
wherein the first antineoplastic agent is a receptor kinase inhibitor and the second antineoplastic agent is a cytotoxic agent, or
wherein the first antineoplastic agent is an apoptosis-inducing agent and the second antineoplastic agent is a cytotoxic agent, or
wherein the first antineoplastic agent is an apoptosis-inducing agent and the second antineoplastic agent is a cell-cycle control agent, or
wherein the first antineoplastic agent is a telomerase inhibitor and the second antineoplastic agent is a cell-cycle control inhibitor, or
wherein the first and second antineoplastic agents are antimetabolites, or
wherein the first and second antineoplastic agents are cytotoxic agents, or
wherein the first antineoplastic agent is a therapeutic lipid and the second antineoplastic agent is a cytotoxic agent, or wherein the first antineoplastic agent is a topoisomerase I inhibitor and the second antineoplastic agent is a DNA repair inhibitor, or wherein the apoptosis-inducing antineoplastic agent is a serine-containing lipid.

10. The composition of claim 1 wherein the first antineoplastic agent is irinotecan and the second antineoplastic agent is 5 FU or FUDR, or wherein the first antineoplastic agent is cisplatin (or carboplatin) and the second antineoplastic agent is 5 FU or FUDR, or wherein the first antineoplastic agent is idarubicin and the second antineoplastic agent is AraC or FUDR, or wherein the first antineoplastic agent is oxaliplatin and the second antineoplastic agent is 5 FU or FUDR, or wherein the first antineoplastic agent is irinotecan and the second antineoplastic agent is cisplatin (or carboplatin), or wherein the first antineoplastic agent is gemcitabine and the second antineoplastic agent is cisplatin (or carboplatin), or wherein the first antineoplastic agent is methotrexate and the second antineoplastic agent is 5 FU or FUDR, or wherein the first antineoplastic agent is paclitaxel and the second antineoplastic agent is cisplatin (or carboplatin), or wherein the first antineoplastic agent is etoposide and the second antineoplastic agent is cisplatin (or carboplatin), or wherein the first antineoplastic agent is docetaxel or paclitaxel and the second antineoplastic agent is doxorubicin, or wherein the first antineoplastic agent is doxorubicin and the second antineoplastic agent is vinorelbine, or wherein the first antineoplastic agent is carboplatin and the second antineoplastic agent is vinorelbine, or wherein the first antineoplastic agent is 5-FU or FUDR and the second antineoplastic agent is gemcitabine.

11. The composition of claim 6 wherein the first antineoplastic agent is daunorubicin and the second antineoplastic agent is AraC.

12. The composition of claim 1 wherein the one or more additional therapeutic agents is a cytotoxic agent.

13. The composition of claim 1 where the one or more additional therapeutic agents is selected from an apoptosis-inducing agent, a signal transduction inhibitor or a receptor tyrosine kinase inhibitor.

14. A method to prepare a composition of claim 1, which method comprises stably associating with said particulate delivery vehicles a mole ratio of agents that has been determined to exhibit a non-antagonistic cytotoxic or cytostatic effect in an in vitro assay over at least 20% of the concentration range over which the fraction of cells affected is 0.2-0.8;

wherein said stable association is such that said ratio is maintained in the blood for at least one hour after administration, wherein said method further comprises adding said one or more additional therapeutic agents.

15. The method of claim 14, wherein said ratio has been determined in an assay that employs testing at least one ratio of said agents at a multiplicity of concentrations and applying an algorithm to calculate a synergistic, additive, or antagonistic effect for said ratio over a range of concentrations.

16. The method of claim 15 which employs testing a multiplicity of ratios, and wherein said algorithm is the Chou-Talalay median effect method.

17. The method of claim 14 wherein the delivery vehicles are liposomes.

18. The method of claim 17 wherein the first antineoplastic agent is irinotecan and the second antineoplastic agent is 5-FU or FUDR, or wherein the first antineoplastic agent is cisplatin (or carboplatin) and the second antineoplastic agent is 5-FU or FUDR, or wherein the first antineoplastic agent is idarubicin and the second antineoplastic agent is AraC or FUDR, or wherein the first antineoplastic agent is oxaliplatin and the second antineoplastic agent is 5-FU or FUDR, or wherein the first antineoplastic agent is irinotecan and the second antineoplastic agent is cisplatin (or carboplatin), or wherein the first antineoplastic agent is gemcitabine and the second antineoplastic agent is cisplatin (or carboplatin), or wherein the first antineoplastic agent is methotrexate and the second antineoplastic agent is 5-FU or FUDR, or wherein the first antineoplastic agent is paclitaxel and the second antineoplastic agent is cisplatin (or carboplatin), or wherein the first antineoplastic agent is etoposide and the second antineoplastic agent is cisplatin (or carboplatin), or wherein the first antineoplastic agent is docetaxel or paclitaxel and the second antineoplastic agent is doxorubicin, or wherein the first antineoplastic agent is doxorubicin and the second antineoplastic agent is vinorelbine, or wherein the first antineoplastic agent is carboplatin and the second antineoplastic agent is vinorelbine, or wherein the first antineoplastic agent is 5-FU or FUDR and the second antineoplastic agent is gemcitabine.

19. The method of claim 14 wherein the first antineoplastic agent is daunorubicin and the second antineoplastic agent is AraC.

20. A method to treat a disease or condition in a subject, which method comprises administering to a subject in need of such treatment the pharmaceutical composition of claim 1.

* * * * *